(12) United States Patent
Hart et al.

(10) Patent No.: US 7,781,164 B2
(45) Date of Patent: Aug. 24, 2010

(54) METHOD FOR DIAGNOSING RENAL DISEASES OR PREDISPOSITIONS

(75) Inventors: Thomas C. Hart, Potomac, MD (US); Patricia Suzanne Hart, Potomac, MD (US); Michael Gorry, Pittsburgh, PA (US); Anthony J. Bleyer, Winston-Salem, NC (US)

(73) Assignees: University of Pittsburgh - Of the Commonwealth System of Higher Education, Pittsburgh, PA (US); Wake Forest University, Winston-Salem, NC (US)

( * ) Notice: Subject to any disclaimer, the term of this patent is extended or adjusted under 35 U.S.C. 154(b) by 803 days.

(21) Appl. No.: 11/112,327

(22) Filed: Apr. 23, 2005

(65) Prior Publication Data
US 2007/0207464 A1   Sep. 6, 2007

Related U.S. Application Data

(63) Continuation-in-part of application No. PCT/US03/33957, filed on Oct. 23, 2003.

(60) Provisional application No. 60/420,768, filed on Oct. 23, 2002, provisional application No. 60/430,318, filed on Dec. 2, 2002.

(51) Int. Cl.
  C12Q 1/68  (2006.01)
  C12P 19/34 (2006.01)
  C07H 21/02 (2006.01)
  C07H 21/04 (2006.01)

(52) U.S. Cl. .................. 435/6; 435/91.2; 536/23.5; 536/24.31; 536/24.33

(58) Field of Classification Search .................. None
See application file for complete search history.

(56) References Cited

OTHER PUBLICATIONS

Gene Card for UMOD available via url: < genecards.org/cgi-bin/carddisp.pl?gene=UMOD >.*
Calado et al. BMC Medical Genetics. 2005.6:5.*
Haluszka et al. Nature. Jul. 1999. 22: 239-247.*
Antonarakis et al., *Human Mutation*, 11, 1-3 (1998).
Benson, Gary, *Nucleic Acids Research*, 27(2), 573-580 (1999).
Bross et al., *Human Mutation*, 14(3), 186-198 (1999).
Cameron et al., *Pediatric Nephrology*, 7(1), 105-118 (1993).
Chen et al., *Urologia Internationalis*, 67, 305-309 (2001).
Chen et al., *Molecular Urology*, 5(1), 1-5 (2001).
*Clinical Guide to Laboratory Tests*, (Tieta et al., eds.), 186-187 (W.B. Saunders Company, Philadelphia, PA, 1995).
Cockcroft et al., *Nephron*, 16(1), 31-41 (1976).
Dahan et al., *Journal of the American Society of Nephrology*, 12(11), 2348-2357 (2001).
De La Mata et al., *Chembiochem*, 3(8), 726-740 (2002).
Den Dunnen et al., *Human Mutation*, 15(1), 7-12 (2000).
Dulawa et al., *European Journal of Clinical Investigation*, 18(1), 87-91 (1988).
Flagiello et al., *Human Mutation*, 12(5), 361 (1998).
Fletcher et al., *Biochemical Journal*, 120, 425-432 (1970).
Fossati et al., *Clinical Chemistry*, 26(13), 227-231 (1980).
Hart et al., *The American Journal of Human Genetics*, 70(4), 943-954 (2002).
Hart et al., *Journal of Medical Genetics*, 39, 882-892 (2002).
Hateboer et al., *Kidney International*, 60(4), 1233-1239 (2001).
Hession et al., *Science*, 237(4821), 1479-1484 (1987).
Hoyer et al., *Laboratory Investigation*, 41(2), 168-173 (1979).
Huang et al., *The Journal of Clinical Investigation*, 99(4), 732-736 (1997).
Jovine et al., *Nature Cell Biology*, 4(6), 457-461 (2002).
Kahn, Andrew M., *Seminars in Nephrology*, 8(3), 305-314 (1988).
Kamatani et al., *Arthritis & Rheumatism*, 43(4), 925-929 (2000).
Kelly et al., *American Journal of Kidney Diseases*, 10(5), 389-395 (1987).
Massari et al., *Archives of Internal Medicine*, 140, 680-684 (1980).
McKusick, "Hyperuricemic Nephropathy, Familial Juvenile; HNFJ," *OMIM (Online Mendelian Inheritance in Man—Johns Hopkins University)*, #162000 (Jun. 2, 1986). Retrieved on Apr. 20, 2005 from: http://www.ncbi.nlm.nih.gov/entrez/dispomim.cgi?id=162000.
McKusick, "Uromodulin; UMOD," *OMIM (Online Mendelian Inheritance in Man—Johns Hopkins University)*, #191845 (Jun. 6, 1994). Retrieved on Apr. 20, 2005 from: http://www.ncbi.nlm.nih.gov/entrez/dispomim.cgi?id=191845.
McKusick, "Medullary Cystic Kidney Disease 2; MCKD2," *OMIM (Online Mendelian Inheritance in Man—Johns Hopkins University)*, #603860 (Jun. 1, 1999). Retrieved on Apr. 20, 2005 from: http://www.ncbi.nlm.nih.gov/entrez/dispomim.cgi?id=603860.
Mikkelsen et al., *The American Journal of Medicine*, 39, 242-251 (1965).
Muchmore et al., *Science*, 229(4712), 479-481 (1985).
NCBI Entrez Nucleotide, "Human uromodulin (Tamm-Horsfall glycoprotein) mRNA," Accession No. M17778 GI:340165, (Aug. 3, 1993). Accessed on Apr. 25, 2005 at: http://www.ncbi.nlm.nih.gov/entrez/viewer.fcgi?db=nucleotide&val=340165.
NCBI Entrez Nucleotide, "Tamm-Horsfall protein [cattle, kidney, mRNA]," Accession No. S75958 GI:912814, (Jul. 27, 1995). Accessed on Apr. 25, 2005 at http://www.ncbi.nlm.nih.gov/entrez/viewer.fcgi?db=nucleotide&val=912814.
NCBI Entrez Nucleotide, "Mus musculus uromodulin (Umod), mRNA," Accession No. NM_009470 GI:31981927, (Apr. 16, 2005). Accessed on Apr. 25, 2005 at http://www.ncbi.nlm.nih.gov/entrez/viewer.fcgi?db=nucleotide&val=31981927.
NCBI Entrez Nucleotide, "Tat Tamm-Horsfall protein mRNA," Accession No. M63510 GI:207620, (Apr. 27, 1993). Accessed on Apr. 25, 2005 at: http://www.ncbi.nlm.nih.gov/entrez/viewer.fcgi?db=nucleotide&val=207620.

(Continued)

*Primary Examiner*—Carla Myers
(74) *Attorney, Agent, or Firm*—Leydig, Voit & Mayer, Ltd.

(57) ABSTRACT

The invention provides a method of diagnosing a disease or a predisposition to contract a disease by assaying for mutations of uromodulin (UMOD) within a test subject or patient. The presence of a mutation in the UMOD supports a diagnosis of a disease or a predisposition to contract a disease within the patient.

12 Claims, 36 Drawing Sheets

OTHER PUBLICATIONS

NCBI Entrez Nucleotide, "*Homo sapiens* uromodulin precursor (UMOD) gene, exons 2 through 5," Accession No. AY162963 GI29470286, (Apr. 2, 2003). Accessed on Apr. 25, 2005 at http://www.ncbi.nlm.nih.gov/entrez/viewer.fcgi?db=nucleotide&val=29470286.

NCBI Entrez Nucleotide, "*Homo sapiens* uromodulin precursor (UMOD) gene, exon 6," Accession No. AY162963S2 GI:29470287, (Apr. 2, 2003). Accessed on Apr. 25, 2005 at http://www.ncbi.nlm.nih.gov/entrez/viewer.fcgi?db=nucleotide&val=29470287.

NCBI Entrez Nucleotide, "*Homo sapiens* uromodulin precursor (UMOD) gene, exon 7," Accession No. AY162965 GI:29470288, (Apr. 2 2003). Accessed on Apr. 25, 2005 at http://www.ncbi.nlm.nih.gov/entrez/viewer.fcgi?db=nucleotide&val=29470288.

NCBI Entrez Nucleotide, "*Homo sapiens* uromodulin precursor (UMOD) gene, exon 8," Accession No. AY162967 GI:29470290, (Apr. 2, 2003). Accessed on Apr. 25, 2005 at http://www.ncbi.nlm.nih.gov/entrez/viewer.fcgi?db=nucleotide&val=29470290.

NCBI Entrez Nucleotide, "*Homo sapiens* uromodulin precursor (UMOD) gene, exons 9 and 10," Accession No. AY162968 GI:29470291, (Apr. 2, 2003). Accessed on Apr. 25, 2005 at http://www.ncbi.nlm.nih.gov/entrez/viewer.fcgi?db=nucleotide&val=29470291.

NCBI Entrez Nucleotide, "*Homo sapiens* uromodulin precursor (UMOD) gene, exon 11," Accession No. AY162969 GI:29470292, (Apr. 2, 2003). Accessed on Apr. 25, 2005 at: http://www.ncbi.nlm.nih.gov/entrez/viewer.fcgi?db=nucleotide&val=29470292.

NCBI Entrez Nucleotide, "*Homo sapiens* uromodulin precursor (UMOD) gene, exon 12," Accession No. AY162963S8 GI:29470293, (Apr. 2, 2003). Accessed on Apr. 25, 2005 at: http://www.ncbi.nlm.nih.gov/entrez/viewer.fcgi?db=nucleotide&val=29470293.

NCBI Entrez Nucleotide, "*Homo sapiens* xylosyltransferase I (XYLT1), mRNA," Accession No. NM_022166 GI:51944975, (Mar. 2, 2005). Accessed on Apr. 25, 2005 at: http://www.ncbi.nlm.nih.gov/entrez/viewer.fcgi?db=nucleotide&val=51944975.

NCBI Entrez Nucleotide, "*Homo sapiens* coenzyme Q7 homolog, ubiquinone (yeast) (COQ7), mRNA," Accession No. NM_016138 GI:25453483, (Apr. 23, 2005). Accessed on Apr. 25, 2005 at: http://www.ncbi.nlm.nih.gov/entrez/viewer.fcgi?db=nucleotide&val=25453483.

NCBI Entrez Nucleotide, "*Homo sapiens* proteasome (prosome, macropain) subunit, alpha type, 4, mRNA (cDNA clone MGC:51760 Image:6060404)," Accession No. BC047667 GI:28839482, (Jun. 30, 2004). Accessed on Apr. 25, 2005 at: http://www.ncbi.nlm.nih.gov/entrez/viewer.fcgi?db=nucleotide&val=28839482.

NCBI Entrez Nucleotide, "*Homo sapiens* G protein-coupled recepor, family C, group 5, member B (GPRC5B), mRNA," Accession No. NM_016235 GI:7706450, (Apr. 22, 2005). Accessed on Apr. 25, 2005 at: http://www.ncbi.nlm.nih.gov/entrez/viewer.fcgi?db=nucleotide&val=7706450.

NCBI Entrez Nucleotide, "*Homo sapiens* glycoprotein 2 (zymogen granule membrane) (GP2) transcript variant 2 mRNA," Accession No. NM_001502 GI:56119212, (Apr. 23, 2005). Accessed on Apr. 25, 2005 at: http://www.ncbi.nlm.nih.gov/entrez/viewer.fcgi?db=nucleotide&val=56119212.

NCBI Entrez Nucleotide, "*Homo sapiens* uromodulin (uromucoid, Tamm-Horsfall glycoprotein) (UMOD), transcript variant 1, mRNA," Accession No. NM_003361 GI:59850811, (Apr. 23, 2005). Accessed on Apr. 25, 2005 at: http://www.ncbi.nlm.nih.gov/entrez/viewer.fcgi?db=nucleotide&val=59850811.

NCBI Entrez Nucleotide, "*Homo sapiens* butyryl Coenzyme A synthetase 1 (BUCS1), mRNA," Accession No. NM_052956 GI:16418448, (Apr. 23, 2005). Accessed on Apr. 25, 2005 at: http://www.ncbi.nlm.nih.gov/entrez/viewer.fcgi?db=nucleotide&val=16418448.

NCBI Entrez Nucleotide, "Mus musculus olfactory receptor 1257 (Olfr1257), mRNA," Accession No. XM_485032 GI:51706260, (Aug. 31, 2004). Accessed on Apr. 25, 2005 at: http://www.ncbi.nlm.nih.gov/entrez/viewer.fcgi?db=nucleotide&val=51706260.

NCBI Entrez Nucleotide, "*Homo sapiens* B/K protein (LOC51760), mRNA," Accession No. NM_016524 GI:40068037, (Apr. 23, 2005). Accessed on Apr. 25, 2005 at: http://www.ncbi.nlm.nih.gov/entrez/viewer.fcgi?db=nucleotide&val=40068037.

NCBI Entrez Nucleotide, "*Homo sapiens* similar to Echinoidin (LOC162074), mRNA," Accession No. XM_091332 GI:18585569, (Aug. 1, 2002). Accessed on Apr. 25, 2005 at: http://www.ncbi.nlm.nih.gov/entrez/viewer.fcgi?db=nucleotide&val=18585569.

O'Connell et al., *Nature Genetics*, 11, 402-408 (1995).

Pace et al., *Human Mutation*, 18(4), 319-326 (2001).

Pennica et al., *Science*, 236(4797), 83-88 (1987).

Pirulli et al., *Journal of Nephrology*, 14(5), 392-396 (2001).

Resnick et al., *Laboratory Investigation*, 38(5), 550-555 (1978).

Rieselbach et al., *Nephron*, 14, 81-87 (1975).

Robinson et al., *Human Mutation*, 20(3), 153-161 (2002).

Salowsky et al., *Gene*, 293(1-2), 9-19 (2002).

Schweigert et al., *Veterinary Research*, 33(3), 299-311 (2002).

Scolari et al., *The American Journal of Human Genetics*, 64(6), 1655-1660 (1999).

Sherblom et al., *The Journal of Biological Chemistry*, 263(11), 5418-5424 (1988).

Stiburkova et al., *The American Journal of Human Genetics*, 66(6), 1989-1994 (2000).

Tamm et al., *Proceedings of the Society for Experimental Biology and Medicine*, 74, 108-114 (1950).

Tamm et al., *The Journal of Experimental Medicine*, 95, 71-97 (1952).

Terrinoni et al., *The Journal of Investigative Dermatology*, 117(6), 1391-1396 (2001).

Thompson et al., *Archives of Internal Medicine*, 138(1), 1614-1617 (1978).

Wautot et al., *Human Mutation*, 20(1), 35-47 (2002).

Wilcox, W. D., *The Journal of Pediatrics*, 128(6), 731-741 (1996).

Zager et al., *Laboratory Investigation*, 38(1), 52-57 (1978).

Zhang et al., *Cytogenetics and Cell Genetics*, 95(3-4), 146-152 (2001).

* cited by examiner

Family 1: FJHN can be traced over 7 generation in this family, and we have identified more than 200 family members. As such the pedigree is too large to present. Selected subfamilies that were studied for this report are shown.

```
                                         *    *     *        * *
Homo sapiens        MGQ-PSLTWMLMV-VVASWFITTAATDTSEARWCSECHSNATCTEDEAVTTCTCQEGFT  57
Bos taurus          MKCLFSPNFMWMAAVVTSWVIIPAATDTSSAKSCSECHSNATCTVDGAATTCACQEGFT  59
Mus musculus        MG--IPLTWMLLVMMVTSWFTLAEASNSTEARRCSECHNNATCTVDGVVTTCSCQTGFT  57
Rattus norvegicus   MGQLLSLTWLLLVMVVTPWFTVAGANDSPEARRCSECHDNATCVLDGVVTTCSCQAGFT  59

*     *      *   *         * *      *          *
Homo sapiens        GDGLTCVDLDECAIPGAHNCSANSSCVNTPGSFSCVCPEGFRLSPGLGCTDVDECAEPGL  117
Bos taurus          GDGLECVDLDECAVLGAHNCSATKSCVNTLGSYTCVCPEGFLLSSELGCEDVDECAEPGL  119
Mus musculus        GDGLVCEDMDECATPWTHNCS-NSSCVNTPGSFKCSCQDGFRLTPELSCTDVDECSEQGL  116
Rattus norvegicus   GDGLVCEDIDECATPWTHNCS-NSICMNTLGSYECSCQDGFRLTPGLGCIDVNECTEQGL  118
                                                                       ↑
                         *          *     * *       * *    *     *       *  *
Homo sapiens        SHCHALATCVNVVGSYLCVCPAGYRGDGWHCECSPGSCGPGLDCVPEG--DALVCADPCQ  175
Bos taurus          SRCHALATCINGEGNYSCVCPAGYLGDGRHCECSPGSCGPGLDCVREG--DALVCVDPCQ  177
Mus musculus        SNCHALATCVNTEGDYLCVCPEGFTGDGWYCECSPGSCEPGLDCLPQGPDGKLVCQDPCN  176
Rattus norvegicus   SNCHSLATCVNTEGSYSCVCPKGYRGDGWYCECSPGFCEPGLDCLPQGPSGKLVCQDPCN  178
                                                       ↑
                        *                   *                       *      *   *
Homo sapiens        AHRTLDEYWRSTEYGEGYACDTDLRGWYRFVGQGGARMAETCVPVLRCNTAAPMWLNGTH  235
Bos taurus          VHRILDEYWRSTEYGSGYICDVSLGGWYRFVGQAGVRLPETCVPVLHCNTAAPMWLNGTH  237
Mus musculus        TYETLTEYWRSTEYGVGYSCDAGLHGWYRFTGQGGVRMAETCVPVLRCNTAAPMWLNGSH  236
Rattus norvegicus   VYETLTEYWRSTDYGAGYSCDSDMHGWYRFTGQGGVRMAETCVPVLRCNTAAPMWLNGSH  238
                                                                ↑
                          *     **      *           *              *     *
Homo sapiens        PSSDEGIVSRKACAHWSGHCCLWDASVQVKACAGGYYVYNLTAPPECHLAYCTDPSSVEG  295
Bos taurus          PSSDEGIVNRVACAHWSGDCCLWDAPIQVKACAGGYYVYNLTAPPECHLAYCTDPSSVEG  297
Mus musculus        PSSSEGIVSRTACAHWSDQCCRWSTEIQVKACPGGFYIYNLTAPPECNLAYCTDPSSVEG  296
Rattus norvegicus   PSSREGIVSRTACAHWSDHCCLWSTEIQVKACPGGFYVYNLTEPPECNLAYCTDPSSVEG  298

*  *    *      * *                          *       *
Homo sapiens        TCEEECSIDEDCKSNNGRWHCQCKQDFNITDISLLEHRLECGANDMKVSLGKCQLKSLGFD  355
Bos taurus          TCEEECRVDEDCKSDNGEWHCQCKQDFNVTDLSLLERRLECGVDDIKLSLSKCQLKSLGFE  357
Mus musculus        TCEEECRVDEDCISDNGRWRCQCKQDSNITDVSQLEYRLECGANDIKMSLRKCQLQSLGFM  356
Rattus norvegicus   TCEEECGVDEDCVSDNGRWRCQCKQDFNVTDVSLLEHRLECEANEIKISLSKCQLQSLGFM  358

*                                        *
Homo sapiens        KVFMYLSDSRCSGFNDRDNRDWVSVVTPARDGPCGTVLTRNETHATYSNTLYLADEIIIR  415
Bos taurus          KVFMYLHDSQCSGFTERGDRDWMSVVTPARDGPCGTVMTRNETHATYSNTLYLADEIIIR  417
Mus musculus        NVFMYLNDRQCSGFSESDERDWMSIVTPARNGPCGTVLRRNETHATYSNTLYLANAIIIR  416
Rattus norvegicus   KVFMYLNDRQCSGFSERGERDWMSIVTPARDGPCGTVLRRNETHATYSNTLYLASEIIIR  418

*
Homo sapiens        DLNIKINFACSYPLDMKVSLKTALQPMVSALNIRVGGTGMFTVRMALFQTPSYTQPYQGS  475
Bos taurus          DLNIRINFACSYPLDMKVSLKTSLQPMVSALNISMGGTGTFTVRMALFQSPAYTQPYQGS  477
Mus musculus        DIIIRMNFECSYPLDMKVSLKTSLQPMVSALNISLGGTGKFTVRMALFQSPTYTQPHQGP  476
Rattus norvegicus   DINIRINFECSYPLDMKVSLKTSLQPMVSALNISLGGTGKFTVQMALFQNPTYTQPYQGP  478

*                                 *
Homo sapiens        SVTLSTEAFLYVGTMLDGGDLSRFALLMTNCYATPSSNATDPLKYFIIQDRCPHTRDSTI  535
Bos taurus          SVTLSTEAFLYVGTMLDGGDLSRFVLLMTNCYATPSSNATDPLKYFIIQDRCPRAADSTI  537
Mus musculus        SVMLSTEAFLYVGTMLDGGDLSRFVLLMTNCYATPSSNSTDPVKYFIIQDSCPRTEDTTI  536
Rattus norvegicus   SVMLSTEAFLYVGTMLDGGDLSRFVLLMTNCYATPSSNSTDPVKYFIIQDRCPHTEDTTI  538

*  *          *   *
Homo sapiens        QVVENGESSQGRFSVQMFRFAGNYDLVYLDCEVYLCDTMNEKCKPTCSGTRFRSGSVIDQ  595
Bos taurus          QVEENGESPQGRFSVQMFRFAGNYDLVYLHCEVYLCDTVNEKCRPTCPETRFRSGSIIDQ  597
Mus musculus        QVTENGESSQARFSVQMFRFAGNYDLVYLHCEVYLCDSTSEQCKPTCSGTRFRSGNFIDQ  596
Rattus norvegicus   QVTENGESSQARFSIQMFRFAGNSDLVYLHCEVYLCDTMSEQCKPTCSGTRYRSGNFIDQ  598

Homo sapiens        SRVLNLGPITRKGVQATVSRAF-SSLGLLKVWLPLLLSATLTLTFQ  640
Bos taurus          TRVLNLGPITRKGGQAAMSRAAPSSLGLLQVWLPLLLSATLTLMSP  643
Mus musculus        TRVLNLGPITRQGVQASVSKAASSNLRLLSIWLLLFPSATLIFMVQ  642
Rattus norvegicus   TRVLNLGPITRQGVQASVSKAASSNLGFLSIWLLLFLSATLTLMVH  644
```

FIG. 6

| | |
|---|---|
| SEQ ID NO:1 | TCCGTGTCAGGCGCACCGCACCCTGGA |
| SEQ ID NO:2 | CCGCCTGTCGCCCGGTCTCGGCTGCAC |
| SEQ ID NO:3 | ATGGATGGCACTGTGAGTGCTCCCC |
| SEQ ID NO:4 | ATGGCCGAGACCTGCGTGCCAGTC |
| SEQ ID NO:5 | TCCGTGTCAGGCGAGCAGCGAGTACGG |
| SEQ ID NO:6 | CCGCCTGTCGCCTGTCTCGGCTGCAC |
| SEQ ID NO:7 | TGGATGGCACTATGAGTGCTCCCC |
| SEQ ID NO:8 | ATGGCCGAGACCCGCGTGCCAGTC |

FIG. 7

SEQ ID NO:9

```
  1 mgqpsltwml mvvvaswfit taatdtsear wcsechsnat ctedeavttc tcqegftgdg
 61 ltcvdldeca ipgahncsan sscvntpgsf scvcpegfrl spglgctdvd ecaepglshc
121 halatcvnvv gsylcvcpag yrgdgwhcec spgscgpgld cvpegdalvc adpcqahrtl
181 deywrsteyg egyacdtdlr gwyrfvgqgg armaetcvpv lrcntaapmw lngthpssde
241 givsrkacah wsghcclwda svqvkacagg yyvynltapp echlayctdp ssvegtceec
301 sidedcksnn grwhcqckqd fnitdislle hrlecgandm kvslgkcqlk slgfdkvfmy
361 lsdsrcsgfn drdnrdwvsv vtpardgpcg tvltrnetha tysntlylad eiiirdlnik
421 infacsypld mkvslktalq pmvsalnirv ggtgmftvrm alfqtpsytq pyqgssvtls
481 teaflyvgtm ldggdlsrfa llmtncyatp ssnatdplky fiiqdrcpht rdstiqvven
541 gessqgrfsv qmfrfagnyd lvyldcevyl cdtmnekckp tcsgtrfrsg svidqsrvln
601 lgpitrkgvq atvsrafssl gllkvwlpll lsatltltfq
```

FIG. 8

SEQ ID NO:10

```
  1 mkclfspnfm wmaavvtswv iipaatdtss akscsechsn atctvdgaat tcacqegftg
 61 dglecvdlde cavlgahncs atkscvntlg sytcvcpegf llsselgced vdecaepgls
121 rchalatcin gegnyscvcp agylgdgrhc ecspgscgpg ldcvregdal vcvdpcqvhr
181 ildeywrste ygsgyicdvs lggwyrfvgq agvrlpetcv pvlhcntaap mwlngthpss
241 degivnrvac ahwsgdcclw dapiqvkaca ggyyvynlta ppechlayct dpssvegtce
301 ecrvdedcks dngewhcqck qdfnvtdlsl lerrlecgvd diklslskcq lkslgfekvf
361 mylhdsqcsg ftergdrdwm svvtpardgp cgtvmtrnet hatysntlyl adeiiirdln
421 irinfacsyp ldmkvslkts lqpmvsalni smggtgtftv rmalfqspay tqpyqgssvt
481 lsteaflyvg tmldggdlsr fvllmtncya tpssnatdpl kyfiiqdrcp raadstiqve
541 engespqgrf svqmfrfagn ydlvylhcev ylcdtvnekc rptcpetrfr sgsiidqtrv
601 lnlgpitrkg gqaamsraap sslgllqvwl plllsatltl msp
```

FIG. 9

SEQ ID NO:11

```
  1 mgipltwmll vmmvtswftl aeasnstear rcsechnnat ctvdgvvttc scqtgftgdg
 61 lvcedmdeca tpwthncsns scvntpgsfk cscqdgfrlt pelsctdvde cseqglsnch
121 alatcvnteg dylcvcpegf tgdgwycecs pgscepgldc lpqgpdgklv cqdpcntyet
181 lteywrstey gvgyscdagl hgwyrftgqg gvrmaetcvp vlrcntaapm wlngshpsss
241 egivsrtaca hwsdqccrws teiqvkacpg gfyiynltap pecnlayctd pssvegtcee
301 crvdedcisd ngrwrcqckq dsnitdvsql eyrlecgand ikmslrkcql qslgfmnvfm
361 ylndrqcsgf sesderdwms ivtparngpc gtvlrrneth atysntlyla naiiirdiii
421 rmnfecsypl dmkvslktsl qpmvsalnis lggtgkftvr malfqsptyt qphqgpsvml
481 steaflyvgt mldggdlsrf vllmtncyat pssnstdpvk yfiiqdscpr tedttiqvte
541 ngessqarfs vqmfrfagny dlvylhcevy lcdstseqck ptcsgtrfrs gnfidqtrvl
601 nlgpitrqgv qasvskaass nlrllsiwll lfpsatlifm vq
```

FIG. 10

SEQ ID NO:12

```
  1 mgqllsltwl llvmvvtpwf tvagandspe arrcsechdn atcvldgvvt tcscqagftg
 61 dglvcedide catpwthncs nsicmntlgs yecscqdgfr ltpglgcidv necteqglsn
121 chslatcvnt egsyscvcpk gyrgdgwyce cspgfcepgl dclpqgpsgk lvcqdpcnvy
181 etlteywrst dygagyscds dmhgwyrftg qggvrmaetc vpvlrcntaa pmwlngshps
241 sregivsrta cahwsdhccl wsteiqvkac pggfyvynlt eppecnlayc tdpssvegtc
301 eecgvdedcv sdngrwrcqc kqdfnvtdvs llehrlecea neikislskc qlqslgfmkv
361 fmylndrqcs gfsergerdw msivtpardg pcgtvlrrne thatysntly laseiiirdi
421 nirinfecsy pldmkvslkt slqpmvsaln islggtgkft vqmalfqnpt ytqpyqgpsv
481 mlsteaflyv gtmldggdls rfvllmtncy atpssnstdp vkyfiiqdrc phtedttiqv
541 tengessqar fsiqmfrfag nsdlvylhce vylcdtmseq ckptcsgtry rsgnfidqtr
601 vlnlgpitrq gvqasvskaa ssnlgflsiw lllflsatlt lmvh
```

FIG. 11

SEQ ID NO:13

```
   1 tcctgctcca aatgactgag ttcttcaaaa tgtgcaatgt gctgagaatt ggggagccaa
  61 gactgggatg ttggtgaggt aaggaggggg agtacaaggg gtaaagtccc agcaaaacaa
 121 gggctgcagt gttatgcaat tttttagtcc atataagtga cacctcctgg agttgtatac
 181 tatacaatca aagcactcct tccagctgtg gggaggagag ttagatcatg catttgtccc
 241 atccatctct gttcacagga caccagacat cagagacaga gagaaaaatt caaagggcca
 301 acccgtcttt cctttgggca ggtgctatct agacctgaag tagcgggaag agcagaaagg
 361 atggggcagc catctctgac ttggatgctg atggtggtgg tggcctcttg gttcatcaca
 421 actgcagcca ctgacacctc agaagcaagt aagtgaaaag tgtgtgtgcg ttgtatatgt
 481 gtgtatgcac gtgtatgtgt aatgtgtgg gggaagcaat gtagcacctg tcagaggtga
 541 tctcaatcct cctatcgcac ttgagacttg cattgtcttc attctaagtc catttcttag
 601 actcaatatg cacaggactg acttagaaat tttgctaaag tgcatattct ggttcagcag
 661 atctgcagta ggacctgaga tgctgaattt ttaacaagct tccaggcgat gctcatactg
 721 gggtcctgg agtacacatt gaaaagcaag gggctagaac atctctaagg cctgcaggcc
 781 ctttattgga agtcagaaac atactctatc acataggaga tttgaaccca tgcaggagga
 841 tccaaacacc ttccctttca actttaagag gtcattccat tgggttgaga tttgctgtca
 901 ccccactttc attttctccc tggagtacgt tggggcacga tgaatactat tgcggtgtcc
 961 tggttaaaag cacatatttt gtggtcctgc catctgcgtt tttatcctgg ttctacttct
1021 taccaaagga gtaaggggct taatccctct gaacctcagt ctcctcatct ttaaaataag
1081 gatacataaa aaactgacct cacgaggccc ttgggaagta ttcaacaaga tagtgagtga
1141 aaagtgcaca tcctattgcc tggcatatag taattgctta ataaacaaca gcttcttttt
1201 tttttaatg gttattttta ttacggagga acaaagtaca actgcccagc caggtggagt
1261 tggaggactc cgcagagagg aggcgacact gagcagggtc ctgatgaaga tttcaccagc
1321 caggaagca gaaaacataa aatgtgcaaa gaaagggagg ggcaacaggt tcaccgtaaa
1381 tcctaccaaa gtataggaat tctgcgcatt acttttctga atgtggctat tttaaaagaa
1441 gacagcttga aagcaatgct taacacaaaa aatgaatggt ggagctgggc gcgattgcac
1501 gtgcctgtgg tcccaacttt ttgggaagct gaggcagggt gcggtggtgg cttgaactca
1561 gggagtagaa cgcttgaacc caggaattgg aggctatggt gagctatgat cgcactactg
1621 cactccagcc tgggcgacag agcaagaccc ctctccaaaa aaataaataa agttaaaaaa
1681 tacaatgaaa taaacacaga atgaacggtg gaggcttgac atcatcagag gagttttgtt
1741 tctttgcttc tttccttgtt ttggagggag ccctctaggg aataagtctt aaaataatg
1801 agttccctgg agaatgaggg aaggatctct gggtggccat gggcccagct gcccaaaccc
1861 tgaagctggg cttttctgtc cacaggatgg tgctctgaat gtcacagcaa tgccacctgc
1921 acggaggatg aggccgttac gacgtgcacc tgtcaggagg gcttcaccgg cgatggcctg
1981 acctgcgtgg acctggatga gtgcgccatt cctggagctc acaactgctc cgccaacagc
2041 agctgcgtaa acacgccagg ctccttctcc tgcgtctgcc ccgaaggctt ccgcctgtcg
2101 cccgtctcg gctgcacaga cgtggatgag tgcgctgagc ctgggcttag ccactgccac
2161 gccctggcca catgtgtcaa tgtggtgggc agctacttgt gcgtatgccc cgcgggctac
2221 cggggggatg gatggcactg tgagtgctcc ccgggctcct gcgggccggg gttggactgc
2281 gtgcccgagg cgacgcgct cgtgtgcgcg gatccgtgtc aggcgcaccg caccctggac
2341 gagtactggc gcagcaccga gtacggggag ggctacgcct gcgacacgga cctgcgcggc
2401 tggtaccgct tcgtgggcca gggcggtgcg cgcatggccg agacctgcgt gccagtcctg
2461 cgctgcaaca cggccgcccc catgtggctc aatggcacgc atccgtccag cgacgagggc
2521 atcgtgagcc gcaaggcctg cgcgcactgg agcggccact gctgcctgtg ggatgcgtcc
2581 gtccaggtga aggcctgtgc cggcggctac tacgtctaca cctgacagc gccccccgag
2641 tgtcacctgg cgtactgcac aggtcagccg gagtctcccc acagtcctca tccaggcct
2701 ggaaaggcac tgcagaggac gggggtgcgt ccttattgat tgtctgtctg tccctgtgac
2761 cctgcagacc ccagctccgt ggaggggacg tgtgaggagt gcagtataga cgaggactgc
2821 aaatcgaata atggcagatg gcactgccag tgcaaacagg acttcaacat cactggtgag
2881 gccagtgggg aggaagcggg ttgttgagaa acctgtcact gcctggggga gggacacatt
2941 cctcccctgt gagattgggg ccatatgggt atgacgcagg ggatatatat ccaacctgag
3001 tgaaaacaga agatccacta atacccatta aagccggcaa gaggctctct gaggctccct
3061 gagtctccct ttagttgact tcaaagctgc caaagatttg ggaccttcct cgcacccagc
3121 cttctttctg aggcccacac cacagtgggc acccacgttg ctgccatctg ggagccaaag
3181 accatctgag ccctattcc
```

FIG. 12

SEQ ID NO:14

```
  1 acctctggac ctcaagtaat ctgtctgcct tggcctccca aagtgctagg attataggca
 61 tgagccaccg catctagcct ttttattttt ttaaacgagt attcattgtt atttaatgct
121 gggacatcaa aacccccaa aaccgtcctg catttggtat ataacccaca tttaggggaa
181 cccaagactg agtggttggt cagtggatgt atccattgat gtcagaggtc caatcttgag
241 tccccatcac attgggaggg gacagatcag ctcaaggcta tgctgagcac ttccagatgg
301 tggtcagccc agccagctgg acctggcccc tggggatgtg ctgggccccc aagctataga
361 cacacgtcct caatcccacc taacctgttt cagatatctc cctcctggag cacaggctgg
421 aatgtggggc caatgacatg aaggtgtcgc tgggcaagtg ccagctgaag agtctgggct
481 tcgacaaggt cttcatgtac ctgagtgaca gccggtgctc gggcttcaat gacagagaca
541 accgggactg ggtgtctgta gtgacccag cccgggatgg cccctgtggg acagtgttga
601 cggtacgtcc tggccagtgg gggacagaac cagagcactg cctggttcaa gtttcagctc
661 tatcacttcc tagttataga agctttgggg agttatttag cctggctgtg cctcagtttc
721 atcaactgta aagtggagaa ataatagtac ctactccaca ggtgtattga gaggattgaa
781 tgagttaatg tgttgaagtg attaggacag tgactgcaca cagtaagtgc tcaataaaca
841 tcagcttcaa ataaagaaag caattcatgg tgatagttct ccattttaca gatgggaaaa
901 gtagggccat agtagggatt gtctcagcca gtaggcatca
```

FIG. 13

SEQ ID NO:15

```
  1 accagcagat ttagctttga agtcctactc agattctcat gccccttcct ctcatcccca
 61 ccccccctcc accccccattc cctgcaacag aggaatgaaa cccatgccac ttacagcaac
121 accctctacc tggcagatga gatcatcatc cgtgacctca acatcaaaat caactttgca
181 tgctcctacc ccctggacat gaaagtcagc ctgaagaccg ccctacagcc aatggtcagg
241 tgtggccaga gagggtccct agggccccta gatggttcta accccaaacc ccttaaccat
301 gagcttccct gtcaactgcc acccacaggg agctgggagt gagggctggg aatcagggtt
361 gcccaatgga agagccagga attctggagc ccaggttcaa atctagactt tgtcataaat
421 gatggttatg ccctggccag tgggggacag agtcaaagca ctgcctggtt caagc
```

FIG. 14

SEQ ID NO:16

```
  1 agcagcatcc aggcacttgt cagaaatgca ggaccttgag ccccacccca atactcacca
 61 aatcagagcc tgcattttat ctagatccca agttgacctg cgtgtactta ttgcggtttg
121 caaagcaaca gttggtgggt tccactctta ttgctggata aaaatgcaaa caactgcaag
181 ggactgccta ggaatgcaaa tcagagaagg tggcctatct gcagatgttc tcagcccggt
241 cctctcacca acccttctcc cctggcagtg ctctaaacat cagagtgggc gggaccggca
301 tgttcaccgt gcggatggcg ctcttccaga ccccttccta cacgcagccc taccaaggct
361 cctccgtgac actgtccact gaggcttttc tctacgtggg caccatgttg gatggggcg
421 acctgtcccg atttgcactg ctcatgacca actgctatgc cacacccagt agcaatgcca
481 cggaccccct gaagtacttc atcatccagg acaggtaagg caaaggttcc tacatgggaa
541 ctcatgggta gaattcagag ggggtctttg gacttggatg gaggaaaatt gcatcttttt
601 tttttttttt tttgacagag tcttgctctg tcgccaaggt tggagtgcaa tggtgtgacc
661 tcggctcact gcaacctccg cctcctgggt tcaagtgatt cttctgcctc a
```

FIG. 15

SEQ ID NO:17

```
   1 atttgaatcc aggaagtctg actccagaat ctttatttaa ccaaccacat taaatgatgt
  61 gtaaccctcc cagatgccca cacactagag actcaactat ccaagtggtg gagaatgggg
 121 agtcctccca gggccgattt tccgtccaga tgttccggtt tgctggaaac tatgacctag
 181 tctacctgca ctgtgaagtc tatctctgtg acaccatgaa tgaaaagtgc aagcctgtga
 241 gttgactccc ctcccccagc ccatctcttg taaccaaaga catttggcca caaagaaaac
 301 aaatcaatat ttcttccctg tttccctctt ttaccagagg gatagaatga gcaataagat
 361 gaggtgggcg tggctaggca ggaaacctaa gctgcagggg aaatcaggtg ggatcagtaa
 421 agtgcggcag gctggtaaga gctctggctt atctgcaagc ttgtgttcaa ataacaggag
 481 ctgacatttt taagcactgt gcccacttta tttgtgttag cttttaatgc ttcacagcaa
 541 ctctataagg gaggtattac tggttccctt tcctcatgag gagagggct cagagaactt
 601 cagtggcttg cctgagatca tgcatctatc taacaaatgg cagagctggg acctgcacga
 661 gccccggtat acaggtctcc taacaacttc tgcctggggc aagggaaggc acctgtgagg
 721 tgggcagtcc actccacgtg gcagaaccac attcaggctc cttcatggag ggtgttttc
 781 tattgccctc tccctgtaga cctgctctgg gaccagattc cgaagtggga gtgtcataga
 841 tcaatcccgt gtcctgaact tgggtcccat cacacggaaa ggtaagagag ccactcgctc
 901 ctcaacattc ctggctggga aagatttctg gagaggaaga gggataacag agcctggcac
 961 cttggcacct tactgagctc tgaagaactg ggagcaagtg gatcctctgg ggcaaggtgg
1021 aatacagact gccttccttt cactattccc attcatacac ccattcattg gacaaatatg
1081 atttgtagat gaatgtaaca caggacacgg g
```

FIG. 16

SEQ ID NO:18

```
  1 gagcccctga tgggtctgaa gtaggggagt aacatgatca gatttgggtt ttgaagagat
 61 cagtctggct gcgaagtgaa aagtagattg aaggggtttc tgtcaggatg cttgccaaat
121 ctcatgcatt ctttattcac tgatccttct gttttcctcc aaaggtgtcc aggccacagt
181 ctcaagggct tttagcagct tgggtaagtt caggtccttt ctgcagtggg acctgttcca
241 gaactctcct gggggcttc tatctgttaa cttgtaatgc ttcatagcaa ctctataagg
301 gaggtgttac tagttccgtt ttctaaataa ggagagtggc tcaga
```

FIG. 17

SEQ ID NO:19

```
  1 tagattgggc acttcacaag aatgcccttt gcccttttga ggaggtacca agcctagtgc
 61 cggaggaaag attatctttt tcaaatcggt ccaccttttt cagggcagat aaggaggaag
121 cttccttttt ctaggagagc agcccagaga gggtgtcctc ttctgattgg tcagcctaga
181 cgaggcagct tatgttaatt tgcacaaaag tacagcagta ctagcagttg ccctgtcact
241 gttttctttt cagggctcct gaaagtctgg ctgcctctgc ttctctcggc caccttgacc
301 ctgactttc agtgactgac agcggaaagc cctgtgctcc atggctgcca tctcacctcc
361 tgctgggcag ggggcatgat gcgggccagt gctccagcca cagaaaagaa agttcatgct
421 ttgttcagcc tgccttcttt tctccctttt aatcctggct gtcgagaaac agcctgtgtc
481 tttaaatgct gcttttctc aaaatgggac ttgtgacggt gtacctgagg cccccatctc
541 cttaaagagt gtggcaaaat aatgattttt aaatctcagt ctttgaagtc atccattcat
601 tcaacaagta tttactgaac tctaccatgt aggcactatg tatggtgcta aggatcctac
661 ggtgggaaaa ataacccccc cacactgtcc tcatggagtt cacagtctgc tcagtgagac
721 tgggttctgc tgt
```

FIG. 18

SEQ ID NO:20

```
   1 gcggccgcgg gagctgcggg gagcgcgggg gcggcccgga gcgtgccggg gtccccgcgc
  61 ctcgctcgcc ggccgcgctc cgaagatggt ggcggcgccg tgcgcccgga ggctggcccg
 121 gcgctcgcac tcggcgctgc tcgcggcgct cacggtgctg ctgctgcaga cgctggtcgt
 181 gtggaatttc agcagcctcg actccggggc cggggagcgc cgcgggggcg cagcggtcgg
 241 cggcggggag cagccgcccc cggccccggc cccgcgccgg gagcgccggg acctgcccgc
 301 cgagccggct gcagcccgag gaggaggagg aggcggcggc ggaggaggag gaggacggg
 361 gccccaggcg cgggcgcggg gaggcggccc cggagaaccg cggggacagc agccgccag
 421 ccgggggca ctgcccgccc gggctctgga tccacaccca agtccgctca tcaccctgga
 481 gactcaggat ggctactttt ctcatcgcc gaaagagaaa gtgcgaacag acagcaacaa
 541 cgagaactct gtccccaaag actttgagaa tgtggacaac agcaacttcg cacccaggac
 601 tcaaaagcag aagcaccagc ctgagttggc gaagaagcca ccgagtagac agaaggagct
 661 tttgaaaagg aagctggaac agcaggagaa aggaaaggca catacattcc ctgggaaagg
 721 ccccggtgag gtgctgcctc ccggggacag agccgcagcc aacagcagcc acgggaagga
 781 tgtgtccaga ccgcctcatg ccaggaaaac tgggggcagc tcccccgaga ccaagtatga
 841 ccagcccct aagtgtgaca tctcaggcaa ggaggccatc tctgccctgt cccgtgctaa
 901 gtccaagcac tgccgccagg agattgggga gacttactgc cgccacaagt tagggctgct
 961 gatgcctgag aaggtgactc ggttctgccc cctcgagggt aaagccaaca agaacgtgca
1021 gtgggacgag gactccgtgg agtacatgcc agccaacccg gtcagaatcg cctttgtcct
1081 ggtggtccac ggccgtgcct ctcggcagtt gcagcgcatg ttcaaggcca tctaccacaa
1141 agaccacttc tactacatcc acgtggacaa gcgctctaat tacctgcatc ggcaagtgct
1201 ccaggtctcc aggcagtaca gcaatgtccg cgtcaccccc tggagaatgg ccaccatctg
1261 gggaggagcc agcctcctgt ccacctacct gcagagcatg cgggacctcc tggagatgac
1321 cgactggccc tgggacttct tcatcaaccct gagtgcggac gactacccca tcaggacaaa
1381 tgaccagttg gtggcgtttc tctcccgata ccgagatatg aatttcttga agtcacacgg
1441 ccgggacaat gcaaggttca ttcggaagca gggcctggat cggctcttcc tggagtgcga
1501 cgctcacatg tgcgcctgg gagatcggcg gatcccagag ggcattgccg tggatggcgg
1561 ttcggactgg ttcctgctga accggaggtt tgtagaatat gtgaccttct ccacagacga
1621 tctggtgacc aagatgaaac agttctactc ctacaccctg cttcctgctg agtccttctt
1681 ccatacggtc ctggagaaca gcccccactg cgacaccatg gtggacaaca acctgcgcat
1741 caccaactgg aatcgcaagc tgggctgcaa gtgccagtac aagcacatcg tggactggtg
1801 cggctgctcc cccaatgact tcaagccgca ggacttccac cgcttccagc agacagcccg
1861 gcctaccttc tttgcccgca gtttgaagc cgtggtgaat caggaaatca ttggcagct
1921 ggactattac ctgtacggga actaccctgc aggtacccg ggcctgcgct cctactggga
1981 gaatgtctac gatgagcctg acggcatcca cagcctgacc gacgtgacac tcaccttgta
2041 ccactccttt gcccgcctgg gtcttcgacg ggccgagacg tccctgcaca cggatgggga
2101 gaacagctgc cgatactacc caatgggcca cccagcatct gtgcacctct acttccttgc
2161 tgaccgcttc cagggctttc tgatcaagca tcatgctacc aatctggctg tgagcaaact
2221 agagactctg gagacctggg tgatgccgaa aaaagtcttc aagatcgcaa gcccacccag
2281 tgactttggg aggcttcagt tttccgaggt cggcactgac tgggatgcca aggagaggct
2341 attccgcaac tttgggggtc ttctggggcc catgatgag ccggtgggta tgcagaagtg
2401 ggggaaggga cctaatgtga ccgtgaccgt catttgggtg gatcccgtca atgtcatcgc
2461 agccacctac gacatcctca ttgagtccac tgccgaattc acacactaca gccccctttt
2521 gaacttgccc ctgaggcctg gggtctggac agtgaaaatt ctccaccact gggtgccagt
2581 tgcagagacc aaattcctcg ttgcgcctct gaccttctcg aacaggcagc ccatcaaacc
2641 tgaggaggca ctgaagctgc acaatgcatg cctccgcaat gcctacatga agcagagctt
2701 ccagagccta aaccccgtcc tcagcctgcc catcaaccc gccaggtgg aacaggcacg
2761 gaggaacgca gcctccacgg gcacagcgct ggagggatgg ctggactcgt tggtgggcgg
2821 gatgtggact gccatggaca tctgtgccac gggccccaca gcctgccggg tcatgcagac
2881 ctgcagccag acggcctgga gctccttcag ccctgacccc aagtcggagc tgggggcagt
2941 caaacctgat ggccggctca ggtagccatg ggcacgagga gtgggccaca gcaggatctc
3001 aacgggaaag cagccagagg ggttgtgggg cctgaacccc ggcctccac cctggggag
3061 gccctctgtg aatgggtctc tcctggccat agaatgatgg aaaggggagg tcagcaggtc
3121 aaagcaggat cagccaacaa cctgccttg gcaagctgcg ggtgggatgg ctcagtccct
3181 gcactgtgac tgtctcacct cttctggtta atcctcaagt cctacaggtt ccttgtcttc
3241 cccttccagt gacccacccc tgacccccaga cgtgtgattt tcagacttt ctttcgagca
3301 gcagaacttc gtttacggag cacagtcata agtgggtt cagggtgctg acgaaatcca
3361 agctgctctg gttgaagctg acaagtgcga ggttccctcc caaagctcag ccctctgggc
3421 ggtccccttg cccagggtat ctcctacggt acctcttcag aacccaaggg ctctgcaaat
3481 gccagtttga caagcactgc ccagaccaac catgggttca aactccagcc ctgcccttg
3541 gttcattttt ctgcttctct tggctggggg actctggtgc cagccttgaa agtcatggtc
3601 gtggggccct tcccatggag gctgcagcct taggagagct ctgagcctct cagcagccct
3661 ccttgggttg aactattctc cttagtaact aggtaagtgg gaaagccttt tgatgtggca
3721 tggccaaggt ccagccacaa gtgcaactgc cacctgtcca gggtctgggg cctccttcc
3781 tcaaggctgc cacacaaagt agcagaaata ggatgatgtt tgtgagcacc agactcaaga
3841 ccatgacctt cttgatcct tgaaatggg aactttgaca gccatgacca tgaaactcac
3901 aaggcaacgc gatgaaactc acaaagcaat gcttggagca aaactcctga gctagacagc
3961 acagcagcac ccatcccctg ccagagccct tccgttcgtga ggtcagacac acaaaaccctt
4021 cgtcaattgc acaccggtgc tgttgggagt gaccaaacca catgaaccag acttttcccg
4081 tccaggaaat agcatttcag atttggtttt taattcatg cccttcggcc acaggctcaa
4141 cgggacatgc aacataaaaa tgggaaggtt atttaaac
```

FIG. 19

SEQ ID NO:21

```
   1 gccaagggca ctattggcca gttccgttca acgaagtggt tgcttttttt agttccggca
  61 atgagttgcg ccggggcggc ggcggctccc cgcctttggc ggctgcgccc gggggcccgg
 121 cggtccctct cagcttatgg aagaagaacc agtgtcagat ttcgcagttc aggaatgact
 181 ttagacaata tcagtcgggc agctgtggat cgaataatcc gggtggatca tgcaggcgaa
 241 tatggagcaa accgcatcta tgccgggcag atggctgtcc tgggtcggac cagcgtcggg
 301 ccagtcattc agaaaatgtg ggatcaagaa aaggaccatt tgaaaaagtt caatgagttg
 361 atggttacgt tcagggtccg gccaacagtt ctgatgccct tgtggaacgt gctggggttt
 421 gcactggggg cggggaccgc cttgctcggg aaggaaggtg ccatggcctg caccgtggcg
 481 gtggaagaga gcatagcaca tcactacaac aaccagatca ggacgctgat ggaggaggac
 541 cctgaaaaat acgaggaact tcttcagctg ataaagaaat tcgggatga agagcttgag
 601 caccatgaca taggcctcga ccatgatgca gaattggctc agcctatgc cgtcctgaag
 661 agcattatcc aggccggatg cagagtggcg atatatttat cagaaagatt ataaagtgtg
 721 tccagttttg cctgtctata aagatgata gtaatttacc aagtgacatt tgcagagaaa
 781 caggtgtaca gttatcgttg tactttgta caatgtgaat tttgttaata aattataagg
 841 tttgttttt ttttttaaa ctctgcagtg ttgattttc tctgggttgt ttttctgcc
 901 atgagaccaa caggtcacca gccttgttca agttacagca acgaagctg ggccttgttt
 961 ggtctcatac ttaattttct tttatataca tgtttttctt ttacatgcat atatatatat
1021 tttatttat tttatgtttt ttggagacag ggcctcgctc ttttgtccag gccgggtcac
1081 aactcactgc agcctggacc tctagcctc aagcaatcca cccacctcag ccttccaagt
1141 agctgggact acaggtgtgc accaccacag ctggctaatt ctatttttt atagaggcga
1201 agtctcacta tgtcgccagg ctggtctcta actcctgggc tcagtgatcc tcccgtttcg
1261 acttcccaaa gtgctgggat tacaggtgtg agccacttca ccaggcccat tttctcctaa
1321 aacttcaagg acaaatcatt aataatgtaa caggaatctt taggagaaaa aacaatttgg
1381 tttactgata acaaagata attggaaaca tgagagtatt tgagattggc caagcagaac
1441 tatgaagtcc atcaagtaag tcaaagatca tcgtttctgt tttgaattgt gggtgataat
1501 gggtgggaga gtgctacagt ctgtatgtct gtgtctccct agaattcata cgatgaaatc
1561 ttcactctca agttgataga aggtggggcc cttgggaagt gtgaggtcat gagagtggag
1621 ccctcatgaa tgggatcagt gccttatgaa aggccctaga gagatacctc atcctctcca
1681 cagtgtgaga cttcaagggg aagtatgaga cttctctgag gaagcagacc cttcacaagc
1741 aaaatcagcc agcactttga tcacggactt cccagcctct aggactgtga gcaataaatg
1801 tttgatgttt ataagccacc cagactgtgg tattttgtta tagcagcctg aacagactaa
1861 gacggggtg ttgcttccat caaaggatgt actaagttgt ggattatttg tgaaattgaa
1921 ttacaacctt ttccttaagg tcttttacca cctccccccc aaaaaaatcc cccaaaactg
1981 attcagattt tcatacttta atgaaatatt ttataatttg caaattttta agtaatttat
2041 gaaaaaccta gatcagtgga tctcctctct ggctgcccat tagaatgtcc tgtggagatt
2101 aaacttttt ttttcagttt atggaccaag agttttgatt tatttagggt ggagttcagg
2161 atcagaatgg tttcagaagc tccaggtga ttccggagtg agttggagct gcaagcccct
2221 gagctagatt ataagatgct tctgggaaag aaccacattt taggaatttg cttcccaccc
2281 agtgccctgc atttaatcag cacctgatga cttggcagga cttgccccac cagggtctgg
2341 ctttgaaggg tagtggacac caggatcctt tggattaatc ctctgccacc tctctctttt
2401 cctcaaccga gagtgaattt atgtaattga gtgaaagtct acgaatcata attgtaataa
2461 attaaggctg ggcatttgtt tgaaattaga taggataaag ccaaaggttt gaacaagttg
2521 tggatggttt gtaaaaatta atcttacaaa ataaatgctg tgtgtgaaca cgttgattaa
2581 attcaaaaaa a
```

FIG. 20

SEQ ID NO:22

```
   1 gttaagggct ccgtggacat ctcaggtctt cagggtcttc catctggaac tatataaagt
  61 tcagaaaaca tgtctcgaag atatgactcc aggaccacta tattttctcc agaaggtcgc
 121 ttataccaag ttgaatatgc catggaagct attggacatg caggcacctg tttgggaatt
 181 ttagcaaatg atggtgtttt gcttgcagca gagagacgca acatccacaa gcttcttgat
 241 gaagtctttt tttctgaaaa aatttataaa ctcaatgagg acatggcttg cagtgtggca
 301 ggcataactt ctgatgctaa tgttctgact aatgaactaa ggctcattgc tcaaaggtat
 361 ttattacagt atcaggagcc aataccttgt gagcagttgg ttacagcgct gtgtgatatc
 421 aaacaagctt atacacaatt tggaggaaaa cgtccctttg gtgtttcatt gctgtacatt
 481 ggctgggata agcactatgg ctttcagctc tatcagagtg accctagtgg aaattacggg
 541 ggatggaagg ccacatgcat tggaaataat agcgctgcag ctgtgtcaat gttgaaacaa
 601 gactataaag aaggagaaat gaccttgaag tcagcacttg ctttagctat caaagtacta
 661 aataagacca tggatgttag taaactctct gctgaaaaag tggaaattgc aacactaaca
 721 agagagaatg gaaagacagt aatcagagtt ctcaaacaaa aagaagtgga gcagttgatc
 781 aaaaaacacg aggaagaaga agccaaagct gagcgtgaga agaaagaaaa agaacagaaa
 841 gaaaaggata aatagaatca gagattttat tactcatttg gggcaccatt tcagtgtaaa
 901 agcagtccta ctcttccaca ctaggaaggc tttactttttt ttaactggtg cagtgggaaa
 961 ataggacatt acatactgaa ttgggtcctt gtcatttctg tccaattgaa tactttattg
1021 taacgatgat ggttacccct catggacgtc ttaatcttcc acacacatcc cctttttttg
1081 gaataaaatt tggaaaatgg aaatgaaaaa aaaaaaaaa aaaaaaaaa aaaaaaaaa
1141 a
```

FIG. 21

SEQ ID NO:23

```
   1 aggtcgcagg cgggcgtgcg tggagcgggg gccgcggccg cgccgcagag atgtgactcg
  61 ggccgaaggc cagctggagc gtcggcgctg cggggccgcg ggggtcgaat gttcgtggca
 121 tcagagagaa agatgagagc tcaccaggtg ctcaccttcc tctgctctt cgtgatcacc
 181 tcggtggcct ctgaaaacgc cagcacatcc cgaggctgtg ggctggacct cctccctcag
 241 tacgtgtccc tgtgcgacct ggacgccatc tggggcattg tggtggaggc ggtggccggg
 301 gcgggcgccc tgatcacact gctcctgatg ctcatcctcc tggtgcggct gcccttcatc
 361 aaggagaagg agaagaagag ccctgtgggc ctccactttc tgttcctcct ggggaccctg
 421 ggcctctttg ggctgacgtt tgccttcatc atccaggagg acgagaccat ctgctctgtc
 481 cgccgcttcc tctggggcgt cctctttgcg ctctgcttct cctgcctgct gagccaggca
 541 tggcgcgtgc ggaggctggt gcggcatggc acgggccccg cgggctggca gctggtgggc
 601 ctggcgctgt gcctgatgct ggtgcaagtc atcatcgctg tggagtggct ggtgctcacc
 661 gtgctgcgtg acacaaggcc agcctgcgcc tacgagccca tggactttgt gatggccctc
 721 atctacgaca tggtactgct tgtggtcacc ctggggctgg ccctcttcac tctgtgcggc
 781 aagttcaaga ggtggaagct gaacgggccc ttcctcctca tcacagcctt cctctctgtg
 841 ctcatctggg tggcctggat gaccatgtac ctcttcggca atgtcaagct gcagcagggg
 901 gatgcctgga acgaccccac cttggccatc acgctggcgg ccagcggctg ggtcttcgtc
 961 atcttccacg ccatccctga gatccactgc acccttctgc cagccctgca ggagaacacg
1021 cccaactact tcgacacgtc gcagcccagg atgcgggaga cggccttcga ggaggacgtg
1081 cagctgccgc gggcctatat ggagaacaag gccttctcca tggatgaaca caatgcagct
1141 ctccgaacag caggatttcc caacggcagc ttgggaaaaa gacccagtgg cagcttgggg
1201 aaaagaccca gcgctccgtt tagaagcaac gtgtatcagc caactgagat ggccgtcgtg
1261 ctcaacggtg ggaccatccc aactgctccg ccaagtcaca caggaagaca cctttggtga
1321 aagactttaa gttccagaga atcagaattt ctcttaccga tttgcctccc tggctgtgtc
1381 tttcttgagg gagaaatcgg taacagttgc cgaaccaggc cgcctcacag ccaggaaatt
1441 tggaaatcct agccaagggg atttcgtgta aatgtgaaca ctgacgaact gaaaagctaa
1501 caccgactgc ccgcccctcc cctgccacac acacagacac gtaataccag accaacctca
1561 atccccgcaa actaaagcaa agctaattgc aaatagtatt aggctcactg aaaatgtgg
1621 ctgggaagac tgtttcatcc tctgggggta aacagaacc aaattcacag ctggtgggcc
1681 agactggtgt tggttggagg tgggggctc ccactcttat cacctctccc agcaagtgc
1741 tggaccccag gtagcctctt ggagatgacc gttgcgttga ggacaaatgg ggactttgcc
1801 accggcttgc ctggtggttt gcacatttca gggggtcag gagagttaag gaggttgtgg
1861 gtgggattcc aaggtgaggc ccaactgaat cgtggggtga gctttatagc cagtagaggt
1921 ggagggaccc tggcatgtgc caaagaagag gccctctggg tgatgaagtg accatcacat
1981 ttggaaagtg atcaaccact gttccttcta tggggctctt gctctaatgt ctatggtgag
2041 aacacaggcc ccgccccttc ccttgtagag ccatagaaat attctggctt ggggcagcag
2101 tcccttcttc ccttgatcat ctcgccctgt tcctacactt acgggtgtat ctccaaatcc
2161 tctcccaatt ttattccctt attcatttca agagctccaa tggggtctcc agctgaaagc
2221 ccctccggga ggcaggttgg aaggcaggca ccacggcagg ttttccgcga tgatgtcacc
2281 tagcagggct tcaggggttc ccactaggat gcagagatga cctctcgctg cctcacaagc
2341 agtgacacct cgggtccttt ccgttgctat ggtgaaaatt cctggatgga atggatcaca
2401 tgagggtttc ttgttgcttt tggagggtgt ggggatatt ttgttttggt ttttctgcag
2461 gttccatgaa acagcccttt tccaagccc attgtttctg tcatggtttc catctgtcct
2521 gagcaagtca ttcctttgtt atttagcatt tcgaacatct cggccattca aagcccccat
2581 gttctctgca ctgtttggcc agcataacct ctagcatcga ttcaaagcag agttttaacc
2641 tgacggcatg gaatgtataa atgagggtgg gtccttctgc agatactcta atcactacat
2701 tgcttttcct ataaaactac ccataagcct ttaaccttta agaaaaatg aaaaggtta
2761 gtgtttgggg gccgggggag gactgaccgc ttcataagcc agtacgtctg agctgagtat
2821 gtttcaataa accttttgat atttctcaaa aaaaaaaaaa aaaaaaaaa
```

FIG. 22

SEQ ID NO:24

```
   1 attcccatgg ctggccagag gaggaacgct ttgtgttctc atcggagctg catgggaagt
  61 ctgcatacag caaagtgacc tgcatgcctc accttatgga aaggatggtg ggctctggcc
 121 tcctgtggct ggccttggtc tcctgcattc tgacccaggc atctgcagtg cagcgaggtt
 181 atggaaaccc cattgaagcc agttcgtatg ggctggacct ggactgcgga gctcctggca
 241 ccccagaggc tcatgtctgt tttgacccct gtcagaatta cccctcctg atgaaccct
 301 tccgaagcac agagaactca gcagggtccc aggggtgcga taaaaacatg agcggctggt
 361 accgctttgt aggggaagga ggagtaagga tgtcggagac ctgtgtccag gtgcaccgat
 421 gccagacaga cgctcccatg tggctgaatg ggacccaccc tgcccttggg gatggcatca
 481 ccaaccacac tgcctgtgcc cattggagtg caactgctg tttctggaaa acagaggtgc
 541 tggtgaaggc ctgcccaggc gggtaccatg tgtaccggtt ggaaggcact ccctggtgta
 601 atctgagata ctgcacagtt ccacgagacc catccactgt ggaggacaag tgtgagaagg
 661 cctgccgccc cgaggaggag tgccttgccc tcaacagcac ctggggctgt ttctgcagac
 721 aggacctcaa tagttctgat gtccacagtt tgcagcctca gctagactgt gggcccaggg
 781 agatcaaggt gaaggtggac aaatgtttgc tgggaggcct gggtttgggg gaggaggtca
 841 ttgcctacct gcgagaccca aactgcagca gcatcttgca gacagaggag aggaactggg
 901 tatctgtgac cagccccgtc caggctagtg cctgcaggaa cattctggag agaaatcaaa
 961 cccatgccat ctacaaaaac ccctctcct tggtcaatga tttcatcatc agagacacca
1021 tcctcaacat caacttccaa tgtgcctacc cactggacat gaaagtcagc ctccaagctg
1081 ccttgcagcc cattgtaagt tccctgaacg tcagtgtgga cgggaatgga gagttcattg
1141 tcaggatggc cctcttccaa gaccagaact acacgaatcc ttacgaaggg gatgcagttg
1201 aactgtctgt tgagtccgtg ctgtatgtgg gtgccatctt ggaacaaggg gacacctccc
1261 ggtttaacct ggtgttgagg aactgctatg ccacccccac tgaagacaag gctgaccttg
1321 tgaagtattt catcatcaga aacagctgct caaatcaacg tgattccacc atccacgtgg
1381 aggagaatgg gcagtcctcg gaaagccggt tctcagttca gatgttcatg tttgctggac
1441 attatgacct agttttcctg cattgtgaga ttcatctctg tgattctctt aatgaacagt
1501 gccagccttc ttgctcaaga agtcaagtcc gcagtgaagt accggccatc gacctagccc
1561 gggttctaga tttggggccc atcactcgga gaggtgcaca gtctcccggt gtcatgaatg
1621 gaaccccctag cactgcaggg ttcctggtgg cctggcctat ggtcctcctg actgtcctcc
1681 tggcttggct gttctgagag ctccgctgag catctggcct tgaagtttgt gttcttccct
1741 ctggcaatgg ctcccttcag cacttctgct ttccactcca attcacacag gcttggtatt
1801 aacagaatca aggccaggct aggttaggaa aagggaagag ctttcacctt ctttaaaact
1861 ctcggctggg cgcagtggct catgcctgta atcccagcat tttgggaggc tgaggcaggt
1921 ggatcacctg aggtcagcag ttcaaaatca gcctggccaa aatgctgaaa ctccgtctct
1981 actaaaaata caaaaattag ccaggcatgg tggcaggcgc ctgtaatccc agctactcgg
2041 gaggccaagg caggagaatt gctcgaactc agggggtgga ggttgcagtg agttgagatt
2101 gtgccattgc actccagcct gggcaacaga gcaagactct gtctcaggaa aaaaaaaaa
2161 aaaaagaaa agcaacatag tggggtttct gtcaatctgt cctcggctgc ccttctcatt
2221 tgttgatggg accttgaaag caagcttgct aggtgccctc tgtggctcca gcctttaccg
2281 gaagtgtggt gcatgttttt aacttcaggg aagcggtatc ctgtcactgg ggtatgggat
2341 gagcatggag aagaggcacc agccacgatt ccttcctaag catctcctgt tctgactgct
2401 catgaattga agaaactgac ccttgtgttc aaaaaaaaaa aaaaaaa
```

FIG. 23

SEQ ID NO:25

```
   1 agactaactc tacctttctg gcttcaggtg ctatctagac ctgaagtagc gggaagagca
  61 gaaaggatgg ggcagccatc tctgacttgg atgctgatgg tggtggtggc ctcttggttc
 121 atcacaactg cagccactga cacctcagaa gcaagatggt gctctgaatg tcacagcaat
 181 gccacctgca cggaggatga ggccgttacg acgtgcacct gtcaggaggg cttcaccggc
 241 gatggcctga cctgcgtgga cctggatgag tgcgccattc ctggagctca caactgctcc
 301 gccaacagca gctgcgtaaa cacgccaggc tccttctcct gcgtctgccc cgaaggcttc
 361 cgcctgtcgc ccggtctcgg ctgcacagac gtggatgagt gcgctgagcc tgggcttagc
 421 cactgccacg ccctggccac atgtgtcaat gtggtgggca gctacttgtg cgtatgcccc
 481 gcgggctacc gggggatgg atggcactgt gagtgctccc cgggctcctg cgggccgggg
 541 ttggactgcg tgcccgaggg cgacgcgctc gtgtgcgcgg atccgtgcca ggcgcaccgc
 601 accctggacg agtactggcg cagcaccgag tacggggagg gctacgcctg cgacacggac
 661 ctgcgcggct ggtaccgctt cgtgggccag ggcggtgcgc catggccga gacctgcgtg
 721 ccagtcctgc gctgcaacac ggccgccccc atgtggctca atggcacgca tccgtccagc
 781 gacgagggca tcgtgagccg caaggcctgc gcgcactgga cggccactg ctgcctgtgg
 841 gatgcgtccg tccaggtgaa ggcctgtgcc ggcggctact acgtctacaa cctgacagcg
 901 ccccccgagt gtcacctggc gtactgcaca gaccccagct ccgtggaggg gacgtgtgag
 961 gagtgcagta tagacgagga ctgcaaatcg aataatggca gatggcactg ccagtgcaaa
1021 caggacttca acatcactga tatctccctc ctggagcaca ggctggaatg tgggccaat
1081 gacatgaagg tgtcgctggg caagtgccag ctgaagagtc tgggcttcga caaggtcttc
1141 atgtacctga gtgacagccg gtgctcgggc ttcaatgaca gagacaaccg ggactgggtg
1201 tctgtagtga ccccagcccg ggatggcccc tgtgggacag tgttgacgag gaatgaaacc
1261 catgccactt acagcaacac cctctacctg gcagatgaga tcatcatccg tgacctcaac
1321 atcaaaatca actttgcatg ctcctacccc ctggacatga agtcagcct gaagaccgcc
1381 ctacagccaa tggtcagtgc tctaaacatc agagtgggcg ggaccggcat gttcaccgtg
1441 cggatggcgc tcttccagac cccttcctac acgcagcct accaaggctc ctccgtgaca
1501 ctgtccactg aggcttttct ctacgtgggc accatgttgg atggggcga cctgtcccga
1561 tttgcactgc tcatgaccaa ctgctatgcc acacccagta gcaatgccac ggaccccctg
1621 aagtacttca tcatccagga cagatgccca cacactagag actcaactat ccaagtggtg
1681 gagaatgggg agtcctccca gggccgattt tccgtccaga tgttccggtt tgctggaaac
1741 tatgacctag tctacctgca ctgtgaagtc tatctctgtg acaccatgaa tgaaaagtgc
1801 aagcctacct gctctgggac cagattccga agtgggagtg tcatagatca atcccgtgtc
1861 ctgaacttgg gtcccatcac acggaaaggt gtccaggcca cagtctcaag ggctttagc
1921 agcttggggc tcctgaaagt ctggctgcct ctgcttctct cggccacctt gaccctgact
1981 tttcagtgac tgacagcgga aagccctgtg ctccatggct gccatctcac ctcctgctgg
2041 gcaggggca tgatgcgggc cagtgctcca gccacagaaa agaaagttca tgctttgttc
2101 agcctgcctt cttttctccc ttttaatcct ggctgtcgag aaacagcctg tgtctttaaa
2161 tgctgctttt tctcaaaatg ggacttgtga cggtgtacct gaggccccca tctccttaaa
2221 gagtgtggca aataatgat ttttaaatct caaaaaaaaa aaaa
```

FIG. 24

SEQ ID NO:26

```
   1 agccatctct tcccaaggca ggtggtgact tgagaactct gtgcctggtt tctgaggact
  61 gtttcaccat gcagtggcta atgaggttcc ggaccctctg gggcatccac aaatccttcc
 121 acaacatcca ccctgcccct tcacagctgc gctgccggtc tttatcagaa tttggagccc
 181 caagatggaa tgactatgaa gtaccggagg aatttaactt tgcaagttat gtactggact
 241 actgggctca aaaggagaag gagggcaaga gaggtccaaa tccagctttt tggtgggtga
 301 atggccaagg ggatgaagta aagtggagct tcagagagat gggagaccta acccgccgtg
 361 tagccaacgt cttcacacag acctgtggcc tacaacaggg agaccatctg gccttgatgc
 421 tgcctcgagt tcctgagtgg tggctggtgg ctgtgggctg catgcgaaca gggatcatct
 481 tcattcctgc gaccatcctg ttgaaggcca agacattct ctatcgacta cagttgtcta
 541 aagccaaggg cattgtgacc atagatgccc ttgcctcaga ggtggactcc atagcttctc
 601 agtgcccctc tctgaaaacc aagctcctgg tgtctgatca cagccgtgaa gggtggctgg
 661 acttccgatc gctggttaaa tcagcatccc agaacacac ctgtgttaag tcaaagacct
 721 tggacccaat ggtcatcttc ttcaccagtg ggaccacagg cttccccaag atggcaaaac
 781 actcccatgg gttggcctta caaccctcct tcccaggaag taggaaatta cggagcctga
 841 agacatctga tgtctcctgg tgcctgtcgg actcaggatg gattgtggct accatttgga
 901 ccctggtaga accatggaca gcgggttgta cagtctttat ccaccatctg ccacagtttg
 961 acaccaaggt catcatacag acattgttga ataccccat taaccacttt tgggggtat
1021 catctatata tcgaatgatt ctgcagcagg atttcaccag catcaggttc cctgccctgg
1081 agcactgcta tactggcggg gaggtcgtgt tgcccaagga tcaggaggag tggaaaagac
1141 ggacgggcct tctgctctac gagaactatg ggcagtcgga aacgggacta atttgtgcca
1201 cctactgggg aatgaagatc aagccgggtt tcatggggaa ggccactcca ccctatgacg
1261 tccaggtcat tgatgacaag ggcagcatcc tgccacctaa cacagaagga aacattggca
1321 tcagaatcaa acctgtcagg cctgtgagcc tcttcatgtg ctatgagggt gacccagaga
1381 agacagctaa agtggaatgt ggggacttct acaacactgg ggacagagga agatggatg
1441 aagagggcta catttgtttc ctggggagga gtgatgacat cattaatgcc tctgggtatc
1501 gcatcgggcc tgcagaggtt gaaagcgctt tggtggagca cccagcggtg gcggagtcag
1561 ccgtggtggg cagcccagac ccgattcgag gggaggtggt gaaggccttt attgtcctga
1621 ccccacagtt cctgtcccat gacaaggatc agctgaccaa ggaactgcag cagcatgtca
1681 agtcagtgac agccccatac aagtacccaa ggaacgtgga gtttgtctca gagctgccaa
1741 aaaccatcac tggcaagatt gaacggaagg aacttcggaa aaaggagact ggtcagatgt
1801 aatcggcagt gaactcagaa cgcactgcac acctaaggca aatccctggc cactttagtc
1861 tccccactat ggtgaggacg agggtggggc attgagagtg ttgatttggg aaagtatcag
1921 gagtgccata atcactagtg aattc
```

FIG. 25

SEQ ID NO:27

```
  1 atggagaacc aaaacaatgt gacagaattt atccttctgg gactcacaga gaacccaaag
 61 atgcaaaaaa ttgtattcat tatgtttttt cttatctaca tcatttctat aacaggaaat
121 gtgctcattg tggtcaccat aacttctacg tcattattag agtcccccat gtacttttc
181 ctggcttatc tatcctttat tgatgcttgc tattcctctg ttagcacccc taaactgata
241 gcagattcac tctgtgaaaa gaagaccatc ccatttaatg gatgcatgac tcagatcttt
301 ggggagcatt tgtttggagg tgctgaaatc atcctgctga cagtaatggc ctatgaccgc
361 tatgtggcca tctgcaaacc ccttcattat gcaacgatca tgagtcgaag actatgtagc
421 ctgctagtgg gagtgtcatg gctaggaggt tttcttcatg ccaccataca gatcctgttc
481 attttccaat tacccttctg tggccctaac atcatagatc attttatgtg tgatcttaat
541 cctttgctca accttgtatg caccgatact cacactcttg gaatctttgt tgcagccaac
601 agtggtttta tttgtctgct aaacttcctt cttctattgg tctcctatgt tgccatcctg
661 cgctccctaa agaaccacag tgcagaggga aggcgcaaag ccctctctac ctgtatttca
721 cacataacag tggttgtctt attctttgtg ccttgcatat ttgtatacat gagacctgta
781 gctaccttac ccattgataa agcagttgct atgttctata ctatgataac tcccatgttg
841 aacccctta tctatacctt aagaaatgct cagatgaaag atgccattaa gaaatgggt
901 agcactaaaa ttctttcaag taataaatga
```

FIG. 26

SEQ ID NO:28

```
   1 gccaagggca ctattggcca gttccgttca acgaagtggt tgcttttttt agttccggca
  61 atgagttgcg ccggggcggc ggcggctccc cgcctttggc ggctgcgccc ggggccccgg
 121 cggtccctct cagcttatgg aagaagaacc agtgtcagat ttcgcagttc aggaatgact
 181 ttagacaata tcagtcgggc agctgtggat cgaataatcc gggtggatca tgcaggcgaa
 241 tatggagcaa accgcatcta tgccgggcag atggctgtcc tgggtcggac cagcgtcggg
 301 ccagtcattc agaaaatgtg ggatcaagaa aaggaccatt tgaaaaagtt caatgagttg
 361 atggttacgt tcagggtccg gccaacagtt ctgatgccct tgtggaacgt gctggggttt
 421 gcactggggg cggggaccgc cttgctcggg aaggaaggtg ccatggcctg caccgtggcg
 481 gtggaagaga gcatagcaca tcactacaac aaccagatca ggacgctgat ggaggaggac
 541 cctgaaaaat acgaggaact tcttcagctg ataaagaaat tcgggatga agagcttgag
 601 caccatgaca taggcctcga ccatgatgca gaattggctc agcctatgc cgtcctgaag
 661 agcattatcc aggccggatg cagagtggcg atatatttat cagaaagatt ataaagtgtg
 721 tccagttttg cctgtctata aagatgata gtaatttacc aagtgacatt tgcagagaaa
 781 caggtgtaca gttatcgttg tacttttgta caatgtgaat tttgttaata aattataagg
 841 tttgtttttt tttttttaaa ctctgcagtg ttgatttttc tctgggttgt ttttctgcc
 901 atgagaccaa caggtcacca gccttgttca agttacagca aacgaagctg ggccttgttt
 961 ggtctcatac ttaattttct tttatataca tgtttttctt ttacatgcat atatatatat
1021 tttattttat tttatgtttt ttggagacag ggcctcgctc ttttgtccag gccgggtcac
1081 aactcactgc agcctggacc tcctagcctc aagcaatcca cccacctcag ccttccaagt
1141 agctgggact acaggtgtgc accaccacag ctggctaatt ctatttttt atagaggcga
1201 agtctcacta tgtcgccagg ctggtctcta actcctgggc tcagtgatcc tccgtttcg
1261 acttcccaaa gtgctgggat tacaggtgtg agccacttca ccaggcccat tttctcctaa
1321 aacttcaagg acaaatcatt aataatgtaa caggaatctt taggagaaaa aacaatttgg
1381 tttactgata acaaagata attggaaaca tgagtatt tgagattggc caagcagaac
1441 tatgaagtcc atcaagtaag tcaaagatca tcgtttctgt tttgaattgt gggtgataat
1501 gggtgggaga gtgctacagt ctgtatgtct gtgtctccct agaattcata cgatgaaatc
1561 ttcactctca agttgataga aggtggggcc cttgggaagt gtgaggtcat gagagtggag
1621 ccctcatgaa tgggatcagt gccttatgaa aggccctaga gagatacctc atcctctcca
1681 cagtgtgaga cttcaagggg aagtatgaga cttctctgag gaagcagacc cttcacaagc
1741 aaaatcagcc agcactttga tcacggactt cccagcctct aggactgtga gcaataaatg
1801 tttgatgttt ataagccacc cagactgtgg tattttgtta tagcagcctg aacagactaa
1861 gacgggggtg ttgcttccat caaaggatgt actaagttgt ggattatttg tgaaattgaa
1921 ttacaacctt ttccttaagg tcttttacca cctcccccc aaaaaaatcc cccaaaactg
1981 attcagattt tcatacttta atgaaatatt ttataatttg caattttta agtaatttat
2041 gaaaaaccta gatcagtgga tctcctctct ggctgcccat tagaatgtcc tgtggagatt
2101 aaactttttt ttttcagttt atggaccaag agttttgatt tatttagggt ggagttcagg
2161 atcagaatgg tttcagaagc tcccaggtga ttccggagtg agttggagct gcaagcccct
2221 gagctagatt ataagatgct tctgggaaag aaccacattt taggaatttg cttcccaccc
2281 agtgccctgc atttaatcag cacctgatga cttggcagga cttgccccac cagggtctgg
2341 ctttgaaggg tagtggacac caggatcctt tggattaatc ctctgccacc tctctctttt
2401 cctcaaccga gagtgaattt atgtaattga gtgaaagtct acgaatcata attgtaataa
2461 attaaggctg ggcatttgtt tgaaattaga taggataaag ccaaggtttt gaacaagttg
2521 tggatggttt gtaaaaatta atcttacaaa ataaatgctg tgtgtgaaca cgttgattaa
2581 attcaaaaaa a
```

FIG. 27

SEQ ID NO:29

```
   1 cccaggcgcc ccggccttat tccagcctgg ggagcgcctc ggtggggagc acgggacagc
  61 gagggaggcc gaggcggggg ccctgggcgc ccgatatctc cgaaccgggg aggcggcccc
 121 gattccgaga gccggaacgc agggaaaggc aaggacgggg cggccggcgg aggggcgggc
 181 gccgctcatc agccacgcca gtcacgtctg gggccaccgg ctgccttttt cttcctttcc
 241 ccctttgctt tcttccccct ccgctgttgg cgagggcaaa gtggccgtgg cggcgccatg
 301 cccgggccgg agtgagtgcg cgcgggcgaa aatggcgtac atccagttgg aaccattaaa
 361 cgagggtttt ctttctagaa tctctggtct gctgctgtgc agatggacct gccggcactg
 421 ctgtcagaag tgctacgagt ccagctgttg ccagtcaagt gaggatgaag ttgaaattct
 481 gggacctttc cctgctcaga cccctccctg gctgatggcc agccggagca gtgacaagga
 541 tggtgactct gtccacacgg ccagcgaagt cccgctgacc ccacggacca attccccgga
 601 tggaagacgc tcgtcctcag acacatccaa gtctacatac agcctgacgc ggaggatttc
 661 gagtcttgag tcaagacgtc ccagctctcc actcatcgat attaaaccca tcgagtttgg
 721 cgttctcagc gccaagaagg agcccatcca accttcggtg ctcagacgga cctataaccc
 781 cgacgactat ttcaggaagt tcgaacccca cctgtactcc ctcgactcca cagcgacga
 841 tgtggactct ctgacagacg aggagatcct gtccaagtac cagctgggca tgctgcactt
 901 cagcactcag tacgacctgc tgcacaacca cctcaccgtg cgcgtgatcg aggccaggga
 961 cctgccacct cccatctccc acgatggctc gcgccaggac atggcgcact ccaaccccta
1021 cgtcaagatc tgtctcctgc cagaccagaa gaactcaaag cagaccgggg tcaaacgcaa
1081 gacccagaag cccgtgtttg aggagcgcta caccttcgag atccccttcc tggaggccca
1141 gaggaggacc ctgctcctga ccgtggtgga ttttgataag ttctcccgcc actgtgtcat
1201 tgggaaagtt tctgtgcctt tgtgtgaagt tgacctggtc aagggcgggc actggtggaa
1261 ggcgctgatt cccagttctc agaatgaagt ggagctgggg gagctgcttc tgtcactgaa
1321 ttatctccca agtgctggca gactgaatgt tgatgtcatt cgagccaagc aacttcttca
1381 gacagatgtg agccaaggtt cagacccctt tgtgaaaatc cagctggtgc atggactcaa
1441 acttgtgaaa accaagaaga cgtccttctt aagggcaca attgatcctt tctacaatga
1501 atccttcagc ttcaaagttc cccaagaaga actggaaaat gccagcctag tgtttacagt
1561 tttcggccac aacatgaaga gcagcaatga cttcatcggg aggatcgtca ttggccagta
1621 ctcttcaggc ccctctgaga ccaaccactg gaggcgcatg ctcaacacgc accgcacagc
1681 cgtggagcag tggcatagcc tgaggtcccg agctgagtgt gaccgcgtgt ctcctgcctc
1741 cctggaggtg acctgagggc tgcagggaag gcagctttca tttgtttaaa aaaaaaaaa
1801 aaagacggaa aaaatgtgt cacatactat tacatccaca cctgcataca cactcgcaac
1861 atgtctacac acgtccacac acacagacac acagataccc caaatcctct ca
```

FIG. 28

SEQ ID NO:30

```
   1 atgcaaaggt ggacactgtg ggctgcagcc ttcctgaccc tccactctgc acaggccttt
  61 ccacaaacag acatcagtat cagtccagcc ctgccagagc tgcccctgcc ttccctgtgc
 121 cccctgttct ggatggagtt caaaggccac tgctatcgat tcttccctct caataagacc
 181 tgggctgagg ccgacctcta ctgttctgag ttctctgtgg gcaggaagtc cgccaagctg
 241 gcctccatcc acagctggga ggagaatgtc tttgtatatg acctcgtgaa cagctgtgtt
 301 cccggcatcc cagctgacgt ctggacaggc cttcatgatc acagacagga agggcagttt
 361 gaatggactg atggctcatc ctatgactac agctactggg atggcagcca gccagatgat
 421 ggcgtccacg cggacccaga agaaggagac tgcgtgcaga tatggtacag cctaccagt
 481 gagcagctac aggccccaga gccccagtta cccttatcaa tctcagaggc cacagatgtc
 541 tatctccctg aggatttccc agctgagccc aagctcatgg accagtcctg ggtgtccagg
 601 aagagcctga accatccaa gagtcatctt atggagccac ccactccagt ggccaagcac
 661 caaaaggcaa agacccgaca taggagcctg cgcggcgtct ggtggccatc aggtaaggct
 721 gggtcatgga agaaagaat gaatgcagac tacgggcgaa gaaagcgatc ggccccgagg
 781 caggaaggcc ggctccggtg cagggagcgc cgcctgcggg ctgcttcggg ccagggtcga
 841 cccgagggcc agcgcaagca gcggcaacag gagcgccagg agagaggctg ggaagaactg
 901 ggaggggtgt ccccaatgcg gggcgcccaa gcgtggcagc acgggctggg agcggggagc
 961 cagcggggtg cggcgccgga gtgcggggag aaccaccagg cgccggaatt ggggagcacg
1021 tggaggggc agcggctcca gccccagacc gccgcgctct gtcactttgc attaagaaag
1081 cttccgggga atgcacacgg cctggccgcc gccttcgtgc agcccgccct gcaggtgcag
1141 gaagaaaaga ataatcgcac ccgtttctca ggtgcttact tcaccatgtc cgatccgacg
1201 tgtgaccaag atagcaagga gcagtcttta aggcgacacg gcagagaggc agaaaaagat
1261 gggccttacc ggttagttaa gaaaaaaaga ggacctgttg cctgtccctc tagctttgaa
1321 ctacaaagtg gagggaagt ttgtctggat tttcctgtag aactgagggc agggacctgg
1381 attgctcgag aacctccata a
```

FIG. 29

SEQ ID NO:31

```
   1 aggtcgcagg cgggcgtgcg tggagcgggg gccgcggccg cgccgcagag atgtgactcg
  61 ggccgaaggc cagctggagc gtcggcgctg cggggccgcg ggggtcgaat gttcgtggca
 121 tcagagagaa agatgagagc tcaccaggtg ctcaccttcc tcctgctctt cgtgatcacc
 181 tcggtggcct ctgaaaacgc cagcacatcc cgaggctgtg ggctggacct cctccctcag
 241 tacgtgtccc tgtgcgacct ggacgccatc tgggggcattg tggtggaggc ggtggccggg
 301 gcgggcgccc tgatcacact gctcctgatg ctcatcctcc tggtgcggct gcccttcatc
 361 aaggagaagg agaagaagag ccctgtgggc ctccactttc tgttcctcct ggggaccctg
 421 ggcctctttg ggctgacgtt tgccttcatc atccaggagg acgagaccat ctgctctgtc
 481 cgccgcttcc tctggggcgt cctctttgcg ctctgcttct cctgcctgct gagccaggca
 541 tggcgcgtgc ggaggctggt gcggcatggc acgggccccg cgggctggca gctggtgggc
 601 ctggcgctgt gcctgatgct ggtgcaagtc atcatcgctg tggagtggct ggtgctcacc
 661 gtgctgcgtg acacaaggcc agcctgcgcc tacgagccca tggactttgt gatggccctc
 721 atctacgaca tggtactgct tgtggtcacc ctggggctgg ccctcttcac tctgtgcggc
 781 aagttcaaga ggtggaagct gaacggggcc ttcctcctca tcacagcctt cctctctgtg
 841 ctcatctggg tggcctggat gaccatgtac ctcttcggca atgtcaagct gcagcagggg
 901 gatgcctgga acgaccccac cttggccatc acgctggcgg ccagcggctg ggtcttcgtc
 961 atcttccacg ccatccctga gatccactgc accttctgc cagccctgca ggagaacacg
1021 cccaactact tcgacacgtc gcagcccagg atgcgggaga cggccttcga ggaggacgtg
1081 cagctgccgc gggcctatat ggagaacaag gccttctcca tggatgaaca caatgcagct
1141 ctccgaacag caggatttcc caacggcagc ttgggaaaaa gacccagtgg cagcttgggg
1201 aaaagaccca gcgctccgtt tagaagcaac gtgtatcagc caactgagat ggccgtcgtg
1261 ctcaacggtg ggaccatccc aactgctccg ccaagtcaca caggaagaca cctttggtga
1321 aagactttaa gttccagaga atcagaattt ctcttaccga tttgcctccc tggctgtgtc
1381 tttcttgagg gagaaatcgg taacagttgc cgaaccaggc cgcctcacag ccaggaaatt
1441 tggaaatcct agccaagggg atttcgtgta aatgtgaaca ctgacgaact gaaaagctaa
1501 caccgactgc ccgcccctcc cctgccacac acacagacac gtaataccag accaacctca
1561 atccccgcaa actaaagcaa agctaattgc aaatagtatt aggctcactg aaaatgtgg
1621 ctgggaagac tgtttcatcc tctggggta gaacagaacc aaattcacag ctggtgggcc
1681 agactggtgt tggttggagg tgggggggctc ccactcttat cacctctccc cagcaagtgc
1741 tggaccccag gtagcctctt ggagatgacc gttgcgttga ggacaaatgg ggactttgcc
1801 accggcttgc ctggtggttt gcacatttca gggggggtcag gagagttaag gaggttgtgg
1861 gtgggattcc aaggtgaggc ccaactgaat cgtggggtga gctttatagc cagtagaggt
1921 ggagggaccc tggcatgtgc caaagaagag gccctctggg tgatgaagtg accatcacat
1981 ttggaaaagtg atcaaccact gttccttcta tggggctctt gctctaatgt ctatggtgag
2041 aacacaggcc ccgccccttc ccttgtagag ccatagaaat attctggctt ggggcagcag
2101 tcccttcttc ccttgatcat ctcgccctgt tcctacactt acgggtgtat ctccaaatcc
2161 tctcccaatt ttattccctt attcatttca agagctccaa tggggtctcc agctgaaagc
2221 ccctccggga ggcaggttgg aaggcaggca ccacggcagg ttttccgcga tgatgtcacc
2281 tagcagggct tcaggggttc ccactaggat gcagagatga cctctcgctg cctcacaagc
2341 agtgacacct cgggtccttt ccgttgctat ggtgaaaatt cctggatgga atggatcaca
2401 tgagggtttc ttgttgcttt tggagggtgt gggggatatt ttgttttggt ttttctgcag
2461 gttccatgaa aacagccctt ttccaagccc attgtttctg tcatggtttc catctgtcct
2521 gagcaagtca ttcctttgtt atttagcatt tcgaacatct cggccattca aagcccccat
2581 gttctctgca ctgtttggcc agcataacct ctagcatcga ttcaaagcag agtttttaacc
2641 tgacggcatg gaatgtataa atgagggtgg gtccttctgc agatactcta atcactacat
2701 tgctttttct ataaaactac ccataagcct ttaacctttta aagaaaaatg aaaaaggtta
2761 gtgtttgggg gccggggag gactgaccgc ttcataagcc agtacgtctg agctgagtat
2821 gtttcaataa accttttgat atttctcaaa aaaaaaaaa aaaaaaaaa
```

FIG. 30

SEQ ID NO:32

```
   1 attcccatgg ctggccagag gaggaacgct ttgtgttctc atcggagctg catgggaagt
  61 ctgcatacag caaagtgacc tgcatgcctc accttatgga aaggatggtg ggctctggcc
 121 tcctgtggct ggccttggtc tcctgcattc tgacccaggc atctgcagtg cagcgaggtt
 181 atggaaaccc cattgaagcc agttcgtatg ggctggacct ggactgcgga gctcctggca
 241 ccccagaggc tcatgtctgt tttgacccct gtcagaatta caccctcctg gatgaacccT
 301 tccgaagcac agagaactca gcagggtccc aggggtgcga taaaaacatg agcggctggt
 361 accgctttgt aggggaagga ggagtaagga tgtcggagac ctgtgtccag gtgcaccgat
 421 gccagacaga cgctcccatg tggctgaatg ggacccaccc tgcccttggg gatggcatca
 481 ccaaccacac tgcctgtgcc cattggagtg gcaactgctg tttctggaaa acagaggtgc
 541 tggtgaaggc ctgcccaggc gggtaccatg tgtaccggtt ggaaggcact ccctggtgta
 601 atctgagata ctgcacagac ccatccactg tggaggacaa gtgtgagaag gcctgccgcc
 661 ccgaggagga gtgccttgcc ctcaacagca cctggggctg tttctgcaga caggacctca
 721 atagttctga tgtccacagt ttgcagcctc agctagactg tgggcccagg agatcaagg
 781 tgaaggtgga caaatgtttg ctgggaggcc tgggtttggg ggaggaggtc attgcctacc
 841 tgcgagaccc aaactgcagc agcatcttgc agacagagga gaggactgg gtatctgtga
 901 ccagccccgt ccaggctagt gcctgcagga acattctgga gagaaatcaa acccatgcca
 961 tctacaaaaa caccctctcc ttggtcaatg atttcatcat cagagacacc atcctcaaca
1021 tcaacttcca atgtgcctac ccactggaca tgaaagtcag cctccaagct gccttgcagc
1081 ccattgtaag ttccctgaac gtcagtgtgg acgggaatgg agagttcatt gtcaggatgg
1141 ccctcttcca agaccagaac tacacgaatc cttacgaagg ggatgcagtt gaactgtctg
1201 ttgagtccgt gctgtatgtg ggtgccatct ggaacaagg ggacacctcc cggtttaacc
1261 tggtgttgag gaactgctat gccacccccA ctgaagacaa ggctgacctt gtgaagtatt
1321 tcatcatcag aaacagctgc tcaaatcaac gtgattccac catccacgtg gaggagaatg
1381 ggcagtcctc ggaaagccgg ttctcagttc agatgttcat gtttgctgga cattatgacc
1441 tagttttcct gcattgtgag attcatctct gtgattctct taatgaacag tgccagcctt
1501 cttgctcaag aagtcaagtc cgcagtgaag taccggccat cgacctagcc cgggttctag
1561 atttggggcc catcactcgg agaggtgcac agtctcccgg tgtcatgaat ggaacccta
1621 gcactgcagg gttcctggtg cctggccta tggtcctcct gactgtcctc ctggcttggc
1681 tgttctgaga gctccgctga gcatctggcc ttgaagtttg tgttcttccc tctggcaatg
1741 gctcccttca gcacttctgc tttccactcc aattcacaca ggcttggtat taacagaatc
1801 aaggccaggc taggttagga aaagggaaga gctttcacct tcttttaaaac tctcggctgg
1861 gcgcagtggc tcatgcctgt aatcccagca ttttgggagg ctgaggcagg tggatcacct
1921 gaggtcagca gttcaaaatc agcctggcca aaatgctgaa actccgtgtc tactaaaaat
1981 acaaaaatta gccaggcatg gtggcaggcg cctgtaatcc cagctactcg ggaggccaag
2041 gcaggagaat tgctcgaact caggggtgg aggttgcagt gagttgagat tgtgccattg
2101 cactccagcc tgggcaacag agcaagactc tgtctcagga aaaaaaaaaa aaaaaagaa
2161 aagcaacata gtggggtttc tgtcaatctg tcctcggctg ccCttctcat ttgttgatgg
2221 gaccttgaaa gcaagcttgc taggtgccct ctgtggctcc agcctttacc ggaagtgtgg
2281 tgcatgtttt taacttcagg gaagcggtat cctgtcactg gggtatggga tgagcatgga
2341 gaagaggcac cagccacgat tccttcctaa gcatctcctg ttctgactgc tcatgaattg
2401 aagaaactga cccttgtgtt caaaaaaaaa aaaaaaaaa
```

FIG. 31

SEQ ID NO:33

```
   1 agactaactc tacctttctg gcttcaggac accagacatc agagacagag agaaaaattc
  61 aaagggccaa cccgtctttc ctttgggcag gtgctatcta gacctgaagt agcgggaaga
 121 gcagaaagga tggggcagcc atctctgact tggatgctga tggtggtggt ggcctcttgg
 181 ttcatcacaa ctgcagccac tgacacctca gaagcaagat ggtgctctga atgtcacagc
 241 aatgccacct gcacggagga tgaggccgtt acgacgtgca cctgtcagga gggcttcacc
 301 ggcgatggcc tgacctgcgt ggacctggat gagtgcgcca ttcctggagc tcacaactgc
 361 tccgccaaca gcagctgcgt aaacacgcca ggctccttct cctgcgtctg ccccgaaggc
 421 ttccgcctgt cgcccggtct cggctgcaca gacgtggatg agtgcgctga gcctgggctt
 481 agccactgcc acgccctggc cacatgtgtc aatgtggtgg gcagctactt gtgcgtatgc
 541 cccgcgggct accgggggga tggatggcac tgtgagtgct ccccgggctc ctgcgggccg
 601 gggttggact gcgtgcccga gggcgacgcg ctcgtgtgcg cggatccgtg ccaggcgcac
 661 cgcaccctgg acgagtactg gcgcagcacc gagtacgggg agggctacgc ctgcgacacg
 721 gacctgcgcg gctggtaccg cttcgtgggc cagggcggtg cgcgcatggc cgagacctgc
 781 gtgccagtcc tgcgctgcaa cacggccgcc cccatgtggc tcaatggcac gcatccgtcc
 841 agcgacgagg gcatcgtgag ccgcaaggcc tgcgcgcact ggagcggcca ctgctgcctg
 901 tgggatgcgt ccgtccaggt gaaggcctgt gccggcggct actacgtcta caacctgaca
 961 gcgcccccg agtgtcacct ggcgtactgc acagacccca gctccgtgga ggggacgtgt
1021 gaggagtgca gtatagacga ggactgcaaa tcgaataatg gcagatggca ctgccagtgc
1081 aaacaggact tcaacatcac tgatatctcc ctcctggagc acaggctgga atgtggggcc
1141 aatgacatga aggtgtcgct gggcaagtgc cagctgaaga gtctgggctt cgacaaggtc
1201 ttcatgtacc tgagtgacag ccggtgctcg ggcttcaatg acagagacaa ccgggactgg
1261 gtgtctgtag tgacccccagc ccgggatggc ccctgtggga cagtgttgac gaggaatgaa
1321 acccatgcca cttacagcaa caccctctac ctggcagatg agatcatcat ccgtgacctc
1381 aacatcaaaa tcaactttgc atgctcctac ccctggaca tgaaagtcag cctgaagacc
1441 gccctacagc caatggtcag tgctctaaac atcagagtgg gcgggaccgg catgttcacc
1501 gtgcggatgg cgctcttcca gacccttcc tacacgcagc cctaccaagg ctcctccgtg
1561 acactgtcca ctgaggcttt tctctacgtg ggcaccatgt tggatggggg cgacctgtcc
1621 cgatttgcac tgctcatgac caactgctat gccacaccca gtagcaatgc cacggacccc
1681 ctgaagtact tcatcatcca ggacagatgc ccacacta gagactcaac tatccaagtg
1741 gtggagaatg gggagtcctc ccagggccga ttttccgtcc agatgttccg gtttgctgga
1801 aactatgacc tagtctacct gcactgtgaa gtctatctct gtgacaccat gaatgaaaag
1861 tgcaagccta cctgctctgg gaccagattc cgaagtggga gtgtcataga tcaatcccgt
1921 gtcctgaact gggtcccat cacacggaaa ggtgtccagg ccacagtctc aagggctttt
1981 agcagcttgg ggctcctgaa agtctggctg cctctgcttc tctcggccac cttgaccctg
2041 acttttcagt gactgacagc ggaaagccct gtgctccatg gctgccatct cacctcctgc
2101 tgggcagggg gcatgatgcg ggccagtgct ccagccacag aaaagaaagt tcatgctttg
2161 ttcagcctgc cttcttttct cccttttaat cctggctgtc gagaaacagc ctgtgtcttt
2221 aaatgctgct ttttctcaaa atgggacttg tgacggtgta cctgaggccc ccatctcctt
2281 aaagagtgtg gcaaaataat gatttttaaa tctcaaaaaa aaaaaaa
```

FIG. 32

SEQ ID NO:34

```
   1 agccatctct tcccaaggca ggtggtgact tgagaactct gtgcctggtt tctgaggact
  61 gtttcaccat gcagtggcta atgaggttcc ggaccctctg gggcatccac aaatccttcc
 121 acaacatcca ccctgcccct tcacagctgc gctgccggtc tttatcagaa tttggagccc
 181 caagatggaa tgactatgaa gtaccggagg aatttaactt tgcaagttat gtactggact
 241 actgggctca aaaggagaag gagggcaaga gaggtccaaa tccagctttt tggtgggtga
 301 atggccaagg ggatgaagta aagtggagct tcagagagat gggagaccta acccgccgtg
 361 tagccaacgt cttcacacag acctgtggcc tacaacaggg agaccatctg gccttgatgc
 421 tgcctcgagt tcctgagtgg tggctggtgg ctgtgggctg catgcgaaca gggatcatct
 481 tcattcctgc gaccatcctg ttgaaggcca agacattct ctatcgacta cagttgtcta
 541 aagccaaggg cattgtgacc atagatgccc ttgcctcaga ggtggactcc atagcttctc
 601 agtgcccctc tctgaaaacc aagctcctgg tgtctgatca cagccgtgaa gggtggctgg
 661 acttccgatc gctggttaaa tcagcatccc cagaacacac ctgtgttaag tcaaagacct
 721 tggacccaat ggtcatcttc ttcaccagtg ggaccacagg cttccccaag atggcaaaac
 781 actcccatgg gttggcctta caaccctcct tcccaggaag taggaaatta cggagcctga
 841 agacatctga tgtctcctgg tgcctgtcgg actcaggatg gattgtggct accatttgga
 901 ccctggtaga accatggaca gcgggttgta cagtctttat ccaccatctg ccacagtttg
 961 acaccaaggt catcatacag acattgttga ataccccat taaccacttt tgggggggtat
1021 catctatata tcgaatgatt ctgcagcagg atttcaccag catcaggttc cctgccctgg
1081 agcactgcta tactggcggg gaggtcgtgt gcccaagga tcaggaggag tggaaaagac
1141 ggacgggcct tctgctctac gagaactatg ggcagtcgga acgggacta atttgtgcca
1201 cctactgggg aatgaagatc aagccgggtt tcatggggaa ggccactcca ccctatgacg
1261 tccaggtcat tgatgacaag ggcagcatcc tgccacctaa cacagaagga aacattggca
1321 tcagaatcaa acctgtcagg cctgtgagcc tcttcatgtg ctatgaggt gacccagaga
1381 agacagctaa agtggaatgt ggggacttct acaacactgg ggacagagga agatggatg
1441 aagagggcta catttgtttc ctggggagga gtgatgacat cattaatgcc tctgggtatc
1501 gcatcgggcc tgcagaggtt gaaagcgctt tggtggagca cccagcggtg gcggagtcag
1561 ccgtggtggg cagcccagac ccgattcgag gggaggtggt gaaggccttt attgtcctga
1621 ccccacagtt cctgtcccat gacaaggatc agctgaccaa ggaactgcag cagcatgtca
1681 agtcagtgac agccccatac aagtacccaa ggaacgtgga gtttgtctca gagctgccaa
1741 aaaccatcac tggcaagatt gaacggaagg aacttcggaa aaggagact ggtcagatgt
1801 aatcggcagt gaactcagaa cgcactgcac acctaaggca aatccctggc cactttagtc
1861 tccccactat ggtgaggacg agggtggggc attgagagtg ttgatttggg aaagtatcag
1921 gagtgccata atcactagtg aattc
```

FIG. 33

| | |
|---|---|
| SEQ ID NO:35 | TCCTGCTCCAAATGACTGAGTTCT |
| SEQ ID NO:36 | TCAACCCAATGGAATGACCTCTTA |
| SEQ ID NO:37 | GGTGGAGGCTTGACATCATCAGAG |
| SEQ ID NO:38 | GGAATAGGGCTCAGATGGTCTTTG |
| SEQ ID NO:39 | GCCCTGGCCTCATGTGTCAATGTG |
| SEQ ID NO:40 | GGGTCACAGGGACAGACAGACAAT |
| SEQ ID NO:41 | CGGCGGCTACTACGTCTACAACCT |
| SEQ ID NO:42 | GTAGCTGCCCACCACATTGACACA |
| SEQ ID NO:43 | ACCTCTGGACCTCAAGTAATCTGT |
| SEQ ID NO:44 | TGATGCCTACTGGCTGAGACAATC |
| SEQ ID NO:45 | ACCAGCAGATTTAGCTTTGAAGTC |
| SEQ ID NO:46 | GCTTGAACCAGGCAGTGCTTTGACc |
| SEQ ID NO:47 | AGCAGCATCCAGGCACTTGTCAGA |
| SEQ ID NO:48 | TGAGGCAGAAGAATCACTTGAACC |
| SEQ ID NO:49 | TCCAAAGACCCCCTCTGAATTCTA |
| SEQ ID NO:50 | ATTTGAATCCAGGAAGTCTGACTC |
| SEQ ID NO:51 | GGCAAGCCACTGAAGTTCTCTGAG |
| SEQ ID NO:52 | GAGCGGCTCAGAGAACTTCAGTGG |
| SEQ ID NO:53 | CCCGTGTCCTGTGTTACATTCATC |
| SEQ ID NO:54 | GAGCCCTGATGGGTCTGAAGTAG |
| SEQ ID NO:55 | TCTGAGCCACTCTCCTTATTTAGA |
| SEQ ID NO:56 | TAGATTGGGCACTTCACAAGAATG |
| SEQ ID NO:57 | ACAGCAGAACCCAGTCTCACTGAG |

FIG. 34

| SEQ ID NO:58 | TCTCACAGTTCTGGAGGCTGGAAG |
| SEQ ID NO:59 | GGTGGACCCTAATTGCATAGGATTG |
| SEQ ID NO:60 | TGTCCTCTAGGGGAAGAGATGTCT |
| SEQ ID NO:61 | AGGTCAGGGACCTAGTAACTACTC |
| SEQ ID NO:62 | CCAGAGCCCTACAGGAGTGTACTG |
| SEQ ID NO:63 | CAAGACCAGGGGATCACAGTAACT |
| SEQ ID NO:64 | CAGCCTGGGCAACAGAGACTC |
| SEQ ID NO:65 | AGGCGCTAAATTCAGAGCAAATAG |
| SEQ ID NO:66 | GCTGTAATGGTGCTGTGTAAATCT |
| SEQ ID NO:67 | AAGAATCCTCCAGACTTCATACAC |
| SEQ ID NO:68 | ATCAGCTTAGCAGACATCTCTTCC |
| SEQ ID NO:69 | CTTGTAGTCCCAGCTACTCAGTGG |
| SEQ ID NO:70 | CACGAGAATCCCTTGAACCTG |
| SEQ ID NO:71 | TGGCTCTCCACTCAGAGATTC |
| SEQ ID NO:72 | CTGTGGCTGGCTTGTTTCACTCAG |
| SEQ ID NO:73 | TTGGGTGGAGGCAATCCAAGTGTC |
| SEQ ID NO:74 | TGTGTTATTGGTGAAATGCACATA |
| SEQ ID NO:75 | GGTGGCTCATGCCTGTAATTTGAG |
| SEQ ID NO:76 | TGACAGGCACATAGATTATTATGC |
| SEQ ID NO:77 | CGTACCCGGCTGATTATTTAGAT |
| SEQ ID NO:78 | AGATAGGGGTCTAGTTTCATTATC |
| SEQ ID NO:79 | ACAAAGCTGGACATATCACACTAC |
| SEQ ID NO:80 | AGGCTGGTCTCGAACTCCTGACCT |
| SEQ ID NO:81 | GGGACTACAGGTGTGTGAATTTGA |
| SEQ ID NO:82 | AGGACGGCTGAATGTCTGTCATCA |
| SEQ ID NO:83 | TTGGGGAGTCCCTAAATGACTTTA |
| SEQ ID NO:84 | GGCAGAAATGGCACATCTTAACTA |
| SEQ ID NO:85 | CAGCCTGGGTGACAGAGTGAGACT |
| SEQ ID NO:86 | ACCCAGTAGAGACCCATCTTACTC |
| SEQ ID NO:87 | ACCCAGTAGAGACCCATCTTACTC |

FIG. 35

```
                             SEQUENCE LISTING

<160> NUMBER OF SEQ ID NOS: 87

<210> SEQ ID NO 1
<211> LENGTH: 27
<212> TYPE: DNA
<213> ORGANISM: Artificial
<220> FEATURE:
<223> OTHER INFORMATION: DNA UMOD Sequence portion from Fig. 5

<400> SEQUENCE: 1
tccgtgtcag gcgcaccgca ccctgga                                     27

<210> SEQ ID NO 2
<211> LENGTH: 27
<212> TYPE: DNA
<213> ORGANISM: Artificial
<220> FEATURE:
<223> OTHER INFORMATION: DNA UMOD Sequence portion from Fig. 5

<400> SEQUENCE: 2
ccgcctgtcg cccggtctcg gctgcac                                     27

<210> SEQ ID NO 3
<211> LENGTH: 25
<212> TYPE: DNA
<213> ORGANISM: Artificial
<220> FEATURE:
<223> OTHER INFORMATION: DNA UMOD Sequence portion from Fig. 5

<400> SEQUENCE: 3
atggatggca ctgtgagtgc tcccc                                       25

<210> SEQ ID NO 4
<211> LENGTH: 24
<212> TYPE: DNA
<213> ORGANISM: Artificial
<220> FEATURE:
<223> OTHER INFORMATION: DNA UMOD Sequence portion from Fig. 5

<400> SEQUENCE: 4
atggccgaga cctgcgtgcc agtc                                        24

<210> SEQ ID NO 5
<211> LENGTH: 27
<212> TYPE: DNA
<213> ORGANISM: Artificial
<220> FEATURE:
<223> OTHER INFORMATION: DNA UMOD Sequence portion from Fig. 5

<400> SEQUENCE: 5
tccgtgtcag gcgagcagcg agtacgg                                     27

<210> SEQ ID NO 6
<211> LENGTH: 27
<212> TYPE: DNA
<213> ORGANISM: Artificial
<220> FEATURE:
<223> OTHER INFORMATION: DNA UMOD Sequence portion from Fig. 5
```

-continued

<400> SEQUENCE: 6
ccgcctgtcg ccctgtctcg gctgcac                                      27

<210> SEQ ID NO 7
<211> LENGTH: 24
<212> TYPE: DNA
<213> ORGANISM: Artificial
<220> FEATURE:
<223> OTHER INFORMATION: DNA UMOD Sequence portion from Fig. 5

<400> SEQUENCE: 7
tggatggcac tatgagtgct cccc                                         24

<210> SEQ ID NO 8
<211> LENGTH: 24
<212> TYPE: DNA
<213> ORGANISM: Artificial
<220> FEATURE:
<223> OTHER INFORMATION: DNA UMOD Sequence portion from Fig. 5

<400> SEQUENCE: 8
atggccgaga cccgcgtgcc agtc                                         24

<210> SEQ ID NO 9
<211> LENGTH: 640
<212> TYPE: PRT
<213> ORGANISM: Homo sapiens

<400> SEQUENCE: 9

Met Gly Gln Pro Ser Leu Thr Trp Met Leu Met Val Val Val Ala Ser
1               5                   10                  15

Trp Phe Ile Thr Thr Ala Ala Thr Asp Thr Ser Glu Ala Arg Trp Cys
            20                  25                  30

Ser Glu Cys His Ser Asn Ala Thr Cys Thr Glu Asp Glu Ala Val Thr
        35                  40                  45

Thr Cys Thr Cys Gln Glu Gly Phe Thr Gly Asp Gly Leu Thr Cys Val
    50                  55                  60

Asp Leu Asp Glu Cys Ala Ile Pro Gly Ala His Asn Cys Ser Ala Asn
65                  70                  75                  80

Ser Ser Cys Val Asn Thr Pro Gly Ser Phe Ser Cys Val Cys Pro Glu
                85                  90                  95

Gly Phe Arg Leu Ser Pro Gly Leu Gly Cys Thr Asp Val Asp Glu Cys
            100                 105                 110

Ala Glu Pro Gly Leu Ser His Cys His Ala Leu Ala Thr Cys Val Asn
        115                 120                 125

Val Val Gly Ser Tyr Leu Cys Val Cys Pro Ala Gly Tyr Arg Gly Asp
    130                 135                 140

Gly Trp His Cys Glu Cys Ser Pro Gly Ser Cys Gly Pro Gly Leu Asp
145                 150                 155                 160

Cys Val Pro Glu Gly Asp Ala Leu Val Cys Ala Asp Pro Cys Gln Ala
                165                 170                 175

His Arg Thr Leu Asp Glu Tyr Trp Arg Ser Thr Glu Tyr Gly Glu Gly
            180                 185                 190

Tyr Ala Cys Asp Thr Asp Leu Arg Gly Trp Tyr Arg Phe Val Gly Gln
        195                 200                 205

Gly Gly Ala Arg Met Ala Glu Thr Cys Val Pro Val Leu Arg Cys Asn
    210                 215                 220

Thr Ala Ala Pro Met Trp Leu Asn Gly Thr His Pro Ser Ser Asp Glu

```
                225                 230                 235                 240
Gly Ile Val Ser Arg Lys Ala Cys Ala His Trp Ser Gly His Cys Cys
                245                 250                 255
Leu Trp Asp Ala Ser Val Gln Val Lys Ala Cys Ala Gly Gly Tyr Tyr
                260                 265                 270
Val Tyr Asn Leu Thr Ala Pro Pro Glu Cys His Leu Ala Tyr Cys Thr
                275                 280                 285
Asp Pro Ser Ser Val Glu Gly Thr Cys Glu Glu Cys Ser Ile Asp Glu
                290                 295                 300
Asp Cys Lys Ser Asn Asn Gly Arg Trp His Cys Gln Cys Lys Gln Asp
305                 310                 315                 320
Phe Asn Ile Thr Asp Ile Ser Leu Leu Glu His Arg Leu Glu Cys Gly
                325                 330                 335
Ala Asn Asp Met Lys Val Ser Leu Gly Lys Cys Gln Leu Lys Ser Leu
                340                 345                 350
Gly Phe Asp Lys Val Phe Met Tyr Leu Ser Asp Ser Arg Cys Ser Gly
                355                 360                 365
Phe Asn Asp Arg Asp Asn Arg Asp Trp Val Ser Val Val Thr Pro Ala
                370                 375                 380
Arg Asp Gly Pro Cys Gly Thr Val Leu Thr Arg Asn Glu Thr His Ala
385                 390                 395                 400
Thr Tyr Ser Asn Thr Leu Tyr Leu Ala Asp Glu Ile Ile Ile Arg Asp
                405                 410                 415
Leu Asn Ile Lys Ile Asn Phe Ala Cys Ser Tyr Pro Leu Asp Met Lys
                420                 425                 430
Val Ser Leu Lys Thr Ala Leu Gln Pro Met Val Ser Ala Leu Asn Ile
                435                 440                 445
Arg Val Gly Gly Thr Gly Met Phe Thr Val Arg Met Ala Leu Phe Gln
                450                 455                 460
Thr Pro Ser Tyr Thr Gln Pro Tyr Gln Gly Ser Ser Val Thr Leu Ser
465                 470                 475                 480
Thr Glu Ala Phe Leu Tyr Val Gly Thr Met Leu Asp Gly Gly Asp Leu
                485                 490                 495
Ser Arg Phe Ala Leu Leu Met Thr Asn Cys Tyr Ala Thr Pro Ser Ser
                500                 505                 510
Asn Ala Thr Asp Pro Leu Lys Tyr Phe Ile Ile Gln Asp Arg Cys Pro
                515                 520                 525
His Thr Arg Asp Ser Thr Ile Gln Val Val Glu Asn Gly Glu Ser Ser
                530                 535                 540
Gln Gly Arg Phe Ser Val Gln Met Phe Arg Phe Ala Gly Asn Tyr Asp
545                 550                 555                 560
Leu Val Tyr Leu Asp Cys Glu Val Tyr Leu Cys Asp Thr Met Asn Glu
                565                 570                 575
Lys Cys Lys Pro Thr Cys Ser Gly Thr Arg Phe Arg Ser Gly Ser Val
                580                 585                 590
Ile Asp Gln Ser Arg Val Leu Asn Leu Gly Pro Ile Thr Arg Lys Gly
                595                 600                 605
Val Gln Ala Thr Val Ser Arg Ala Phe Ser Ser Leu Gly Leu Leu Lys
                610                 615                 620
Val Trp Leu Pro Leu Leu Leu Ser Ala Thr Leu Thr Leu Thr Phe Gln
625                 630                 635                 640

<210> SEQ ID NO 10
```

<211> LENGTH: 643
<212> TYPE: PRT
<213> ORGANISM: Bos taurus

<400> SEQUENCE: 10

```
Met Lys Cys Leu Phe Ser Pro Asn Phe Met Trp Met Ala Ala Val Val
1               5                   10                  15

Thr Ser Trp Val Ile Ile Pro Ala Ala Thr Asp Thr Ser Ser Ala Lys
            20                  25                  30

Ser Cys Ser Glu Cys His Ser Asn Ala Thr Cys Thr Val Asp Gly Ala
        35                  40                  45

Ala Thr Thr Cys Ala Cys Gln Glu Gly Phe Thr Gly Asp Gly Leu Glu
    50                  55                  60

Cys Val Asp Leu Asp Glu Cys Ala Val Leu Gly Ala His Asn Cys Ser
65                  70                  75                  80

Ala Thr Lys Ser Cys Val Asn Thr Leu Gly Ser Tyr Thr Cys Val Cys
                85                  90                  95

Pro Glu Gly Phe Leu Leu Ser Ser Glu Leu Gly Cys Glu Asp Val Asp
            100                 105                 110

Glu Cys Ala Glu Pro Gly Leu Ser Arg Cys His Ala Leu Ala Thr Cys
        115                 120                 125

Ile Asn Gly Glu Gly Asn Tyr Ser Cys Val Cys Pro Ala Gly Tyr Leu
    130                 135                 140

Gly Asp Gly Arg His Cys Glu Cys Ser Pro Gly Ser Cys Gly Pro Gly
145                 150                 155                 160

Leu Asp Cys Val Arg Glu Gly Asp Ala Leu Val Cys Val Asp Pro Cys
                165                 170                 175

Gln Val His Arg Ile Leu Asp Glu Tyr Trp Arg Ser Thr Glu Tyr Gly
            180                 185                 190

Ser Gly Tyr Ile Cys Asp Val Ser Leu Gly Gly Trp Tyr Arg Phe Val
        195                 200                 205

Gly Gln Ala Gly Val Arg Leu Pro Glu Thr Cys Val Pro Val Leu His
    210                 215                 220

Cys Asn Thr Ala Ala Pro Met Trp Leu Asn Gly Thr His Pro Ser Ser
225                 230                 235                 240

Asp Glu Gly Ile Val Asn Arg Val Ala Cys Ala His Trp Ser Gly Asp
                245                 250                 255

Cys Cys Leu Trp Asp Ala Pro Ile Gln Val Lys Ala Cys Ala Gly Gly
            260                 265                 270

Tyr Tyr Val Tyr Asn Leu Thr Ala Pro Pro Glu Cys His Leu Ala Tyr
        275                 280                 285

Cys Thr Asp Pro Ser Ser Val Glu Gly Thr Cys Glu Glu Cys Arg Val
    290                 295                 300

Asp Glu Asp Cys Lys Ser Asp Asn Gly Glu Trp His Cys Gln Cys Lys
305                 310                 315                 320

Gln Asp Phe Asn Val Thr Asp Leu Ser Leu Leu Glu Arg Arg Leu Glu
                325                 330                 335

Cys Gly Val Asp Asp Ile Lys Leu Ser Leu Ser Lys Cys Gln Leu Lys
            340                 345                 350

Ser Leu Gly Phe Glu Lys Val Phe Met Tyr Leu His Asp Ser Gln Cys
        355                 360                 365

Ser Gly Phe Thr Glu Arg Gly Asp Arg Asp Trp Met Ser Val Val Thr
    370                 375                 380

Pro Ala Arg Asp Gly Pro Cys Gly Thr Val Met Thr Arg Asn Glu Thr
```

```
                385                 390                 395                 400

His Ala Thr Tyr Ser Asn Thr Leu Tyr Leu Ala Asp Glu Ile Ile Ile
                    405                 410                 415

Arg Asp Leu Asn Ile Arg Ile Asn Phe Ala Cys Ser Tyr Pro Leu Asp
                420                 425                 430

Met Lys Val Ser Leu Lys Thr Ser Leu Gln Pro Met Val Ser Ala Leu
            435                 440                 445

Asn Ile Ser Met Gly Gly Thr Gly Thr Phe Thr Val Arg Met Ala Leu
        450                 455                 460

Phe Gln Ser Pro Ala Tyr Thr Gln Pro Tyr Gln Gly Ser Ser Val Thr
465                 470                 475                 480

Leu Ser Thr Glu Ala Phe Leu Tyr Val Gly Thr Met Leu Asp Gly Gly
                485                 490                 495

Asp Leu Ser Arg Phe Val Leu Leu Met Thr Asn Cys Tyr Ala Thr Pro
                500                 505                 510

Ser Ser Asn Ala Thr Asp Pro Leu Lys Tyr Phe Ile Ile Gln Asp Arg
            515                 520                 525

Cys Pro Arg Ala Ala Asp Ser Thr Ile Gln Val Glu Glu Asn Gly Glu
        530                 535                 540

Ser Pro Gln Gly Arg Phe Ser Val Gln Met Phe Arg Phe Ala Gly Asn
545                 550                 555                 560

Tyr Asp Leu Val Tyr Leu His Cys Glu Val Tyr Leu Cys Asp Thr Val
                565                 570                 575

Asn Glu Lys Cys Arg Pro Thr Cys Pro Glu Thr Arg Phe Arg Ser Gly
                580                 585                 590

Ser Ile Ile Asp Gln Thr Arg Val Leu Asn Leu Gly Pro Ile Thr Arg
            595                 600                 605

Lys Gly Gly Gln Ala Ala Met Ser Arg Ala Ala Pro Ser Ser Leu Gly
        610                 615                 620

Leu Leu Gln Val Trp Leu Pro Leu Leu Leu Ser Ala Thr Leu Thr Leu
625                 630                 635                 640

Met Ser Pro

<210> SEQ ID NO 11
<211> LENGTH: 642
<212> TYPE: PRT
<213> ORGANISM: Mus musculus

<400> SEQUENCE: 11

Met Gly Ile Pro Leu Thr Trp Met Leu Leu Val Met Met Val Thr Ser
1               5                   10                  15

Trp Phe Thr Leu Ala Glu Ala Ser Asn Ser Thr Glu Ala Arg Arg Cys
            20                  25                  30

Ser Glu Cys His Asn Asn Ala Thr Cys Thr Val Asp Gly Val Val Thr
        35                  40                  45

Thr Cys Ser Cys Gln Thr Gly Phe Thr Gly Asp Gly Leu Val Cys Glu
    50                  55                  60

Asp Met Asp Glu Cys Ala Thr Pro Trp Thr His Asn Cys Ser Asn Ser
65                  70                  75                  80

Ser Cys Val Asn Thr Pro Gly Ser Phe Lys Cys Ser Cys Gln Asp Gly
                85                  90                  95

Phe Arg Leu Thr Pro Glu Leu Ser Cys Thr Asp Val Asp Glu Cys Ser
            100                 105                 110

Glu Gln Gly Leu Ser Asn Cys His Ala Leu Ala Thr Cys Val Asn Thr
```

-continued

```
            115                 120                 125
Glu Gly Asp Tyr Leu Cys Val Cys Pro Glu Gly Phe Thr Gly Asp Gly
    130                 135                 140
Trp Tyr Cys Glu Cys Ser Pro Gly Ser Cys Glu Pro Gly Leu Asp Cys
145                 150                 155                 160
Leu Pro Gln Gly Pro Asp Gly Lys Leu Val Cys Gln Asp Pro Cys Asn
                165                 170                 175
Thr Tyr Glu Thr Leu Thr Glu Tyr Trp Arg Ser Thr Glu Tyr Gly Val
            180                 185                 190
Gly Tyr Ser Cys Asp Ala Gly Leu His Gly Trp Tyr Arg Phe Thr Gly
        195                 200                 205
Gln Gly Gly Val Arg Met Ala Glu Thr Cys Val Pro Val Leu Arg Cys
    210                 215                 220
Asn Thr Ala Ala Pro Met Trp Leu Asn Gly Ser His Pro Ser Ser Ser
225                 230                 235                 240
Glu Gly Ile Val Ser Arg Thr Ala Cys Ala His Trp Ser Asp Gln Cys
                245                 250                 255
Cys Arg Trp Ser Thr Glu Ile Gln Val Lys Ala Cys Pro Gly Gly Phe
            260                 265                 270
Tyr Ile Tyr Asn Leu Thr Ala Pro Pro Glu Cys Asn Leu Ala Tyr Cys
        275                 280                 285
Thr Asp Pro Ser Ser Val Glu Gly Thr Cys Glu Glu Cys Arg Val Asp
    290                 295                 300
Glu Asp Cys Ile Ser Asp Asn Gly Arg Trp Arg Cys Gln Cys Lys Gln
305                 310                 315                 320
Asp Ser Asn Ile Thr Asp Val Ser Gln Leu Glu Tyr Arg Leu Glu Cys
                325                 330                 335
Gly Ala Asn Asp Ile Lys Met Ser Leu Arg Lys Cys Gln Leu Gln Ser
            340                 345                 350
Leu Gly Phe Met Asn Val Phe Met Tyr Leu Asn Asp Arg Gln Cys Ser
        355                 360                 365
Gly Phe Ser Glu Ser Asp Glu Arg Asp Trp Met Ser Ile Val Thr Pro
    370                 375                 380
Ala Arg Asn Gly Pro Cys Gly Thr Val Leu Arg Arg Asn Glu Thr His
385                 390                 395                 400
Ala Thr Tyr Ser Asn Thr Leu Tyr Leu Ala Asn Ala Ile Ile Ile Arg
                405                 410                 415
Asp Ile Ile Ile Arg Met Asn Phe Glu Cys Ser Tyr Pro Leu Asp Met
            420                 425                 430
Lys Val Ser Leu Lys Thr Ser Leu Gln Pro Met Val Ser Ala Leu Asn
        435                 440                 445
Ile Ser Leu Gly Gly Thr Gly Lys Phe Thr Val Arg Met Ala Leu Phe
    450                 455                 460
Gln Ser Pro Thr Tyr Thr Gln Pro His Gln Gly Pro Ser Val Met Leu
465                 470                 475                 480
Ser Thr Glu Ala Phe Leu Tyr Val Gly Thr Met Leu Asp Gly Gly Asp
                485                 490                 495
Leu Ser Arg Phe Val Leu Leu Met Thr Asn Cys Tyr Ala Thr Pro Ser
            500                 505                 510
Ser Asn Ser Thr Asp Pro Val Lys Tyr Phe Ile Ile Gln Asp Ser Cys
        515                 520                 525
Pro Arg Thr Glu Asp Thr Thr Ile Gln Val Thr Glu Asn Gly Glu Ser
    530                 535                 540
```

```
Ser Gln Ala Arg Phe Ser Val Gln Met Phe Arg Phe Ala Gly Asn Tyr
545                 550                 555                 560

Asp Leu Val Tyr Leu His Cys Glu Val Tyr Leu Cys Asp Ser Thr Ser
                565                 570                 575

Glu Gln Cys Lys Pro Thr Cys Ser Gly Thr Arg Phe Arg Ser Gly Asn
                580                 585                 590

Phe Ile Asp Gln Thr Arg Val Leu Asn Leu Gly Pro Ile Thr Arg Gln
                595                 600                 605

Gly Val Gln Ala Ser Val Ser Lys Ala Ala Ser Ser Asn Leu Arg Leu
                610                 615                 620

Leu Ser Ile Trp Leu Leu Leu Phe Pro Ser Ala Thr Leu Ile Phe Met
625                 630                 635                 640

Val Gln

<210> SEQ ID NO 12
<211> LENGTH: 644
<212> TYPE: PRT
<213> ORGANISM: Rattus norvegicus

<400> SEQUENCE: 12

Met Gly Gln Leu Leu Ser Leu Thr Trp Leu Leu Leu Val Met Val Val
1               5                   10                  15

Thr Pro Trp Phe Thr Val Ala Gly Ala Asn Asp Ser Pro Glu Ala Arg
                20                  25                  30

Arg Cys Ser Glu Cys His Asp Asn Ala Thr Cys Val Leu Asp Gly Val
                35                  40                  45

Val Thr Thr Cys Ser Cys Gln Ala Gly Phe Thr Gly Asp Gly Leu Val
        50                  55                  60

Cys Glu Asp Ile Asp Glu Cys Ala Thr Pro Trp Thr His Asn Cys Ser
65                  70                  75                  80

Asn Ser Ile Cys Met Asn Thr Leu Gly Ser Tyr Glu Cys Ser Cys Gln
                85                  90                  95

Asp Gly Phe Arg Leu Thr Pro Gly Leu Gly Cys Ile Asp Val Asn Glu
                100                 105                 110

Cys Thr Glu Gln Gly Leu Ser Asn Cys His Ser Leu Ala Thr Cys Val
                115                 120                 125

Asn Thr Glu Gly Ser Tyr Ser Cys Val Cys Pro Lys Gly Tyr Arg Gly
                130                 135                 140

Asp Gly Trp Tyr Cys Glu Cys Ser Pro Gly Phe Cys Glu Pro Gly Leu
145                 150                 155                 160

Asp Cys Leu Pro Gln Gly Pro Ser Gly Lys Leu Val Cys Gln Asp Pro
                165                 170                 175

Cys Asn Val Tyr Glu Thr Leu Thr Glu Tyr Trp Arg Ser Thr Asp Tyr
                180                 185                 190

Gly Ala Gly Tyr Ser Cys Asp Ser Asp Met His Gly Trp Tyr Arg Phe
                195                 200                 205

Thr Gly Gln Gly Gly Val Arg Met Ala Glu Thr Cys Val Pro Val Leu
                210                 215                 220

Arg Cys Asn Thr Ala Ala Pro Met Trp Leu Asn Gly Ser His Pro Ser
225                 230                 235                 240

Ser Arg Glu Gly Ile Val Ser Arg Thr Ala Cys Ala His Trp Ser Asp
                245                 250                 255

His Cys Cys Leu Trp Ser Thr Glu Ile Gln Val Lys Ala Cys Pro Gly
                260                 265                 270
```

Gly Phe Tyr Val Tyr Asn Leu Thr Glu Pro Pro Glu Cys Asn Leu Ala
            275                 280                 285

Tyr Cys Thr Asp Pro Ser Ser Val Glu Gly Thr Cys Glu Glu Cys Gly
        290                 295                 300

Val Asp Glu Asp Cys Val Ser Asp Asn Gly Arg Trp Arg Cys Gln Cys
305                 310                 315                 320

Lys Gln Asp Phe Asn Val Thr Asp Val Ser Leu Leu Glu His Arg Leu
                325                 330                 335

Glu Cys Glu Ala Asn Glu Ile Lys Ile Ser Leu Ser Lys Cys Gln Leu
            340                 345                 350

Gln Ser Leu Gly Phe Met Lys Val Phe Met Tyr Leu Asn Asp Arg Gln
        355                 360                 365

Cys Ser Gly Phe Ser Glu Arg Gly Glu Arg Asp Trp Met Ser Ile Val
    370                 375                 380

Thr Pro Ala Arg Asp Gly Pro Cys Gly Thr Val Leu Arg Arg Asn Glu
385                 390                 395                 400

Thr His Ala Thr Tyr Ser Asn Thr Leu Tyr Leu Ala Ser Glu Ile Ile
                405                 410                 415

Ile Arg Asp Ile Asn Ile Arg Ile Asn Phe Glu Cys Ser Tyr Pro Leu
            420                 425                 430

Asp Met Lys Val Ser Leu Lys Thr Ser Leu Gln Pro Met Val Ser Ala
        435                 440                 445

Leu Asn Ile Ser Leu Gly Gly Thr Gly Lys Phe Thr Val Gln Met Ala
    450                 455                 460

Leu Phe Gln Asn Pro Thr Tyr Thr Gln Pro Tyr Gln Gly Pro Ser Val
465                 470                 475                 480

Met Leu Ser Thr Glu Ala Phe Leu Tyr Val Gly Thr Met Leu Asp Gly
                485                 490                 495

Gly Asp Leu Ser Arg Phe Val Leu Leu Met Thr Asn Cys Tyr Ala Thr
            500                 505                 510

Pro Ser Ser Asn Ser Thr Asp Pro Val Lys Tyr Phe Ile Ile Gln Asp
        515                 520                 525

Arg Cys Pro His Thr Glu Asp Thr Thr Ile Gln Val Thr Glu Asn Gly
    530                 535                 540

Glu Ser Ser Gln Ala Arg Phe Ser Ile Gln Met Phe Arg Phe Ala Gly
545                 550                 555                 560

Asn Ser Asp Leu Val Tyr Leu His Cys Glu Val Tyr Leu Cys Asp Thr
                565                 570                 575

Met Ser Glu Gln Cys Lys Pro Thr Cys Ser Gly Thr Arg Tyr Arg Ser
            580                 585                 590

Gly Asn Phe Ile Asp Gln Thr Arg Val Leu Asn Leu Gly Pro Ile Thr
        595                 600                 605

Arg Gln Gly Val Gln Ala Ser Val Ser Lys Ala Ala Ser Ser Asn Leu
    610                 615                 620

Gly Phe Leu Ser Ile Trp Leu Leu Phe Leu Ser Ala Thr Leu Thr
625                 630                 635                 640

Leu Met Val His

<210> SEQ ID NO 13
<211> LENGTH: 3199
<212> TYPE: DNA
<213> ORGANISM: Homo sapiens

<400> SEQUENCE: 13

```
tcctgctcca aatgactgag ttcttcaaaa tgtgcaatgt gctgagaatt ggggagccaa      60
gactgggatg ttggtgaggt aaggaggggg agtacaaggg gtaaagtccc agcaaaacaa     120
gggctgcagt gttatgcaat tttttagtcc atataagtga cacctcctgg agttgtatac     180
tatacaatca aagcactcct tccagctgtg gggaggagag ttagatcatg catttgtccc     240
atccatctct gttcacagga caccagacat cagagacaga gagaaaaatt caaagggcca     300
acccgtcttt cctttgggca ggtgctatct agacctgaag tagcgggaag agcagaaagg     360
atggggcagc catctctgac ttggatgctg atggtggtgg tggcctcttg gttcatcaca     420
actgcagcca ctgacacctc agaagcaagt aagtgaaaag tgtgtgtgcg ttgtatatgt     480
gtgtatgcac gtgtatgtgt gaatgtgtgg gggaagcaat gtagcacctg tcagaggtga     540
tctcaatcct cctatcgcac ttgagacttg cattgtcttc attctaagtc catttcttag     600
actcaatatg cacaggactg acttagaaat tttgctaaag tgcatattct ggttcagcag     660
atctgcagta ggacctgaga tgctgaattt ttaacaagct tccaggcgat gctcatactg     720
gggtccctgg agtacacatt gaaaagcaag gggctagaac atctctaagg cctgcaggcc     780
ctttattgga agtcagaaac atactctatc acataggaga tttgaaccca tgcaggagga     840
tccaaacacc ttccctttca actttaagag gtcattccat tggggttgaga tttgctgtca    900
ccccactttc attttctccc tggagtacgt tggggcacga tgaatactat tgcggtgtcc     960
tggttaaaag cacatatttt gtggtcctgc catctgcgtt tttatcctgg ttctacttct    1020
taccaaagga gtaaggggct taatccctct gaacctcagt ctcctcatct ttaaaataag    1080
gatacataaa aaactgacct cacgaggccc ttgggaagta ttcaacaaga tagtgagtga    1140
aaagtgcaca tcctattgcc tggcatatag taattgctta ataacaaca gcttctttttt    1200
ttttttaatg gttattttta ttacggagga acaaagtaca actgcccagc caggtggagt    1260
tggaggactc cgcagagagg aggcgacact gagcagggtc ctgatgaaga tttcaccagc    1320
cagggaagca gaaaacataa aatgtgcaaa gaaagggagg ggcaacaggt tcaccgtaaa    1380
tcctaccaaa gtataggaat tctgcgcatt acttttctga atgtggctat tttaaaagaa    1440
gacagcttga aagcaatgct taacacaaaa aatgaatggt ggagctgggc gcgattgcac    1500
gtgcctgtgg tcccaacttt ttgggaagct gaggcagggt gcggtggtgg cttgaactca    1560
gggagtagaa cgcttgaacc caggaattgg aggctatggt gagctatgat cgcactactg    1620
cactccagcc tgggcgacag agcaagaccc ctctccaaaa aaataaataa agttaaaaaa    1680
tacaatgaaa taaacacaga atgaacggtg gaggcttgac atcatcagag gagttttgtt    1740
tctttgcttc tttccttgtt ttggagggag ccctctaggg aataagtctt aaaaataatg    1800
agttccctgg agaatgaggg aaggatctct gggtggccat gggcccagct gcccaaaccc    1860
tgaagctggg cttttctgtc cacaggatgg tgctctgaat gtcacagcaa tgccacctgc    1920
acggaggatg aggccgttac gacgtgcacc tgtcaggagg gcttcaccgg cgatggcctg    1980
acctgcgtgg acctggatga gtgcgccatt cctggagctc acaactgctc cgccaacagc    2040
agctgcgtaa acacgccagg ctccttctcc tgcgtctgcc ccgaaggctt ccgcctgtcg    2100
cccggtctcg gctgcacaga cgtggatgag tgcgctgagc ctgggcttag ccactgccac    2160
gccctggcca catgtgtcaa tgtggtgggc agctacttgt gcgtatgccc cgcgggctac    2220
cgggggggatg gatggcactg tgagtgctcc ccgggctcct gcgggccggg gttggactgc    2280
gtgcccgagg gcgacgcgct cgtgtgcgcg gatccgtgtc aggcgcaccg caccctggac    2340
```

```
gagtactggc gcagcaccga gtacggggag ggctacgcct gcgacacgga cctgcgcggc    2400
tggtaccgct tcgtgggcca gggcggtgcg cgcatggccg agacctgcgt gccagtcctg    2460
cgctgcaaca cggccgcccc catgtggctc aatggcacgc atccgtccag cgacgagggc    2520
atcgtgagcc gcaaggcctg cgcgcactgg agcggccact gctgcctgtg ggatgcgtcc    2580
gtccaggtga aggcctgtgc cggcggctac tacgtctaca acctgacagc gccccccgag    2640
tgtcacctgg cgtactgcac aggtcagccg gagtctcccc acagtcctca tcccaggcct    2700
ggaaaggcac tgcagaggac gggggtgcgt ccttattgat tgtctgtctg tccctgtgac    2760
cctgcagacc ccagctccgt ggaggggacg tgtgaggagt gcagtataga cgaggactgc    2820
aaatcgaata atggcagatg gcactgccag tgcaaacagg acttcaacat cactggtgag    2880
gccagtgggg aggaagcggg ttgttgagaa acctgtcact gcctggggga gggacacatt    2940
cctcccctgt gagattgggg ccatatgggt atgacgcagg ggatatatat ccaacctgag    3000
tgaaaacaga agatccacta ataccattaa aagccggcaa gaggctctct gaggctccct    3060
gagtctccct ttagttgact tcaaagctgc caaagatttg gggacctcct cgcacccagc    3120
cttctttctg aggcccacac cacagtgggc acccacgttg ctgccatctg ggagccaaag    3180
accatctgag ccctattcc                                                3199

<210> SEQ ID NO 14
<211> LENGTH: 940
<212> TYPE: DNA
<213> ORGANISM: Homo sapiens

<400> SEQUENCE: 14
acctctggac ctcaagtaat ctgtctgcct tggcctccca aagtgctagg attataggca      60
tgagccaccg catctagcct ttttattttt ttaaacgagt attcattgtt atttaatgct     120
gggacatcaa aacccccaa aaccgtcctg catttggtat ataacccaca tttaggggaa     180
cccaagactg agtggttggt cagtggatgt atccattgat gtcagaggtc caatcttgag     240
tccccatcac attgggaggg acagatcag ctcaaggcta tgctgagcac ttccagatgg      300
tggtcagccc agccagctgg acctggcccc tggggatgtg ctgggccccc aagctataga     360
cacacgtcct caatcccacc taacctgttt cagatatctc cctcctggag cacaggctgg     420
aatgtggggc caatgacatg aaggtgtcgc tgggcaagtg ccagctgaag agtctgggct     480
tcgacaaggt cttcatgtac ctgagtgaca gccggtgctc gggcttcaat gacagagaca     540
accgggactg ggtgtctgta gtgacccag cccgggatgg ccctgtggg acagtgttga       600 cggtacgtcc tggccagtgg gggacagaac cagagcactg cctggttcaa gtttcagctc     660
tatcacttcc tagttataga agctttgggg agttatttag cctggctgtg cctcagtttc     720
atcaactgta aagtggagaa ataatagtac ctactccaca ggtgtattga gaggattgaa     780
tgagttaatg tgttgaagtg attaggacag tgactgcaca cagtaagtgc tcaataaaca     840
tcagcttcaa ataaagaaag caattcatgg tgatagttct ccattttaca gatgggaaaa     900
gtagggccat agtagggatt gtctcagcca gtaggcatca                           940

<210> SEQ ID NO 15
<211> LENGTH: 475
<212> TYPE: DNA
<213> ORGANISM: Homo sapiens

<400> SEQUENCE: 15
accagcagat ttagctttga agtcctactc agattctcat gccccttct ctcatcccca       60
```

```
cccccccctcc acccccattc cctgcaacag aggaatgaaa cccatgccac ttacagcaac    120
accctctacc tggcagatga gatcatcatc cgtgacctca acatcaaaat caactttgca    180
tgctcctacc ccctggacat gaaagtcagc ctgaagaccg ccctacagcc aatggtcagg    240
tgtggccaga gagggtccct agggccccta gatggttcta accccaaacc ccttaaccat    300
gagcttccct gtcaactgcc acccacaggg agctgggagt gagggctggg aatcagggtt    360
gcccaatgga agagccagga attctggagc ccaggttcaa atctagactt tgtcataaat    420
gatggttatg ccctggccag tgggggacag agtcaaagca ctgcctggtt caagc         475

<210> SEQ ID NO 16
<211> LENGTH: 711
<212> TYPE: DNA
<213> ORGANISM: Homo sapiens

<400> SEQUENCE: 16
agcagcatcc aggcacttgt cagaaatgca ggaccttgag ccccaccca atactcacca     60 aatcagagcc tgcattttat ctagatccca agttgacctg cgtgtactta ttgcggtttg    120
caaagcaaca gttggtgggt tccactctta ttgctggata aaaatgcaaa caactgcaag    180
ggactgccta ggaatgcaaa tcagagaagg tggcctatct gcagatgttc tcagcccggt    240
cctctcacca acccttctcc cctggcagtg ctctaaacat cagagtgggc gggaccggca    300
tgttcaccgt gcggatggcg ctcttccaga ccccttccta cacgcagccc taccaaggct    360
cctccgtgac actgtccact gaggcttttc tctacgtggg caccatgttg gatggggcg    420 acctgtcccg atttgcactg ctcatgacca actgctatgc cacacccagt agcaatgcca    480 cggacccccct gaagtacttc atcatccagg acaggtaagg caaaggttcc tacatgggaa    540
ctcatgggta gaattcagag ggggtctttg gacttggatg gaggaaaatt gcatcttttt    600 ttttttttttt tttgacagag tcttgctctg tcgccaaggt tggagtgcaa tggtgtgacc    660
tcggctcact gcaacctccg cctcctgggt tcaagtgatt cttctgcctc a             711

<210> SEQ ID NO 17
<211> LENGTH: 1111
<212> TYPE: DNA
<213> ORGANISM: Homo sapiens

<400> SEQUENCE: 17
atttgaatcc aggaagtctg actccagaat ctttatttaa ccaaccacat taaatgatgt     60
gtaaccctcc cagatgccca cacactagag actcaactat ccaagtggtg gagaatgggg    120
agtcctccca gggccgattt tccgtccaga tgttccggtt tgctggaaac tatgaccctag    180 tctacctgca ctgtgaagtc tatctctgtg acaccatgaa tgaaaagtgc aagcctgtga    240
gttgactccc ctcccccagc ccatctcttg taaccaaaga catttggcca caaagaaaac    300
aaatcaatat ttcttccctg tttccctctt ttaccagagg gatagaatga gcaataagat    360
gaggtgggcg tggctaggca ggaaacctaa gctgcagggg aaatcaggtg ggatcagtaa    420
agtgcggcag gctggtaaga gctctggctt atctgcaagc ttgtgttcaa ataacaggag    480
ctgcactttt taagcactgt gcccacttta tttgtgttag cttttaatgc ttcacagcaa    540
ctctataagg gaggtattac tggttccctt tcctcatgag gagaggggct cagagaactt    600
cagtggcttg cctgagatca tgcatctatc taacaaatgg cagagctggg acctgcacga    660
gccccggtat acaggtctcc taacaacttc tgcctggggc aagggaaggc acctgtgagg    720
```

-continued

```
tgggcagtcc actccacgtg cagaaccac attcaggctc cttcatggag ggtgttttc       780
tattgccctc tccctgtaga cctgctctgg gaccagattc cgaagtggga gtgtcataga     840
tcaatcccgt gtcctgaact tgggtcccat cacacggaaa ggtaagagag ccactcgctc     900
ctcaacattc ctggctggga aagatttctg gagaggaaga gggataacag agcctggcac    960
cttggcacct tactgagctc tgaagaactg ggagcaagtg gatcctctgg ggcaaggtgg     1020
aatacagact gccttccttt cactattccc attcatacac ccattcattg gacaaatatg    1080
atttgtagat gaatgtaaca caggacacgg g                                    1111
```

<210> SEQ ID NO 18
<211> LENGTH: 345
<212> TYPE: DNA
<213> ORGANISM: Homo sapiens

<400> SEQUENCE: 18

```
gagcccctga tgggtctgaa gtagggagt aacatgatca gatttgggtt ttgaagagat     60
cagtctggct gcgaagtgaa aagtagattg aaggggtttc tgtcaggatg cttgccaaat   120
ctcatgcatt cttattcac tgatccttct gttttcctcc aaaggtgtcc aggccacagt    180
ctcaagggct tttagcagct tgggtaagtt caggtccttt ctgcagtggg acctgttcca    240
gaactctcct gggggcttc tatctgttaa cttgtaatgc ttcatagcaa ctctataagg    300
gaggtgttac tagttccgtt ttctaaataa ggagagtggc tcaga                    345
```

<210> SEQ ID NO 19
<211> LENGTH: 733
<212> TYPE: DNA
<213> ORGANISM: Homo sapiens

<400> SEQUENCE: 19

```
tagattgggc acttcacaag aatgcccttt gcccttttga ggaggtacca agcctagtgc     60
cggaggaaag attatctttt tcaaatcggt ccaccttttt cagggcagat aaggaggaag   120
cttccttttt ctaggagagc agcccagaga gggtgtcctc ttctgattgg tcagcctaga    180
cgaggcagct tatgttaatt tgcacaaaag tacagcagta ctagcagttg ccctgtcact    240
gttttctttt cagggctcct gaaagtctgg ctgcctctgc ttctctcggc caccttgacc    300
ctgacttttc agtgactgac agcggaaagc cctgtgctcc atggctgcca tctcacctcc    360
tgctgggcag ggggcatgat gcgggccagt gctccagcca cagaaaagaa agttcatgct    420
ttgttcagcc tgccttcttt tctcccttt aatcctggct gtcgagaaac agcctgtgtc    480
tttaaatgct gctttttctc aaaatgggac ttgtgacggt gtacctgagg ccccatctc    540
cttaaagagt gtggcaaaat aatgattttt aaatctcagt ctttgaagtc atccattcat   600
tcaacaagta tttactgaac tctaccatgt aggcactatg tatggtgcta aggatcctac    660
ggtggaaaa ataaccccc cacactgtcc tcatggagtt cacagtctgc tcagtgagac     720
tgggttctgc tgt                                                         733
```

<210> SEQ ID NO 20
<211> LENGTH: 4178
<212> TYPE: DNA
<213> ORGANISM: Homo sapiens

<400> SEQUENCE: 20

```
gcggccgcgg gagctgcggg gagcgcgggg gcggcccgga gcgtgccggg gtccccgcgc     60
ctcgctcgcc ggccgcgctc cgaagatggt ggcggcgccg tgcgcccgga ggctggcccg    120
```

| | |
|---|---|
| gcgctcgcac tcggcgctgc tcgcggcgct cacggtgctg ctgctgcaga cgctggtcgt | 180 |
| gtggaatttc agcagcctcg actccggggc cggggagcgc cgcggggggcg cagcggtcgg | 240 |
| cggcggggag cagccgcccc cggccccggc ccgcgccgg gagcgccggg acctgcccgc | 300 |
| cgagccggct gcagcccgag gaggaggagg aggcggcggc ggaggaggag gaggacgggg | 360 |
| gccccaggcg cgggcgcggg gaggcggccc cggagaaccg cggggacagc agccggccag | 420 |
| ccggggggca ctgcccgccc gggctctgga tccacaccca agtccgctca tcaccctgga | 480 |
| gactcaggat ggctactttt ctcatcggcc gaaagagaaa gtgcgaacag acagcaacaa | 540 |
| cgagaactct gtccccaaag actttgagaa tgtggacaac agcaacttcg cacccaggac | 600 |
| tcaaaagcag aagcaccagc ctgagttggc gaagaagcca ccgagtagac agaaggagct | 660 |
| tttgaaaagg aagctggaac agcaggagaa aggaaaagga catacattcc ctgggaaagg | 720 |
| ccccggtgag gtgctgcctc cggggacag agccgcagcc aacagcagcc acggaagga | 780 |
| tgtgtccaga ccgcctcatg ccaggaaaac tgggggcagc tcccccgaga ccaagtatga | 840 |
| ccagcccct aagtgtgaca tctcaggcaa ggaggccatc tctgccctgt cccgtgctaa | 900 |
| gtccaagcac tgccgccagg agattgggga acttactgc cgccacaagt tagggctgct | 960 |
| gatgcctgag aaggtgactc ggttctgccc cctcgagggt aaagccaaca gaacgtgca | 1020 |
| gtgggacgag gactccgtgg agtacatgcc agccaacccg gtcagaatcg cctttgtcct | 1080 |
| ggtggtccac ggccgtgcct ctcggcagtt gcagcgcatg ttcaaggcca tctaccacaa | 1140 |
| agaccacttc tactacatcc acgtggacaa gcgctctaat tacctgcatc ggcaagtgct | 1200 |
| ccaggtctcc aggcagtaca gcaatgtccg cgtcaccccc tggagaatgg ccaccatctg | 1260 |
| gggaggagcc agcctcctgt ccacctacct gcagagcatg cggacctcc tggagatgac | 1320 |
| cgactggccc tgggacttct tcatcaacct gagtgcggcc gactacccca tcaggacaaa | 1380 |
| tgaccagttg gtgcgtttc tctcccgata ccgagatatg aatttcttga agtcacacgg | 1440 |
| ccgggacaat gcaaggttca ttcggaagca gggcctggat cggctcttcc tggagtgcga | 1500 |
| cgctcacatg tggcgcctgg agatcggcg gatcccagag ggcattgccg tggatggcgg | 1560 |
| ttcggactgg ttcctgctga accggaggtt tgtagaatat gtgaccttct ccacagacga | 1620 |
| tctggtgacc aagatgaaac agttctactc ctacaccctg cttcctgctg agtccttctt | 1680 |
| ccatacggtc ctggagaaca gcccccactg cgacaccatg gtggacaaca acctgcgcat | 1740 |
| caccaactgg aatcgcaagc tgggctgcaa gtgccagtac aagcacatcg tggactggtg | 1800 |
| cggctgctcc cccaatgact tcaagccgca ggacttccac cgcttccagc agacagcccg | 1860 |
| gcctaccttt tttgcccgca gtttgaagc cgtggtgaat caggaaatca ttgggcagct | 1920 |
| ggactattac ctgtacggga actaccctgc aggtaccccg gcctgcgct cctactggga | 1980 |
| gaatgtctac gatgagcctg acggcatcca cagcctgagc gacgtgacac tcaccttgta | 2040 |
| ccactccttt gcccgcctgg gtcttcgacg ggccgagacg tccctgcaca cggatgggga | 2100 |
| gaacagctgc cgatactacc caatgggcca cccagcatct gtgcacctct acttccttgc | 2160 |
| tgaccgcttc cagggctttc tgatcaagca tcatgctacc aatctggctg tgagcaaact | 2220 |
| agagactctg gagacctggg tgatgccgaa aaaagtcttc aagatcgcaa gcccaccag | 2280 |
| tgactttggg aggcttcagt tttccgaggt cggcactgac tgggatgcca aggagaggct | 2340 |
| attccgcaac tttgggggtc ttctgggcc catggatgag ccgtggggta tgcagaagtg | 2400 |
| ggggaaggga cctaatgtga ccgtgaccgt catttgggtg gatcccgtca atgtcatcgc | 2460 |

```
agccacctac gacatcctca ttgagtccac tgccgaattc acacactaca agccccettt    2520 gaacttgccc ctgaggcctg gggtctggac agtgaaaatt ctccaccact gggtgccagt    2580
tgcagagacc aaattcctcg ttgcgcctct gaccttctcg aacaggcagc ccatcaaacc    2640
tgaggaggca ctgaagctgc acaatgggcc cctccgcaat gcctacatgg agcagagctt    2700
ccagagccta aaccccgtcc tcagcctgcc catcaacccc gcccaggtgg aacaggcacg    2760
gaggaacgca gcctccacgg gcacagcgct ggagggatgg ctggactcgt tggtgggcgg    2820
gatgtggact gccatggaca tctgtgccac gggccccaca gcctgcccgg tcatgcagac    2880
ctgcagccag acggcctgga gctccttcag ccctgacccc aagtcggagc tgggggcagt    2940
caaacctgat ggccggctca ggtagcactg gcacgagga gtgggccaca gcaggatctc    3000
aacgggaaag cagccagagg ggttgtgggg cctgaacccc ggcctccac cctgggggag    3060 gccctctgtg aatgggtctc tcctggccat agaatgatgg aaagggaagg tcagcaggtc    3120
aaagcaggat cagccaacaa cctgcctttg gcaagctgcg ggtgggatgg ctcagtccct    3180
gcactgtgac tgtctcacct cttctggttg atcctcaagt cctacaggtt ccttgtcttc    3240
cccttccagt gacccacccc tgaccccaga cgtgtgattt tcagactttt ctttcgagca    3300
gcagaacttc gtttacggag cacagtcata agtggaggtt cagggtgctg acgaaatcca    3360
agctgctctg gttgaagctg acaagtgcga ggttccctcc caaagctcag ccctctgggc    3420
ggtccccttg cccagggtat ctcctacggt acctcttcag aacccaaggg ctctgcaaat    3480
gccagtttga caagcactgc ccagaccaac catgggttca aactccagcc ctgcccttg     3540 gttcattttt ctgcttctct tggctggggg actctggtgc cagccttgaa agtcatggtc    3600
gtgggccctt tcccatggag gctgcagcct taggagagct ctgagcctct cagcagccct    3660
ccttgggttg aactattctc cttagtaact aggtaagtgg aaagccttt tgatgtggca    3720 tggccaaggt ccagccacaa gtgcaactgc cacctgtcca ggggtctggg cctccttccc    3780
tcaaggctgc cacacaaagt agcagaaata ggatgatgtt tgtgagcacc agactcaaga    3840
ccatgacctt ctttgatcct tgaaaatggg aactttgaca gccatgacca tgaaactcac    3900
aaggcaacgc gatgaaactc acaaagcaat gcttggagca aaactcctga gctagacagc    3960
acagcagcac ccatcccctg ccagagccct tccgttctga ggtcagacac acaaaacctt    4020
cgtcaattgc acaccggtgc tgtggagt gaccaaacca catgaaccag acttttcccg      4080
tccaggaaat agcatttcag atttggtttt taatttcatg cccttcggcc acaggctcaa    4140
cgggacatgc aacataaaaa tgggaaggtt atttaaac                            4178
```

<210> SEQ ID NO 21
<211> LENGTH: 2591
<212> TYPE: DNA
<213> ORGANISM: Homo sapiens

<400> SEQUENCE: 21

```
gccaagggca ctattggcca gttccgttca acgaagtggt tgctttttt agttccggca      60 atgagttgcg ccggggcggc ggcggctccc cgcctttggc ggctgcgccc ggggggccgg     120
cggtccctct cagcttatgg aagaagaacc agtgtcagat ttcgcagttc aggaatgact    180
ttagacaata tcagtcgggc agctgtggat cgaataatcc gggtggatca tgcaggcgaa    240
tatggagcaa accgcatcta tgccgggcag atggctgtcc tgggtcggac cagcgtcggg    300
ccagtcattc agaaaatgtg ggatcaagaa aaggaccatt tgaaaaagtt caatgagttg    360
atggttacgt tcagggtccg gccaacagtt ctgatgccct tgtggaacgt gctggggttt    420
```

```
gcactgggggg cggggaccgc cttgctcggg aaggaaggtg ccatggcctg caccgtggcg    480
gtggaagaga gcatagcaca tcactacaac aaccagatca ggacgctgat ggaggaggac    540
cctgaaaaat acgaggaact tcttcagctg ataaagaaat tcgggatgaa agagcttgag    600
caccatgaca taggcctcga ccatgatgca gaattggctc cagcctatgc cgtcctgaag    660
agcattatcc aggccggatg cagagtggcg atatatttat cagaaagatt ataaagtgtg    720
tccagttttg cctgtctata aagatgata  gtaatttacc aagtgacatt tgcagagaaa    780
caggtgtaca gttatcgttg tacttttgta caatgtgaat tttgttaata aattataagg    840 tttgttttt  tttttttaaa ctctgcagtg ttgattttc  tctggttgt  tttttctgcc    900 atgagaccaa caggtcacca gccttgttca agttacagca acgaagctg  ggccttgttt    960 ggtctcatac ttaattttct tttatataca tgttttctt  ttacatgcat atatatatat   1020
tttattttat tttatgtttt ttggagacag ggcctcgctc ttttgtccag gccgggtcac   1080
aactcactgc agcctggacc tcctagcctc aagcaatcca cccacctcag ccttccaagt   1140
agctgggact acaggtgtgc accaccacag ctggctaatt ctatttttt  atagaggcga   1200 agtctcacta tgtcgccagg ctggtctcta actcctgggc tcagtgatcc tcccgtttcg   1260
acttcccaaa gtgctgggat tacaggtgtg agccacttca ccaggcccat tttctcctaa   1320
aacttcaagg acaaatcatt aataatgtaa caggaatctt taggagaaaa aacaatttgg   1380
tttactgata acaaaagata attggaaaca tgagagtatt tgagattggc caagcagaac   1440
tatgaagtcc atcaagtaag tcaaagatca tcgtttctgt tttgaattgt gggtgataat   1500
gggtgggaga gtgctacagt ctgtatgtct gtgtctccct agaattcata cgatgaaatc   1560
ttcactctca agttgataga aggtgggggcc cttgggaagt gtgaggtcat gagagtggag   1620
ccctcatgaa tgggatcagt gccttatgaa aggccctaga gagataccctc atcctctcca   1680 cagtgtgaga cttcaagggg aagtatgaga cttctctgag gaagcagacc cttcacaagc   1740
aaaatcagcc agcactttga tcacggactt cccagcctct aggactgtga gcaataaatg   1800
tttgatgttt ataagccacc cagactgtgg tattttgtta tagcagcctg aacagactaa   1860
gacgggggtg ttgcttccat caaaggatgt actaagttgt ggattatttg tgaaattgaa   1920
ttacaacctt tccttaagg  tcttttacca cctccccccc aaaaaaatcc cccaaaactg   1980
attcagattt tcatacttta atgaaatatt ttataatttg caaattttta agtaatttat   2040
gaaaaaccta gatcagtgga tctcctctct ggctgcccat tagaatgtcc tgtggagatt   2100 aaacttttt  ttttcagttt atggaccaag agttttgatt tatttagggt ggagttcagg   2160
atcagaatgg tttcagaagc tcccaggtga ttccggagtg agttggagct gcaagccccct   2220 gagctagatt ataagatgct tctgggaaag aaccacattt taggaatttg cttcccaccc   2280
agtgccctgc atttaatcag cacctgatga cttggcagga cttgccccac cagggtctgg   2340
ctttgaaggg tagtggacac caggatcctt tggattaatc ctctgccacc tctctctttt   2400
cctcaaccga gagtgaattt atgtaattga gtgaaagtct acgaatcata attgtaataa   2460
attaaggctg ggcatttgtt tgaaattaga taggataaag ccaaaggttt gaacaagttg   2520
tggatggttt gtaaaaatta atcttacaaa ataaatgctg tgtgtgaaca cgttgattaa   2580
attcaaaaaa a                                                        2591

<210> SEQ ID NO 22
<211> LENGTH: 1141
<212> TYPE: DNA
```

<213> ORGANISM: Homo sapiens

<400> SEQUENCE: 22

| | | | | | |
|---|---|---|---|---|---|
| gttaagggct | ccgtggacat | ctcaggtctt | cagggtcttc | catctggaac | tatataaagt | 60 |
| tcagaaaaca | tgtctcgaag | atatgactcc | aggaccacta | tattttctcc | agaaggtcgc | 120 |
| ttataccaag | ttgaatatgc | catggaagct | attggacatg | caggcacctg | tttgggaatt | 180 |
| ttagcaaatg | atggtgtttt | gcttgcagca | gagagacgca | acatccacaa | gcttcttgat | 240 |
| gaagtctttt | tttctgaaaa | aatttataaa | ctcaatgagg | acatggcttg | cagtgtggca | 300 |
| ggcataactt | ctgatgctaa | tgttctgact | aatgaactaa | ggctcattgc | tcaaaggtat | 360 |
| ttattacagt | atcaggagcc | aataccttgt | gagcagttgg | ttacagcgct | gtgtgatatc | 420 |
| aaacaagctt | atacacaatt | tggaggaaaa | cgtcccttttg | tgtttcatt | gctgtacatt | 480 |
| ggctgggata | agcactatgg | ctttcagctc | tatcagagtg | accctagtgg | aaattacggg | 540 |
| ggatggaagg | ccacatgcat | tggaaataat | agcgctgcag | ctgtgtcaat | gttgaaacaa | 600 |
| gactataaag | aaggagaaat | gaccttgaag | tcagcacttg | ctttagctat | caaagtacta | 660 |
| aataagacca | tggatgttag | taaactctct | gctgaaaaag | tggaaattgc | aacactaaca | 720 |
| agagagaatg | gaaagacagt | aatcagagtt | ctcaaacaaa | agaagtgga | gcagttgatc | 780 |
| aaaaaacacg | aggaagaaga | agccaaagct | gagcgtgaga | agaaagaaaa | agaacagaaa | 840 |
| gaaaaggata | aatagaatca | gagatttttat | tactcatttg | gggcaccatt | tcagtgtaaa | 900 |
| agcagtccta | ctcttccaca | ctaggaaggc | tttactttttt | ttaactgtg | cagtgggaaa | 960 |
| ataggacatt | acatactgaa | ttgggtcctt | gtcatttctg | tccaattgaa | tactttattg | 1020 |
| taacgatgat | ggttacccctt | catggacgtc | ttaatcttcc | acacacatcc | ccttttttg | 1080 |
| gaataaaatt | tggaaaatgg | aaatgaaaaa | aaaaaaaaa | aaaaaaaaa | aaaaaaaaa | 1140 |
| a | | | | | | 1141 |

<210> SEQ ID NO 23
<211> LENGTH: 2870
<212> TYPE: DNA
<213> ORGANISM: Homo sapiens

<400> SEQUENCE: 23

| | | | | | |
|---|---|---|---|---|---|
| aggtcgcagg | cgggcgtgcg | tggagcgggg | gccgcggccg | cgccgcagag | atgtgactcg | 60 |
| ggccgaaggc | cagctggagc | gtcggcgctg | cggggccgcg | ggggtcgaat | gttcgtggca | 120 |
| tcagagagaa | agatgagagc | tcaccaggtg | ctcaccttcc | tcctgctctt | cgtgatcacc | 180 |
| tcggtggcct | ctgaaaacgc | cagcacatcc | cgaggctgtg | ggctggacct | cctccctcag | 240 |
| tacgtgtccc | tgtgcgacct | ggacgccatc | tgggcattg | tggtggaggc | ggtggccggg | 300 |
| gcgggcgccc | tgatcacact | gctcctgatg | ctcatcctcc | tggtgcggct | gcccttcatc | 360 |
| aaggagaagg | agaagaagag | ccctgtgggc | ctccactttc | tgttcctcct | ggggaccctg | 420 |
| ggcctctttg | ggctgacgtt | tgccttcatc | atccaggagg | acgagaccat | ctgctctgtc | 480 |
| cgccgcttcc | tctggggcgt | cctctttgcg | ctctgcttct | cctgcctgct | gagccaggca | 540 |
| tggcgcgtgc | ggaggctggt | gcggcatggc | acgggccccg | cgggctggca | gctggtgggc | 600 |
| ctggcgctgt | gcctgatgct | ggtgcaagtc | atcatcgctg | tggagtggct | ggtgctcacc | 660 |
| gtgctgcgtg | acacaaggcc | agcctgcgcc | tacgagccca | tggactttgt | gatggccctc | 720 |
| atctacgaca | tggtactgct | tgtggtcacc | ctggggctgg | ccctcttcac | tctgtgcggc | 780 |
| aagttcaaga | ggtggaagct | gaacggggcc | ttcctcctca | tcacagcctt | cctctctgtg | 840 |

-continued

```
ctcatctggg tggcctggat gaccatgtac ctcttcggca atgtcaagct gcagcagggg      900
gatgcctgga acgaccccac cttggccatc acgctggcgg ccagcggctg ggtcttcgtc      960
atcttccacg ccatccctga gatccactgc acccttctgc cagccctgca ggagaacacg     1020
cccaactact tcgacacgtc gcagcccagg atgcgggaga cggccttcga ggaggacgtg     1080
cagctgccgc gggcctatat ggagaacaag gccttctcca tggatgaaca caatgcagct     1140
ctccgaacag caggatttcc caacggcagc ttgggaaaaa gacccagtgg cagcttgggg     1200
aaaagaccca cgctccgtt tagaagcaac gtgtatcagc caactgagat ggccgtcgtg      1260
ctcaacggtg ggaccatccc aactgctccg ccaagtcaca caggaagaca ccttggtga     1320
aagactttaa gttccagaga tcagaattt ctcttaccga tttgcctccc tggctgtgtc      1380
tttcttgagg gagaaatcgg taacagttgc cgaaccaggc cgcctcacag ccaggaaatt     1440
tggaaatcct agccaagggg atttcgtgta aatgtgaaca ctgacgaact gaaaagctaa     1500
caccgactgc ccgcccctcc cctgccacac acacagacac gtaataccag accaacctca     1560
atccccgcaa actaaagcaa agctaattgc aaatagtatt aggctcactg gaaaatgtgg     1620
ctgggaagac tgtttcatcc tctggggta gaacagaacc aaattcacag ctggtgggcc      1680
agactggtgt tggttggagg tggggggctc ccactcttat cacctctccc cagcaagtgc     1740
tggaccccag gtagcctctt ggagatgacc gttgcgttga ggacaaatgg ggactttgcc     1800
accggcttgc ctggtggttt gcacatttca gggggtcag agagttaag gaggttgtgg       1860
gtgggattcc aaggtgaggc ccaactgaat cgtgggtga gctttatagc cagtagaggt      1920
ggagggaccc tggcatgtgc caaagaagag gccctctggg tgatgaagtg accatcacat     1980
ttggaaagtg atcaaccact gttccttcta tggggctctt gctctaatgt ctatggtgag     2040
aacacaggcc ccgccccttc ccttgtagag ccatagaaat attctggctt ggggcagcag     2100
tcccttcttc ccttgatcat ctcgccctgt cctacacctt acgggtgtat ctccaaatcc     2160
tctcccaatt ttattccctt attcatttca agagctccaa tggggtctcc agctgaaagc     2220
ccctccggga ggcaggttgg aaggcaggca ccacggcagg ttttccgcga tgatgtcacc     2280
tagcagggct tcaggggttc ccactaggat gcagagatga cctctcgctg cctcacaagc     2340
agtgacacct cgggtccttt ccgttgctat ggtgaaaatt cctggatgga atggatcaca     2400
tgagggtttc ttgttgcttt tggagggtgt gggggatatt tgttttggt ttttctgcag      2460
gttccatgaa aacagccctt ttccaagccc attgttctg tcatggtttc catctgtcct      2520
gagcaagtca ttcctttgtt atttagcatt tcgaacatct cggccattca aagcccccat     2580
gttctctgca ctgtttggcc agcataacct ctagcatcga ttcaaagcag agttttaacc     2640
tgacggcatg gaatgtataa atgagggtgg gtccttctgc agatactcta atcactacat     2700
tgcttttct ataaaactac ccataagcct ttaaccttta aagaaaaatg aaaaaggtta      2760
gtgtttgggg gccggggag gactgaccgc ttcataagcc agtacgtctg agctgagtat      2820
gtttcaataa accttttgat atttctcaaa aaaaaaaaa aaaaaaaaa                  2870
```

<210> SEQ ID NO 24
<211> LENGTH: 2448
<212> TYPE: DNA
<213> ORGANISM: Homo sapiens

<400> SEQUENCE: 24

```
attcccatgg ctggccagag gaggaacgct ttgtgttctc atcggagctg catgggaagt       60
```

```
ctgcatacag caaagtgacc tgcatgcctc accttatgga aaggatggtg ggctctggcc    120
tcctgtggct ggccttggtc tcctgcattc tgacccaggc atctgcagtg cagcgaggtt    180
atggaaaccc cattgaagcc agttcgtatg ggctggacct ggactgcgga gctcctggca    240
ccccagaggc tcatgtctgt tttgaccct gtcagaatta caccctcctg gatgaaccct     300
tccgaagcac agagaactca gcagggtccc aggggtgcga taaaaacatg agcggctggt    360
accgctttgt aggggaagga ggagtaagga tgtcggagac ctgtgtccag gtgcaccgat    420
gccagacaga cgctcccatg tggctgaatg ggacccaccc tgcccttggg gatggcatca    480
ccaaccacac tgcctgtgcc cattggagtg caactgctg tttctggaaa acagaggtgc     540
tggtgaaggc ctgcccaggc gggtaccatg tgtaccggtt ggaaggcact ccctggtgta    600
atctgagata ctgcacagtt ccacgagacc catccactgt ggaggacaag tgtgagaagg    660
cctgccgccc cgaggaggag tgccttgccc tcaacagcac ctgggctgt tcctgcagac     720 aggacctcaa tagttctgat gtccacagtt tgcagcctca gctagactgt gggcccaggg    780
agatcaaggt gaaggtggac aaatgtttgc tgggaggcct gggtttgggg gaggaggtca    840
ttgcctacct gcgagaccca aactgcagca gcatcttgca gacagaggag aggaactggg    900
tatctgtgac cagccccgtc caggctagtg cctgcaggaa cattctggag agaaatcaaa    960
cccatgccat ctacaaaaac accctctcct tggtcaatga tttcatcatc agagacacca    1020
tcctcaacat caacttccaa tgtgcctacc cactggacat gaaagtcagc ctccaagctg    1080
ccttgcagcc cattgtaagt tccctgaacg tcagtgtgga cgggaatgga gagttcattg    1140
tcaggatggc cctcttccaa gaccagaact acacgaatcc ttacgaaggg gatgcagttg    1200
aactgtctgt tgagtccgtg ctgtatgtgg gtgccatctt ggaacaaggg gacacctccc    1260
ggtttaacct ggtgttgagg aactgctatg ccaccccac tgaagacaag gctgaccttg     1320
tgaagtattt catcatcaga aacagctgct caaatcaacg tgattccacc atccacgtgg    1380
aggagaatgg gcagtcctcg gaaagccggt tctcagttca gatgttcatg tttgctggac    1440
attatgacct agttttcctg cattgtgaga ttcatctctg tgattctctt aatgaacagt    1500
gccagccttc ttgctcaaga agtcaagtcc gcagtgaagt accggccatc gacctagccc    1560
gggttctaga tttgggggccc atcactcgga gaggtgcaca gtctcccggt gtcatgaatg    1620 gaaccctag cactgcaggg ttcctggtgg cctggcctat ggtcctcctg actgtcctcc     1680
tggcttggct gttctgagag ctccgctgag catctggcct tgaagtttgt gttcttccct    1740
ctggcaatgg ctcccttcag cacttctgct ttccactcca attcacacag gcttggtatt    1800
aacagaatca aggccaggct aggttaggaa aagggaagag ctttcacctt ctttaaaact    1860
ctcggctggg cgcagtggct catgcctgta atcccagcat tttgggaggc tgaggcaggt    1920
ggatcacctg aggtcagcag ttcaaaatca gcctggccaa aatgctgaaa ctccgtctct    1980
actaaaaata caaaaattag ccaggcatgg tggcaggcgc ctgtaatccc agctactcgg    2040
gaggccaagg caggagaatt gctcgaactc aggggtgga ggttgcagtg agttgagatt      2100
gtgccattgc actccagcct gggcaacaga gcaagactct gtctcaggaa aaaaaaaaa     2160 aaaaaagaaa agcaacatag tggggtttct gtcaatctgt cctcggctgc ccttctcatt    2220
tgttgatggg accttgaaag caagcttgct aggtgccctc tgtggctcca gcctttaccg    2280
gaagtgtggt gcatgttttt aacttcaggg aagcggtatc ctgtcactgg ggtatgggat    2340
gagcatggag aagaggcacc agccacgatt ccttcctaag catctcctgt tctgactgct    2400
catgaattga agaaactgac ccttgtgttc aaaaaaaaaa aaaaaaaa              2448
```

<210> SEQ ID NO 25
<211> LENGTH: 2264
<212> TYPE: DNA
<213> ORGANISM: Homo sapiens

<400> SEQUENCE: 25

| | | | | | |
|---|---|---|---|---|---|
| agactaactc | tacctttctg | gcttcaggtg | ctatctagac | ctgaagtagc | gggaagagca | 60 |
| gaaaggatgg | ggcagccatc | tctgacttgg | atgctgatgg | tggtggtggc | ctcttggttc | 120 |
| atcacaactg | cagccactga | cacctcagaa | gcaagatggt | gctctgaatg | tcacagcaat | 180 |
| gccacctgca | cggaggatga | ggccgttacg | acgtgcacct | gtcaggaggg | cttcaccggc | 240 |
| gatggcctga | cctgcgtgga | cctggatgag | tgcgccattc | ctggagctca | caactgctcc | 300 |
| gccaacagca | gctgcgtaaa | cacgccaggc | tccttctcct | gcgtctgccc | cgaaggcttc | 360 |
| cgcctgtcgc | ccggtctcgg | ctgcacagac | gtggatgagt | gcgctgagcc | tgggcttagc | 420 |
| cactgccacg | ccctggccac | atgtgtcaat | gtggtgggca | gctacttgtg | cgtatgcccc | 480 |
| gcgggctacc | gggggatgg | atggcactgt | gagtgctccc | cggctcctg | cgggccgggg | 540 |
| ttggactgcg | tgcccgaggg | cgacgcgctc | gtgtgcgcgg | atccgtgcca | ggcgcaccgc | 600 |
| accctggacg | agtactggcg | cagcaccgag | tacgggagg | gctacgcctg | cgacacggac | 660 |
| ctgcgcggct | ggtaccgctt | cgtgggccag | ggcggtgcgc | gcatggccga | gacctgcgtg | 720 |
| ccagtcctgc | gctgcaacac | ggccgccccc | atgtggctca | atggcacgca | tccgtccagc | 780 |
| gacgagggca | tcgtgagccg | caaggcctgc | gcgcactgga | gcggccactg | ctgcctgtgg | 840 |
| gatgcgtccg | tccaggtgaa | ggcctgtgcc | ggcggctact | acgtctacaa | cctgacagcg | 900 |
| cccccgagt | gtcacctggc | gtactgcaca | gaccccagct | ccgtgggg | gacgtgtgag | 960 |
| gagtgcagta | tagacgagga | ctgcaaatcg | aataatggca | gatggcactg | ccagtgcaaa | 1020 |
| caggacttca | acatcactga | tatctcccctc | ctggagcaca | ggctggaatg | tggggccaat | 1080 |
| gacatgaagg | tgtcgctggg | caagtgccag | ctgaagagtc | tgggcttcga | caaggtcttc | 1140 |
| atgtacctga | gtgacagccg | gtgctcgggc | ttcaatgaca | gagacaaccg | ggactgggtg | 1200 |
| tctgtagtga | ccccagcccg | ggatggcccc | tgtgggacag | tgttgacgag | gaatgaaacc | 1260 |
| catgccactt | acagcaacac | cctctacctg | gcagatgaga | tcatcatccg | tgacctcaac | 1320 |
| atcaaaatca | actttgcatg | ctcctacccc | ctggacatga | aagtcagcct | gaagaccgcc | 1380 |
| ctacagccaa | tggtcagtgc | tctaaacatc | agagtgggcg | gaccggcat | gttcaccgtg | 1440 |
| cggatggcgc | tcttccagac | cccttcctac | acgcagccct | accaaggctc | ctccgtgaca | 1500 |
| ctgtccactg | aggcttttct | ctacgtgggc | accatgttgg | atggggcga | cctgtcccga | 1560 |
| tttgcactgc | tcatgaccaa | ctgctatgcc | acacccagta | gcaatgccac | ggaccccctg | 1620 |
| aagtacttca | tcatccagga | cagatgccca | cacactagag | actcaactat | ccaagtggtg | 1680 |
| gagaatgggg | agtcctccca | gggccgattt | tccgtccaga | tgttccggtt | tgctggaaac | 1740 |
| tatgacctag | tctacctgca | ctgtgaagtc | tatctctgtg | acaccatgaa | tgaaaagtgc | 1800 |
| aagcctacct | gctctgggac | cagattccga | agtgggagtg | tcatagatca | atcccgtgtc | 1860 |
| ctgaacttgg | gtcccatcac | acggaaaggt | gtccaggcca | cagtctcaag | gcttttagc | 1920 |
| agcttggggc | tcctgaaagt | ctggctgcct | ctgcttctct | cggccacctt | gaccctgact | 1980 |
| tttcagtgac | tgacagcgga | aagccctgtg | ctccatggct | gccatctcac | ctcctgctgg | 2040 |
| gcaggggca | tgatgcgggc | cagtgctcca | gccacagaaa | agaaagttca | tgctttgttc | 2100 |

-continued

```
agcctgcctt cttttctccc ttttaatcct ggctgtcgag aaacagcctg tgtctttaaa    2160
tgctgctttt tctcaaaatg ggacttgtga cggtgtacct gaggccccca tctccttaaa    2220
gagtgtggca aaataatgat ttttaaatct caaaaaaaaa aaaa                     2264

<210> SEQ ID NO 26
<211> LENGTH: 1945
<212> TYPE: DNA
<213> ORGANISM: Homo sapiens

<400> SEQUENCE: 26
agccatctct tcccaaggca ggtggtgact tgagaactct gtgcctggtt tctgaggact      60
gtttcaccat gcagtggcta atgaggttcc ggaccctctg gggcatccac aaatccttcc     120
acaacatcca ccctgcccct tcacagctgc gctgccggtc tttatcagaa tttggagccc     180
caagatggaa tgactatgaa gtaccggagg aatttaactt tgcaagttat gtactggact     240
actgggctca aaaggagaag gagggcaaga gaggtccaaa tccagctttt tggtgggtga     300
atggccaagg ggatgaagta aagtggagct tcagagagat gggagaccta acccgccgtg     360
tagccaacgt cttcacacag acctgtggcc tacaacaggg agaccatctg gccttgatgc     420
tgcctcgagt tcctgagtgg tggctggtgg ctgtgggctg catgcgaaca gggatcatct     480
tcattcctgc gaccatcctg ttgaaggcca aagacattct ctatcgacta cagttgtcta     540
aagccaaggg cattgtgacc atagatgccc ttgcctcaga ggtggactcc atagcttctc     600
agtgcccctc tctgaaaacc aagctcctgg tgtctgatca cagccgtgaa gggtggctgg     660
acttccgatc gctggttaaa tcagcatccc cagaacacac ctgtgttaag tcaaagacct     720
tggacccaat ggtcatcttc ttcaccagtg ggaccacagg cttccccaag atggcaaaac     780
actcccatgg gttggcctta caaccctcct tcccaggaag taggaaatta cggagcctga     840
agacatctga tgtctcctgg tgcctgtcgg actcaggatg gattgtggct accatttgga     900
ccctggtaga accatggaca gcgggttgta cagtctttat ccaccatctg ccacagtttg     960
acaccaaggt catcatacag acattgttga aataccccat taaccacttt tgggggggtat    1020 catctatata tcgaatgatt ctgcagcagg atttcaccag catcaggttc cctgccctgg    1080
agcactgcta tactggcggg gaggtcgtgt tgcccaagga tcaggaggag tggaaaagac    1140
ggacgggcct tctgctctac gagaactatg ggcagtcgga aacgggacta atttgtgcca    1200
cctactgggg aatgaagatc aagccgggtt tcatggggaa ggccactcca ccctatgacg    1260
tccaggtcat tgatgacaag ggcagcatcc tgccacctaa cacagaagga aacattggca    1320
tcagaatcaa acctgtcagg cctgtgagcc tcttcatgtg ctatgagggt gacccagaga    1380
agacagctaa agtggaatgt ggggacttct acaaacactgg ggacagagga aagatggatg    1440
aagagggcta catttgtttc ctggggagga gtgatgacat cattaatgcc tctgggtatc    1500
gcatcgggcc tgcagaggtt gaaagcgctt ggtggagcca cccagcggtg gcggagtcag    1560
ccgtggtggg cagcccagac ccgattcgag gggaggtggt gaaggccttt attgtcctga    1620
ccccacagtt cctgtcccat gacaaggatc agctgaccaa ggaactgcag cagcatgtca    1680
agtcagtgac agccccatac aagtacccaa ggaacgtgga gtttgtctca gagctgccaa    1740
aaaccatcac tggcaagatt gaacggaagg aacttcggaa aaaggagact ggtcagatgt    1800
aatcggcagt gaactcagaa cgcactgcac acctaaggca aatccctggc cactttagtc    1860
tccccactat ggtgaggacg agggtggggc attgagagtg ttgatttggg aaagtatcag    1920
gagtgccata atcactagtg aattc                                          1945
```

<210> SEQ ID NO 27
<211> LENGTH: 930
<212> TYPE: DNA
<213> ORGANISM: Mus musculus

<400> SEQUENCE: 27

| | | | | | |
|---|---|---|---|---|---|
| atggagaacc | aaaacaatgt | gacagaattt | atccttctgg | gactcacaga | gaacccaaag | 60 |
| atgcaaaaaa | ttgtattcat | tatgttttt | cttatctaca | tcatttctat | aacaggaaat | 120 |
| gtgctcattg | tggtcaccat | aacttctacg | tcattattag | agtcccccat | gtacttttc | 180 |
| ctggcttatc | tatcctttat | tgatgcttgc | tattcctctg | ttagcacccc | taaactgata | 240 |
| gcagattcac | tctgtgaaaa | gaagaccatc | ccatttaatg | gatgcatgac | tcagatcttt | 300 |
| ggggagcatt | tgtttggagg | tgctgaaatc | atcctgctga | cagtaatggc | ctatgaccgc | 360 |
| tatgtggcca | tctgcaaacc | ccttcattat | gcaacgatca | tgagtcgaag | actatgtagc | 420 |
| ctgctagtgg | gagtgtcatg | gctaggaggt | tttcttcatg | ccaccataca | gatcctgttc | 480 |
| attttccaat | acccttctg | tggccctaac | atcatagatc | attttatgtg | tgatcttaat | 540 |
| cctttgctca | accttgtatg | caccgatact | cacactcttg | gaatctttgt | tgcagccaac | 600 |
| agtggtttta | tttgtctgct | aaacttcctt | cttctattgg | tctcctatgt | tgccatcctg | 660 |
| cgctccctaa | agaaccacag | tgcagaggga | aggcgcaaag | ccctctctac | ctgtatttca | 720 |
| cacataacag | tggttgtctt | attctttgtg | ccttgcatat | ttgtatacat | gagacctgta | 780 |
| gctaccttac | ccattgataa | agcagttgct | atgttctata | ctatgataac | tcccatgttg | 840 |
| aaccccttaa | tctataccett | aagaaatgct | cagatgaaag | atgccattaa | gaaattgggt | 900 |
| agcactaaaa | ttctttcaag | taataaatga | | | | 930 |

<210> SEQ ID NO 28
<211> LENGTH: 2591
<212> TYPE: DNA
<213> ORGANISM: Homo sapiens

<400> SEQUENCE: 28

| | | | | | |
|---|---|---|---|---|---|
| gccaagggca | ctattggcca | gttccgttca | acgaagtggt | tgcttttttt | agttccggca | 60 |
| atgagttgcg | ccggggcggc | ggcggctccc | cgcctttggc | ggctgcgccc | ggggccccgg | 120 |
| cggtccctct | cagcttatgg | aagaagaacc | agtgtcagat | ttcgcagttc | aggaatgact | 180 |
| ttagacaata | tcagtcgggc | agctgtggat | cgaataatcc | gggtggatca | tgcaggcgaa | 240 |
| tatggagcaa | accgcatcta | tgccgggcag | atggctgtcc | tgggtcggac | cagcgtcggg | 300 |
| ccagtcattc | agaaaatgtg | ggatcaagaa | aaggaccatt | tgaaaaagtt | caatgagttg | 360 |
| atggttacgt | tcagggtccg | gccaacagtt | ctgatgccct | tgtggaacgt | gctgggtttt | 420 |
| gcactggggg | cggggaccgc | cttgctcggg | aaggaaggtg | ccatggcctg | caccgtggcg | 480 |
| gtggaagaga | gcatagcaca | tcactacaac | aaccagatca | ggacgctgat | ggaggaggac | 540 |
| cctgaaaaat | acgaggaact | tcttcagctg | ataaagaaat | tcgggatga | agagcttgag | 600 |
| caccatgaca | taggcctcga | ccatgatgca | gaattggctc | cagcctatgc | cgtcctgaag | 660 |
| agcattatcc | aggccggatg | cagagtggcg | atatatttat | cagaaagatt | ataaagtgtg | 720 |
| tccagttttg | cctgtctata | aaagatgata | gtaatttacc | aagtgacatt | tgcagagaaa | 780 |
| caggtgtaca | gttatcgttg | tactttgta | caatgtgaat | tttgttaata | aattataagg | 840 |
| tttgttttt | tttttttaaa | ctctgcagtg | ttgatttttc | tctgggttgt | ttttctgcc | 900 |

| | |
|---|---|
| atgagaccaa caggtcacca gccttgttca agttacagca aacgaagctg ggccttgttt | 960 |
| ggtctcatac ttaattttct tttatataca tgttttctt ttacatgcat atatatatat | 1020 |
| tttattttat tttatgtttt ttggagacag ggcctcgctc ttttgtccag gccgggtcac | 1080 |
| aactcactgc agcctggacc tcctagcctc aagcaatcca cccacctcag ccttccaagt | 1140 |
| agctgggact acaggtgtgc accaccacag ctggctaatt ctatttttt atagaggcga | 1200 |
| agtctcacta tgtcgccagg ctggtctcta actcctgggc tcagtgatcc tcccgtttcg | 1260 |
| acttcccaaa gtgctgggat tacaggtgtg agccacttca ccaggcccat tttctcctaa | 1320 |
| aacttcaagg acaaatcatt aataatgtaa caggaatctt taggagaaaa aacaatttgg | 1380 |
| tttactgata acaaaagata attggaaaca tgagagtatt tgagattggc caagcagaac | 1440 |
| tatgaagtcc atcaagtaag tcaaagatca tcgtttctgt tttgaattgt gggtgataat | 1500 |
| gggtgggaga gtgctacagt ctgtatgtct gtgtctccct agaattcata cgatgaaatc | 1560 |
| ttcactctca agttgataga aggtgggggcc cttgggaagt gtgaggtcat gagagtggag | 1620 |
| ccctcatgaa tgggatcagt gccttatgaa aggccctaga gagataccta tccttctccca | 1680 |
| cagtgtgaga cttcaagggg aagtatgaga cttctctgag gaagcagacc cttcacaagc | 1740 |
| aaaatcagcc agcactttga tcacggactt cccagcctct aggactgtga gcaataaatg | 1800 |
| tttgatgttt ataagccacc cagactgtgg tatttgtta tagcagcctg aacagactaa | 1860 |
| gacgggggtg ttgcttccat caaaggatgt actaagttgt ggattatttg tgaaattgaa | 1920 |
| ttacaacctt ttccttaagg tcttttacca cctccccccc aaaaaaatcc cccaaaactg | 1980 |
| attcagattt tcatacttta atgaaatatt ttataatttg caaattttta agtaatttat | 2040 |
| gaaaaaccta gatcagtgga tctcctctct ggctgcccat tagaatgtcc tgtggagatt | 2100 |
| aaactttttt ttttcagttt atggaccaag agttttgatt tatttagggt ggagttcagg | 2160 |
| atcagaatgg tttcagaagc tcccaggtga ttccggagtg agttggagct gcaagcccct | 2220 |
| gagctagatt ataagatgct tctgggaaag aaccacattt taggaatttg cttcccaccc | 2280 |
| agtgccctgc atttaatcag cacctgatga cttggcagga cttgcccac cagggtctgg | 2340 |
| cttttgaaggg tagtggacac caggatcctt tggattaatc ctctgccacc tctctctttt | 2400 |
| cctcaaccga gagtgaattt atgtaattga gtgaaagtct acgaatcata attgtaataa | 2460 |
| attaaggctg ggcatttgtt tgaaattaga taggataaag ccaaaggttt gaacaagttg | 2520 |
| tggatggttt gtaaaaatta atcttacaaa ataaatgctg tgtgtgaaca cgttgattaa | 2580 |
| attcaaaaaa a | 2591 |

<210> SEQ ID NO 29
<211> LENGTH: 1912
<212> TYPE: DNA
<213> ORGANISM: Homo sapiens

<400> SEQUENCE: 29

| | |
|---|---|
| cccaggcgcc ccggccttat tccagcctgg ggagcgcctc ggtggggagc acgggacagc | 60 |
| gagggaggcc gaggcggggg ccctgggcgc ccgatatctc cgaaccgggg aggcggcccc | 120 |
| gattccgaga gccggaacgc agggaaaggc aaggacgggg cggccggcgg aggggcgggc | 180 |
| gccgctcatc agccacgcca gtcacgtctg ggccaccgg ctgccttttt cttccttttcc | 240 |
| cccttttgctt tcttccccct ccgctgttgg cgagggcaaa gtggccgtgg cggcgccatg | 300 |
| cccgggccgg agtgagtgcg cgcgggcgaa aatggcgtac atccagttgg aaccattaaa | 360 |
| cgagggtttt ctttctagaa tctctggtct gctgctgtgc agatggacct gccggcactg | 420 |

```
ctgtcagaag tgctacgagt ccagctgttg ccagtcaagt gaggatgaag ttgaaattct    480
gggacctttc cctgctcaga cccctccctg gctgatggcc agccggagca gtgacaagga    540
tggtgactct gtccacacgg ccagcgaagt cccgctgacc ccacggacca attccccgga    600
tggaagacgc tcgtcctcag acacatccaa gtctacatac agcctgacgc ggaggatttc    660
gagtcttgag tcaagacgtc ccagctctcc actcatcgat attaaaccca tcgagtttgg    720
cgttctcagc gccaagaagg agcccatcca accttcggtg ctcagacgga cctataaccc    780
cgacgactat ttcaggaagt tcgaaccccc cctgtactcc ctcgactcca acagcgacga    840
tgtggactct ctgacagacg aggagatcct gtccaagtac cagctgggca tgctgcactt    900
cagcactcag tacgacctgc tgcacaacca cctcaccgtg cgcgtgatcg aggccaggga    960
cctgccacct cccatctccc acgatggctc gcgccaggac atggcgcact ccaaccccta   1020
cgtcaagatc tgtctcctgc cagaccgaaa gaactcaaag cagaccgggg tcaaacgcaa   1080
gacccagaag cccgtgtttg aggagcgcta caccttcgag atccccttcc tggaggccca   1140
gaggaggacc ctgctcctga ccgtggtgga ttttgataag ttctcccgcc actgtgtcat   1200
tgggaaagtt tctgtgcctt tgtgtgaagt tgacctggtc aagggcgggc actggtggaa   1260
ggcgctgatt cccagttctc agaatgaagt ggagctgggg gagctgcttc tgtcactgaa   1320
ttatctccca agtgctggca gactgaatgt tgatgtcatt cgagccaagc aacttcttca   1380
gacagatgtg agccaaggtt cagacccctt tgtgaaaatc cagctggtgc atggactcaa   1440
acttgtgaaa accaagaaga cgtccttctt aaggggcaca attgatcctt ctacaatga    1500 atccttcagc ttcaaagttc cccaagaaga actggaaaat gccagcctag tgtttacagt   1560
tttcggccac aacatgaaga gcagcaatga cttcatcggg aggatcgtca ttggccagta   1620
ctcttcaggc ccctctgaga ccaaccactg gaggcgcatg ctcaacacgc accgcacagc   1680
cgtggagcag tggcatagcc tgaggtcccg agctgagtgt gaccgcgtgt ctcctgcctc   1740
cctggaggtg acctgagggc tgcagggaag gcagctttca tttgtttaaa aaaaaaaaa    1800 aaagacggaa aaaatgtgt cacatactat tacatccaca cctgcataca cactcgcaac   1860
atgtctacac acgtccacac acacagacac acagataccc caaatcctct ca           1912

<210> SEQ ID NO 30
<211> LENGTH: 1401
<212> TYPE: DNA
<213> ORGANISM: Homo sapiens

<400> SEQUENCE: 30
atgcaaaggt ggacactgtg ggctgcagcc ttcctgaccc tccactctgc acaggccttt     60
ccacaaacag acatcagtat cagtccagcc ctgccagagc tgcccctgcc ttccctgtgc    120
cccctgttct ggatggagtt caaaggccac tgctatcgat tcttccctct caataagacc    180
tgggctgagg ccgacctcta ctgttctgag ttctctgtgg gcaggaagtc cgccaagctg    240
gcctccatcc acagctggga ggagaatgtc tttgtatatg acctcgtgaa cagctgtgtt    300
cccggcatcc cagctgacgt ctggacaggc cttcatgatc acagacagga agggcagttt    360
gaatggactg atggctcatc ctatgactac agctactggg atggcagcca gccagatgat    420
ggcgtccacg cggacccaga agaagaggac tgcgtgcaga tatggtacag gcctaccagt    480
gagcagctac aggcccccaga gccccagtta cccttatcaa tctcagaggc cacagatgtc    540
tatctccctg aggatttccc agctgagccc aagctcatgg accagtcctg ggtgtccagg    600
```

```
aagagcctga aaccatccaa gagtcatctt atggagccac ccactccagt ggccaagcac      660
caaaaggcaa agacccgaca taggagcctg cgcggcgtct ggtggccatc aggtaaggct      720
gggtcatgga agaaagaat gaatgcagac tacgggcgaa gaaagcgatc ggccccgagg       780
caggaaggcc ggctccggtg cagggagcgc cgcctgcggg ctgcttcggg ccagggtcga      840
cccgagggcc agcgcaagca gcggcaacag gagcgccagg agagaggctg ggaagaactg      900
ggaggggtgt ccccaatgcg gggcgcccaa gcgtggcagc acgggctggg agcggggagc      960
cagcggggtg cggcgccgga gtgcgggggag aaccaccagg cgccggaatt ggggagcacg     1020
tggagggggc agcggctcca gccccagacc gccgcgctct gtcactttgc attaagaaag      1080
cttccgggga atgcacacgg cctggccgcc gccttcgtgc agcccgccct gcaggtgcag      1140
gaagaaaaga ataatcgcac ccgtttctca ggtgcttact tcaccatgtc cgatccgacg      1200
tgtgaccaag atagcaagga gcagtcttta aggcgacacg cagagaggc agaaaaagat      1260 gggccttacc ggttagttaa gaaaaaaaga ggacctgttg cctgtccctc tagctttgaa      1320
ctacaaagtg gaggggaagt ttgtctggat ttcctgtag aactgagggc agggacctgg       1380
attgctcgag aacctccata a                                               1401

<210> SEQ ID NO 31
<211> LENGTH: 2870
<212> TYPE: DNA
<213> ORGANISM: Homo sapiens

<400> SEQUENCE: 31
aggtcgcagg cgggcgtgcg tggagcgggg gccgcggccg cgccgcagag atgtgactcg       60
ggccgaaggc cagctggagc gtcggcgctg cggggccgcg ggggtcgaat gttcgtggca      120
tcagagagaa agatgagagc tcaccaggtg ctcaccttcc tcctgctctt cgtgatcacc      180
tcggtggcct ctgaaaacgc cagcacatcc cgaggctgtg ggctggacct cctccctcag      240
tacgtgtccc tgtgcgacct ggacgccatc tggggcattg tggtggaggc ggtggccggg      300
gcgggcgccc tgatcacact gctcctgatg ctcatcctcc tggtgcggct gcccttcatc      360
aaggagaagg agaagaagag ccctgtgggc ctccactttc tgttcctcct ggggaccctg      420
ggcctctttg gctgacgtt tgccttcatc atccaggagg acgagaccat ctgtctgtc       480 cgccgcttcc tctgggcgt cctctttgcg ctctgcttct cctgcctgct gagccaggca      540
tggcgcgtgc ggaggctggt gcggcatggc acgggcccg cgggctggca gctggtgggc       600
ctggcgctgt gcctgatgct ggtgcaagtc atcatcgctg tggagtggct ggtgctcacc      660
gtgctgcgtg acacaaggcc agcctgcgcc tacgagccca tggactttgt gatggccctc      720
atctacgaca tggtactgct tgtggtcacc ctggggctgg ccctcttcac tctgtgcggc      780
aagttcaaga ggtggaagct gaacggggcc ttcctcctca tcacagcctt cctctctgtg      840
ctcatctggg tggcctggat gaccatgtac ctcttcggca atgtcaagct gcagcagggg      900
gatgcctgga acgaccccac cttggccatc acgctggcgg ccagcggctg ggtcttcgtc      960
atcttccacg ccatccctga gatccactgc accctcttgc cagccctgca ggagaacacg     1020
cccaactact tcgacacgtc gcagcccagg atgcgggaga cggccttcga ggaggacgtg     1080
cagctgccgc gggcctatat ggagaacaag gccttctcca tggatgaaca caatgcagct     1140
ctccgaacag caggattcc caacggcagc ttgggaaaaa gacccagtgg cagcttgggg      1200
aaaagaccca gcgctccgtt tagaagcaac gtgtatcagc aactgagat ggccgtcgtg     1260 ctcaacggtg ggaccatccc aactgctccg ccaagtcaca caggaagaca cctttggtga     1320
```

```
aagactttaa gttccagaga atcagaatttt ctcttaccga tttgcctccc tggctgtgtc    1380
tttcttgagg gagaaatcgg taacagttgc cgaaccaggc cgcctcacag ccaggaaatt    1440
tggaaatcct agccaagggg atttcgtgta aatgtgaaca ctgacgaact gaaaagctaa    1500
caccgactgc ccgcccctcc cctgccacac acacagacac gtaataccag accaacctca    1560
atccccgcaa actaaagcaa agctaattgc aaatagtatt aggctcactg gaaaatgtgg    1620
ctgggaagac tgtttcatcc tctggggggta aacagaacc aaattcacag ctggtgggcc    1680
agactggtgt tggttggagg tggggggctc ccactcttat cacctctccc cagcaagtgc    1740
tggaccccag gtagcctctt ggagatgacc gttgcgttga ggacaaatgg ggactttgcc    1800
accggcttgc ctggtggttt gcacatttca gggggggtcag gagagttaag gaggttgtgg    1860
gtgggattcc aaggtgaggc ccaactgaat cgtggggtga gctttatagc cagtagaggt    1920
ggagggaccc tggcatgtgc caaagaagag gccctctggg tgatgaagtg accatcacat    1980
ttggaaagtg atcaaccact gttccttcta tggggctctt gctctaatgt ctatggtgag    2040
aacacaggcc ccgccccttc ccttgtagag ccatagaaat attctggctt ggggcagcag    2100
tcccttcttc ccttgatcat ctcgccctgt tcctacactt acgggtgtat ctccaaatcc    2160
tctcccaatt ttattccctt attcatttca agagctccaa tggggtctcc agctgaaagc    2220
ccctccggga ggcaggttgg aaggcaggca ccacggcagg ttttccgcga tgatgtcacc    2280
tagcagggct tcaggggttc ccactaggat gcagagatga cctctcgctg cctcacaagc    2340
agtgacacct cgggtccttt ccgttgctat ggtgaaaatt cctggatgga atggatcaca    2400
tgagggtttc ttgttgcttt tggagggtgt ggggggatatt ttgttttggt ttttctgcag    2460
gttccatgaa aacagccctt ttccaagccc attgttctg tcatggtttc catctgtcct    2520
gagcaagtca ttcctttgtt atttagcatt tcgaacatct cggccattca aagcccccat    2580
gttctctgca ctgtttggcc agcataacct ctagcatcga ttcaaagcag agttttaacc    2640
tgacggcatg gaatgtataa atgagggtgg gtccttctgc agatactcta atcactacat    2700
tgcttttcct ataaaactac ccataagcct ttaacccttta aagaaaaatg aaaaaggtta    2760
gtgtttgggg gccgggggag gactgaccgc ttcataagcc agtacgtctg agctgagtat    2820
gtttcaataa accttttgat atttctcaaa aaaaaaaaa aaaaaaaaaa              2870

<210> SEQ ID NO 32
<211> LENGTH: 2439
<212> TYPE: DNA
<213> ORGANISM: Homo sapiens

<400> SEQUENCE: 32
attcccatgg ctggccagag gaggaacgct tgtgttctc atcggagctg catgggaagt      60
ctgcatacag caaagtgacc tgcatgcctc accttatgga aaggatggtg ggctctggcc    120
tcctgtggct ggccttggtc tcctgcattc tgacccaggc atctgcagtg cagcgaggtt    180
atggaaaccc cattgaagcc agttcgtatg ggctggacct ggactgcgga gctcctggca    240
ccccagaggc tcatgtctgt tttgaccct gtcagaatta caccctcctg gatgaaccct    300
tccgaagcac agagaactca gcagggtccc aggggtgcga taaaaacatg agcggctggt    360
accgctttgt aggggaagga ggagtaagga tgtcggagac ctgtgtccag gtgcaccgat    420
gccagacaga cgctcccatg tggctgaatg gacccacccc tgcccttggg gatggcatca    480
ccaaccacac tgcctgtgcc cattggagtg gcaactgctg tttctggaaa acagaggtgc    540
```

```
tggtgaaggc ctgcccaggc gggtaccatg tgtaccggtt ggaaggcact ccctggtgta        600
atctgagata ctgcacagac ccatccactg tggaggacaa gtgtgagaag gcctgccgcc        660
ccgaggagga gtgccttgcc ctcaacagca cctggggctg tttctgcaga caggacctca        720
atagttctga tgtccacagt tgcagcctc agctagactg tgggcccagg gagatcaagg         780
tgaaggtgga caaatgtttg ctgggaggcc tgggtttggg ggaggaggtc attgcctacc        840
tgcgagaccc aaactgcagc agcatcttgc agacagagga gaggaactgg gtatctgtga       900
ccagccccgt ccaggctagt gcctgcagga acattctgga gagaaatcaa acccatgcca       960
tctacaaaaa caccctctcc ttggtcatg atttcatcat cagagacacc atcctcaaca       1020
tcaacttcca atgtgcctac ccactggaca tgaaagtcag cctccaagct gccttgcagc      1080
ccattgtaag ttccctgaac gtcagtgtgg acgggaatgg agagttcatt gtcaggatgg      1140
ccctcttcca agaccagaac tacacgaatc cttacgaagg ggatgcagtt gaactgtctg     1200
ttgagtccgt gctgtatgtg ggtgccatct ggaacaagg gacacctcc cggtttaacc      1260 tggtgttgag gaactgctat gccacccca ctgaagacaa ggctgacctt gtgaagtatt      1320
tcatcatcag aaacagctgc tcaaatcaac gtgattccac catccacgtg gaggagaatg    1380
ggcagtcctc ggaaagccgg ttctcagttc agatgttcat gtttgctgga cattatgacc    1440
tagttttcct gcattgtgag attcatctct gtgattctct taatgaacag tgccagcctt    1500
cttgctcaag aagtcaagtc cgcagtgaag taccggccat cgacctagcc cgggttctag   1560
atttggggcc catcactcgg agaggtgcac agtctcccgg tgtcatgaat ggaaccccta   1620
gcactgcagg gttcctggtg gcctggccta tggtcctcct gactgtcctc ctggcttggc   1680
tgttctgaga gctccgctga gcatctggcc ttgaagtttg tgttcttccc tctggcaatg  1740
gctcccttca gcacttctgc tttccactcc aattcacaca ggcttggtat aacagaatc    1800 aaggccaggc taggttagga aaagggaaga gctttcacct tctttaaaac tctcggctgg   1860
gcgcagtggc tcatgcctgt aatcccagca ttttgggagg ctgaggcagg tggatcacct  1920
gaggtcagca gttcaaaatc agcctggcca aaatgctgaa actccgtctc tactaaaaat   1980
acaaaaatta gccaggcatg gtggcaggcg cctgtaatcc cagctactcg ggaggccaag  2040
gcaggagaat tgctcgaact cagggggtgg aggttgcagt gagttgagat tgtgccattg  2100
cactccagcc tgggcaacag agcaagactc tgtctcagga aaaaaaaaa aaaaaagaa    2160 aagcaacata gtggggtttc tgtcaatctg tcctcggctg cccttctcat tgttgatgg   2220 gaccttgaaa gcaagcttgc taggtgccct ctgtggctcc agcctttacc ggaagtgtgg  2280
tgcatgtttt taacttcagg gaagcggtat cctgtcactg gggtatggga tgagcatgga  2340
gaagaggcac cagccacgat tccttcctaa gcatctcctg ttctgactgc tcatgaattg  2400
aagaaactga cccttgtgtt caaaaaaaaa aaaaaaaa                          2439
```

<210> SEQ ID NO 33
<211> LENGTH: 2327
<212> TYPE: DNA
<213> ORGANISM: Homo sapiens

<400> SEQUENCE: 33

```
agactaactc tacctttctg gcttcaggac accagacatc agagacagag agaaaaattc        60
aaagggccaa cccgtctttc ctttgggcag gtgctatcta gacctgaagt agcgggaaga      120
gcagaaagga tggggcagcc atctctgact tggatgctga tggtggtggt ggcctcttgg      180
ttcatcacaa ctgcagccac tgacacctca gaagcaagat ggtgctctga atgtcacagc     240
```

-continued

```
aatgccacct gcacggagga tgaggccgtt acgacgtgca cctgtcagga gggcttcacc    300
ggcgatggcc tgacctgcgt ggacctggat gagtgcgcca ttcctggagc tcacaactgc    360
tccgccaaca gcagctgcgt aaacacgcca ggctccttct cctgcgtctg ccccgaaggc    420
ttccgcctgt cgcccggtct cggctgcaca gacgtggatg agtgcgctga gcctgggctt    480
agccactgcc acgccctggc cacatgtgtc aatgtggtgg gcagctactt gtgcgtatgc    540
cccgcgggct accgggggga tggatggcac tgtgagtgct ccccgggctc ctgcgggccg    600
gggttggact gcgtgcccga gggcgacgcg ctcgtgtgcg cggatccgtg ccaggcgcac    660
cgcaccctgg acgagtactg cgcagcacc  gagtacgggg agggctacgc ctgcgacacg    720
gacctgcgcg gctggtaccg cttcgtgggc cagggcggtg cgcgcatggc cgagacctgc    780
gtgccagtcc tgcgctgcaa cacggccgcc cccatgtggc tcaatggcac gcatccgtcc    840
agcgacgagg gcatcgtgag ccgcaaggcc tgcgcgcact ggagcggcca ctgctgcctg    900
tgggatgcgt ccgtccaggt gaaggcctgt gccggcggct actacgtcta caacctgaca    960
gcgccccccg agtgtcacct ggcgtactgc acagacccca gctccgtgga ggggacgtgt   1020
gaggagtgca gtatagacga ggactgcaaa tcgaataatg gcagatggca ctgccagtgc   1080
aaacaggact tcaacatcac tgatatctcc ctcctggagc acaggctgga atgtgggcc    1140
aatgacatga aggtgtcgct gggcaagtgc cagctgaaga gtctgggctt cgacaaggtc   1200
ttcatgtacc tgagtgacag ccggtgctcg gcttcaatg  acagagacaa ccgggactgg   1260
gtgtctgtag tgaccccagc ccgggatggc ccctgtggga cagtgttgac gaggaatgaa   1320
acccatgcca cttacagcaa cacctctac  ctggcagatg agatcatcat ccgtgacctc   1380
aacatcaaaa tcaactttgc atgctcctac ccctgaca   tgaaagtcag cctgaagacc   1440
gccctacagc caatggtcag tgctctaaac atcagagtgg gcgggaccgg catgttcacc   1500
gtgcggatgg cgctcttcca gaccccttcc tacacgcagc cctaccaagg ctcctccgtg   1560
acactgtcca ctgaggcttt tctctacgtg ggcaccatgt ggatggggg  cgacctgtcc   1620
cgatttgcac tgctcatgac caactgctat gccacaccca gtagcaatgc cacggacccc   1680
ctgaagtact tcatcatcca ggacagatgc ccacacacta gagactcaac tatccaagtg   1740
gtggagaatg gggagtcctc ccagggccga ttttccgtcc agatgttccg gtttgctgga   1800
aactatgacc tagtctacct gcactgtgaa gtctatctct gtgacaccat gaatgaaaag   1860
tgcaagccta cctgctctgg gaccagattc cgaagtggga gtgtcataga tcaatcccgt   1920
gtcctgaact tgggtcccat cacacggaaa ggtgtccagg ccacagtctc aagggctttt   1980
agcagcttgg ggctcctgaa agtctggctg cctctgcttc tctcggccac cttgaccctg   2040
acttttcagt gactgacagc ggaaagccct gtgctccatg gctgccatct cacctcctgc   2100
tgggcagggg gcatgatgcg ggccagtgct ccagccacag aaaagaaagt tcatgctttg   2160
ttcagcctgc cttcttttct cccttttaat cctggctgtc gagaaacagc ctgtgtcttt   2220
aaatgctgct ttttctcaaa atgggacttg tgacggtgta cctgaggccc ccatctcctt   2280
aaagagtgtg gcaaataat  gatttttaaa tctcaaaaaa aaaaaa                   2327
```

<210> SEQ ID NO 34
<211> LENGTH: 1945
<212> TYPE: DNA
<213> ORGANISM: Homo sapiens

<400> SEQUENCE: 34

-continued

```
agccatctct tcccaaggca ggtggtgact tgagaactct gtgcctggtt tctgaggact    60
gtttcaccat gcagtggcta atgaggttcc ggaccctctg gggcatccac aaatccttcc   120
acaacatcca ccctgcccct tcacagctgc gctgccggtc tttatcagaa tttggagccc   180
caagatggaa tgactatgaa gtaccggagg aatttaactt tgcaagttat gtactggact   240
actgggctca aaaggagaag gagggcaaga gaggtccaaa tccagctttt tggtgggtga   300
atggccaagg ggatgaagta aagtggagct tcagagagat gggagaccta acccgccgtg   360
tagccaacgt cttcacacag acctgtggcc tacaacaggg agaccatctg gccttgatgc   420
tgcctcgagt tcctgagtgg tggctggtgg ctgtgggctg catgcgaaca gggatcatct   480
tcattcctgc gaccatcctg ttgaaggcca agacattct ctatcgacta cagttgtcta   540
aagccaaggg cattgtgacc atagatgcc ttgcctcaga ggtggactcc atagcttctc   600
agtgcccctc tctgaaaacc aagctcctgg tgtctgatca cagccgtgaa gggtggctgg   660
acttccgatc gctggttaaa tcagcatccc cagaacacac ctgtgttaag tcaaagacct   720
tggacccaat ggtcatcttc ttcaccagtg ggaccacagg cttccccaag atggcaaaac   780
actcccatgg gttggcctta caaccctcct tcccaggaag taggaaatta cggagcctga   840
agacatctga tgtctcctgg tgcctgtcgg actcaggatg gattgtggct accatttgga   900
ccctggtaga accatggaca gcgggttgta cagtctttat ccaccatctg ccacagtttg   960
acaccaaggt catcatacag acattgttga aatacccat taaccacttt tgggggtat   1020
catctatata tcgaatgatt ctgcagcagg atttcaccag catcaggttc cctgccctgg   1080
agcactgcta tactggcggg gaggtcgtgt tgcccaagga tcaggaggag tggaaaagac   1140
ggacgggcct tctgctctac gagaactatg ggcagtcgga aacggactaa atttgtgcca   1200
cctactgggg aatgaagatc aagccgggtt tcatgggaa ggccactcca ccctatgacg   1260
tccaggtcat tgatgacaag ggcagcatcc tgccacctaa cacagaagga aacattggca   1320
tcagaatcaa acctgtcagg cctgtgagcc tcttcatgtg ctatgagggt gacccagaga   1380
agacagctaa agtggaatgt ggggacttct acaacactgg ggacagagga agatggatg   1440
aagagggcta catttgtttc ctggggagga gtgatgacat cattaatgcc tctgggtatc   1500
gcatcgggcc tgcagaggtt gaaagcgctt tggtggagca cccagcgtg gcggagtcag   1560
ccgtggtggg cagcccagac ccgattcgag gggaggtggt gaaggccttt attgtcctga   1620
ccccacagtt cctgtcccat gacaaggatc agctgaccaa ggaactgcag cagcatgtca   1680
agtcagtgac agccccatac aagtacccaa ggaacgtgga gtttgtctca gagctgccaa   1740
aaaccatcac tggcaagatt gaacggaagg aacttcggaa aaaggagact ggtcagatgt   1800
aatcggcagt gaactcagaa cgcactgcac acctaaggca aatccctggc cactttagtc   1860
tccccactat ggtgaggacg agggtggggc attgagagtg ttgatttggg aaagtatcag   1920
gagtgccata atcactagtg aattc                                         1945
```

<210> SEQ ID NO 35
<211> LENGTH: 24
<212> TYPE: DNA
<213> ORGANISM: Artificial
<220> FEATURE:
<223> OTHER INFORMATION: Primer

<400> SEQUENCE: 35

```
tcctgctcca aatgactgag ttct                                            24
```

```
<210> SEQ ID NO 36
<211> LENGTH: 24
<212> TYPE: DNA
<213> ORGANISM: Artificial
<220> FEATURE:
<223> OTHER INFORMATION: Primer

<400> SEQUENCE: 36
tcaacccaat ggaatgacct ctta                                              24

<210> SEQ ID NO 37
<211> LENGTH: 24
<212> TYPE: DNA
<213> ORGANISM: Artificial
<220> FEATURE:
<223> OTHER INFORMATION: Primer

<400> SEQUENCE: 37
ggtggaggct tgacatcatc agag                                              24

<210> SEQ ID NO 38
<211> LENGTH: 24
<212> TYPE: DNA
<213> ORGANISM: Artificial
<220> FEATURE:
<223> OTHER INFORMATION: Primer

<400> SEQUENCE: 38
ggaatagggc tcagatggtc tttg                                              24

<210> SEQ ID NO 39
<211> LENGTH: 24
<212> TYPE: DNA
<213> ORGANISM: Artificial
<220> FEATURE:
<223> OTHER INFORMATION: Primer

<400> SEQUENCE: 39
gccctggcct catgtgtcaa tgtg                                              24

<210> SEQ ID NO 40
<211> LENGTH: 24
<212> TYPE: DNA
<213> ORGANISM: Artificial
<220> FEATURE:
<223> OTHER INFORMATION: Primer

<400> SEQUENCE: 40
gggtcacagg gacagacaga caat                                              24

<210> SEQ ID NO 41
<211> LENGTH: 24
<212> TYPE: DNA
<213> ORGANISM: Artificial
<220> FEATURE:
<223> OTHER INFORMATION: Primer

<400> SEQUENCE: 41
cggcggctac tacgtctaca acct                                              24

<210> SEQ ID NO 42
<211> LENGTH: 24
<212> TYPE: DNA
<213> ORGANISM: Artificial
<220> FEATURE:
<223> OTHER INFORMATION: Primer
```

```
<400> SEQUENCE: 42
gtagctgccc accacattga caca                                              24

<210> SEQ ID NO 43
<211> LENGTH: 24
<212> TYPE: DNA
<213> ORGANISM: Artificial
<220> FEATURE:
<223> OTHER INFORMATION: Primer

<400> SEQUENCE: 43
acctctggac ctcaagtaat ctgt                                              24

<210> SEQ ID NO 44
<211> LENGTH: 24
<212> TYPE: DNA
<213> ORGANISM: Artificial
<220> FEATURE:
<223> OTHER INFORMATION: Primer

<400> SEQUENCE: 44
tgatgcctac tggctgagac aatc                                              24

<210> SEQ ID NO 45
<211> LENGTH: 24
<212> TYPE: DNA
<213> ORGANISM: Artificial
<220> FEATURE:
<223> OTHER INFORMATION: Primer

<400> SEQUENCE: 45
accagcagat ttagctttga agtc                                              24

<210> SEQ ID NO 46
<211> LENGTH: 25
<212> TYPE: DNA
<213> ORGANISM: Artificial
<220> FEATURE:
<223> OTHER INFORMATION: Primer

<400> SEQUENCE: 46
gcttgaacca ggcagtgctt tgacc                                             25

<210> SEQ ID NO 47
<211> LENGTH: 24
<212> TYPE: DNA
<213> ORGANISM: Artificial
<220> FEATURE:
<223> OTHER INFORMATION: Primer

<400> SEQUENCE: 47
agcagcatcc aggcacttgt caga                                              24

<210> SEQ ID NO 48
<211> LENGTH: 24
<212> TYPE: DNA
<213> ORGANISM: Artificial
<220> FEATURE:
<223> OTHER INFORMATION: Primer

<400> SEQUENCE: 48
tgaggcagaa gaatcacttg aacc                                              24

<210> SEQ ID NO 49
<211> LENGTH: 24
```

```
<212> TYPE: DNA
<213> ORGANISM: Artificial
<220> FEATURE:
<223> OTHER INFORMATION: Primer

<400> SEQUENCE: 49
tccaaagacc ccctctgaat tcta                                           24

<210> SEQ ID NO 50
<211> LENGTH: 24
<212> TYPE: DNA
<213> ORGANISM: Artificial
<220> FEATURE:
<223> OTHER INFORMATION: Primer

<400> SEQUENCE: 50
atttgaatcc aggaagtctg actc                                           24

<210> SEQ ID NO 51
<211> LENGTH: 24
<212> TYPE: DNA
<213> ORGANISM: Artificial
<220> FEATURE:
<223> OTHER INFORMATION: Primer

<400> SEQUENCE: 51
ggcaagccac tgaagttctc tgag                                           24

<210> SEQ ID NO 52
<211> LENGTH: 24
<212> TYPE: DNA
<213> ORGANISM: Artificial
<220> FEATURE:
<223> OTHER INFORMATION: Primer

<400> SEQUENCE: 52
gagcggctca gagaacttca gtgg                                           24

<210> SEQ ID NO 53
<211> LENGTH: 24
<212> TYPE: DNA
<213> ORGANISM: Artificial
<220> FEATURE:
<223> OTHER INFORMATION: Primer

<400> SEQUENCE: 53
cccgtgtcct gtgttacatt catc                                           24

<210> SEQ ID NO 54
<211> LENGTH: 24
<212> TYPE: DNA
<213> ORGANISM: Artificial
<220> FEATURE:
<223> OTHER INFORMATION: Primer

<400> SEQUENCE: 54 gagccccctga tgggtctgaa gtag                                          24

<210> SEQ ID NO 55
<211> LENGTH: 24
<212> TYPE: DNA
<213> ORGANISM: Artificial
<220> FEATURE:
<223> OTHER INFORMATION: Primer

<400> SEQUENCE: 55
```

```
tctgagccac tctccttatt taga                                          24

<210> SEQ ID NO 56
<211> LENGTH: 24
<212> TYPE: DNA
<213> ORGANISM: Artificial
<220> FEATURE:
<223> OTHER INFORMATION: Primer

<400> SEQUENCE: 56
tagattgggc acttcacaag aatg                                          24

<210> SEQ ID NO 57
<211> LENGTH: 24
<212> TYPE: DNA
<213> ORGANISM: Artificial
<220> FEATURE:
<223> OTHER INFORMATION: Primer

<400> SEQUENCE: 57
acagcagaac ccagtctcac tgag                                          24

<210> SEQ ID NO 58
<211> LENGTH: 24
<212> TYPE: DNA
<213> ORGANISM: Artificial
<220> FEATURE:
<223> OTHER INFORMATION: Primer

<400> SEQUENCE: 58
tctcacagtt ctggaggctg gaag                                          24

<210> SEQ ID NO 59
<211> LENGTH: 25
<212> TYPE: DNA
<213> ORGANISM: Artificial
<220> FEATURE:
<223> OTHER INFORMATION: Primer

<400> SEQUENCE: 59
ggtggaccct aattgcatag gattg                                         25

<210> SEQ ID NO 60
<211> LENGTH: 24
<212> TYPE: DNA
<213> ORGANISM: Artificial
<220> FEATURE:
<223> OTHER INFORMATION: Primer

<400> SEQUENCE: 60
tgtcctctag gggaagagat gtct                                          24

<210> SEQ ID NO 61
<211> LENGTH: 24
<212> TYPE: DNA
<213> ORGANISM: Artificial
<220> FEATURE:
<223> OTHER INFORMATION: Primer

<400> SEQUENCE: 61
aggtcaggga cctagtaact actc                                          24

<210> SEQ ID NO 62
<211> LENGTH: 24
<212> TYPE: DNA
<213> ORGANISM: Artificial
```

```
<220> FEATURE:
<223> OTHER INFORMATION: Primer

<400> SEQUENCE: 62
ccagagccct acaggagtgt actg                                              24

<210> SEQ ID NO 63
<211> LENGTH: 24
<212> TYPE: DNA
<213> ORGANISM: Artificial
<220> FEATURE:
<223> OTHER INFORMATION: Primer

<400> SEQUENCE: 63
caagaccagg ggatcacagt aact                                              24

<210> SEQ ID NO 64
<211> LENGTH: 21
<212> TYPE: DNA
<213> ORGANISM: Artificial
<220> FEATURE:
<223> OTHER INFORMATION: Primer

<400> SEQUENCE: 64
cagcctgggc aacagagact c                                                 21

<210> SEQ ID NO 65
<211> LENGTH: 24
<212> TYPE: DNA
<213> ORGANISM: Artificial
<220> FEATURE:
<223> OTHER INFORMATION: Primer

<400> SEQUENCE: 65
aggcgctaaa ttcagagcaa atag                                              24

<210> SEQ ID NO 66
<211> LENGTH: 24
<212> TYPE: DNA
<213> ORGANISM: Artificial
<220> FEATURE:
<223> OTHER INFORMATION: Primer

<400> SEQUENCE: 66
gctgtaatgg tgctgtgtaa atct                                              24

<210> SEQ ID NO 67
<211> LENGTH: 24
<212> TYPE: DNA
<213> ORGANISM: Artificial
<220> FEATURE:
<223> OTHER INFORMATION: Primer

<400> SEQUENCE: 67
aagaatcctc cagacttcat acac                                              24

<210> SEQ ID NO 68
<211> LENGTH: 24
<212> TYPE: DNA
<213> ORGANISM: Artificial
<220> FEATURE:
<223> OTHER INFORMATION: Primer

<400> SEQUENCE: 68
atcagcttag cagacatctc ttcc                                              24
```

```
<210> SEQ ID NO 69
<211> LENGTH: 24
<212> TYPE: DNA
<213> ORGANISM: Artificial
<220> FEATURE:
<223> OTHER INFORMATION: Primer

<400> SEQUENCE: 69
cttgtagtcc cagctactca gtgg                                          24

<210> SEQ ID NO 70
<211> LENGTH: 21
<212> TYPE: DNA
<213> ORGANISM: Artificial
<220> FEATURE:
<223> OTHER INFORMATION: Primer

<400> SEQUENCE: 70
cacgagaatc ccttgaacct g                                             21

<210> SEQ ID NO 71
<211> LENGTH: 21
<212> TYPE: DNA
<213> ORGANISM: Artificial
<220> FEATURE:
<223> OTHER INFORMATION: Primer

<400> SEQUENCE: 71
tggctctcca ctcagagatt c                                             21

<210> SEQ ID NO 72
<211> LENGTH: 24
<212> TYPE: DNA
<213> ORGANISM: Artificial
<220> FEATURE:
<223> OTHER INFORMATION: Primer

<400> SEQUENCE: 72
ctgtggctgg cttgtttcac tcag                                          24

<210> SEQ ID NO 73
<211> LENGTH: 24
<212> TYPE: DNA
<213> ORGANISM: Artificial
<220> FEATURE:
<223> OTHER INFORMATION: Primer

<400> SEQUENCE: 73
ttgggtggag gcaatccaag tgtc                                          24

<210> SEQ ID NO 74
<211> LENGTH: 24
<212> TYPE: DNA
<213> ORGANISM: Artificial
<220> FEATURE:
<223> OTHER INFORMATION: Primer

<400> SEQUENCE: 74
tgtgttattg gtgaaatgca cata                                          24

<210> SEQ ID NO 75
<211> LENGTH: 24
<212> TYPE: DNA
<213> ORGANISM: Artificial
<220> FEATURE:
<223> OTHER INFORMATION: Primer
```

```
<400> SEQUENCE: 75
ggtggctcat gcctgtaatt tgag                                          24

<210> SEQ ID NO 76
<211> LENGTH: 24
<212> TYPE: DNA
<213> ORGANISM: Artificial
<220> FEATURE:
<223> OTHER INFORMATION: Primer

<400> SEQUENCE: 76
tgacaggcac atagattatt atgc                                          24

<210> SEQ ID NO 77
<211> LENGTH: 24
<212> TYPE: DNA
<213> ORGANISM: Artificial
<220> FEATURE:
<223> OTHER INFORMATION: Primer

<400> SEQUENCE: 77
cgtacccggc tgattatttt agat                                          24

<210> SEQ ID NO 78
<211> LENGTH: 24
<212> TYPE: DNA
<213> ORGANISM: Artificial
<220> FEATURE:
<223> OTHER INFORMATION: Primer

<400> SEQUENCE: 78 agatagggt ctagtttcat tatc                                           24

<210> SEQ ID NO 79
<211> LENGTH: 24
<212> TYPE: DNA
<213> ORGANISM: Artificial
<220> FEATURE:
<223> OTHER INFORMATION: Primer

<400> SEQUENCE: 79
acaaagctgg acatatcaca ctac                                          24

<210> SEQ ID NO 80
<211> LENGTH: 24
<212> TYPE: DNA
<213> ORGANISM: Artificial
<220> FEATURE:
<223> OTHER INFORMATION: Primer

<400> SEQUENCE: 80
aggctggtct cgaactcctg acct                                          24

<210> SEQ ID NO 81
<211> LENGTH: 24
<212> TYPE: DNA
<213> ORGANISM: Artificial
<220> FEATURE:
<223> OTHER INFORMATION: Primer

<400> SEQUENCE: 81
gggactacag gtgtgtgaat ttga                                          24

<210> SEQ ID NO 82
```

```
<211> LENGTH: 24
<212> TYPE: DNA
<213> ORGANISM: Artificial
<220> FEATURE:
<223> OTHER INFORMATION: Primer

<400> SEQUENCE: 82
aggacggctg aatgtctgtc atca                                              24

<210> SEQ ID NO 83
<211> LENGTH: 24
<212> TYPE: DNA
<213> ORGANISM: Artificial
<220> FEATURE:
<223> OTHER INFORMATION: Primer

<400> SEQUENCE: 83
ttggggagtc cctaaatgac ttta                                              24

<210> SEQ ID NO 84
<211> LENGTH: 24
<212> TYPE: DNA
<213> ORGANISM: Artificial
<220> FEATURE:
<223> OTHER INFORMATION: Primer

<400> SEQUENCE: 84
ggcagaaatg gcacatctta acta                                              24

<210> SEQ ID NO 85
<211> LENGTH: 24
<212> TYPE: DNA
<213> ORGANISM: Artificial
<220> FEATURE:
<223> OTHER INFORMATION: Primer

<400> SEQUENCE: 85
cagcctgggt gacagagtga gact                                              24

<210> SEQ ID NO 86
<211> LENGTH: 24
<212> TYPE: DNA
<213> ORGANISM: Artificial
<220> FEATURE:
<223> OTHER INFORMATION: Primer

<400> SEQUENCE: 86
acccagtaga gacccatctt actc                                              24

<210> SEQ ID NO 87
<211> LENGTH: 24
<212> TYPE: DNA
<213> ORGANISM: Artificial
<220> FEATURE:
<223> OTHER INFORMATION: Primer

<400> SEQUENCE: 87
acccagtaga gacccatctt actc                                              24
```

METHOD FOR DIAGNOSING RENAL DISEASES OR PREDISPOSITIONS

CROSS-REFERENCE TO RELATED APPLICATIONS

This patent application is a continuation-in-part of PCT/US03/33957, filed on Oct. 23, 2003, and claims the benefit of U.S. Provisional Patent Application No. 60/430,318, filed on Dec. 2, 2002, and U.S. Provisional Patent Application No. 60/420,768, filed on Oct. 23, 2002. The contents of each of these applications are incorporated herein in their entirety by reference thereto.

STATEMENT REGARDING FEDERALLY SPONSORED RESEARCH AND DEVELOPMENT

This invention was made with Government support under Grant Number DK62252 awarded by the National Institute of Diabetes and Digestive and Kidney Diseases. The Government has certain rights in this invention.

FIELD OF THE INVENTION

This invention pertains to methods and reagents for diagnosing diseases or a predisposition to develop a disease.

BACKGROUND OF THE INVENTION

Medullary cystic kidney disease 2 (i.e., "MCKD2," Online Mendelian Inheritance in Man Ref. OMIN603860 and familial juvenile gouty nephropathy (i.e., "FJGN" Online Mendelian Inheritance in Man Ref. OMIM162000 are autosomal dominant renal diseases characterized by juvenile onset of hyperuricemia, gout, enuresis, and progressive renal failure. Both conditions typically result in death, unless renal transplantation is performed.

Because clinical features of both MCKD2 and FJGN vary in presence and severity, definitive diagnosis of both conditions is difficult before the onset of significant pathology. As such, currently, both conditions generally cannot be treated early, and prophylaxis typically is not possible for these conditions. Accordingly, there exists a need for a more sensitive diagnostic method and reagents for diagnosing diseases, such as MCKD2 and FJGN, or the predisposition to develop such diseases

BRIEF SUMMARY OF THE INVENTION

The invention provides a method of diagnosing a disease or a predisposition to contract a disease by assaying for mutations of uromodulin (UMOD, also known as Tamm-Horsfall glycoprotein within a test subject or patient. The presence of a mutation in the UMOD supports a diagnosis of a disease or a predisposition to contract a disease within the patient.

The inventive method can permit diagnosis of diseases (e.g., MCKD2, FJGN, nephropathy, renal failure, hyperuricemia, gouty arthritis, enuresis, and the like) earlier than current methods, which can facilitate intervention and treatment of such diseases prior to the onset of significant pathology. In some applications, the method can identify a predisposition to develop such disorders even in a non-symptomatic patient. Furthermore, the method can be employed to screen a potential tissue donor or donated tissue or organs (e.g., a kidney or renal tissue) to minimize the risk to a transplant recipient of receiving donated tissue at risk for developing such disorders. These and other advantages of the invention, as well as additional inventive features, will be apparent from the description of the invention provided herein.

BRIEF DESCRIPTION OF THE DRAWINGS

FIG. 6. Alignment of the amino acid sequence of human UMOD (GenBank accession No M17778 (SEQ ID NO:9)) with the UMOD of bovine (GenBank accession No S75958 (SEQ ID NO:10)), murine (GenBank accession No NM_009470 (SEQ ID NO:11)) and rat (GenBank accession No. M63510 (SEQ ID NO:12)). All 48 C residues are conserved and shown in bold with an asterisk. The arrows indicate the position of the missense mutations identified in this study. The 9 amino acids deleted in Family 1 are indicated in bold and underlined.

FIG. 7 depicts SEQ ID NO:1 to SEQ ID NO:8 discussed herein.

FIG. 8 depicts SEQ ID NO:9 discussed herein.
FIG. 9 depicts SEQ ID NO:10 discussed herein.
FIG. 10 depicts SEQ ID NO:11 discussed herein.
FIG. 11 depicts SEQ ID NO:12 discussed herein.
FIG. 12 depicts SEQ ID NO:13 discussed herein.
FIG. 13 depicts SEQ ID NO:14 discussed herein.
FIG. 14 depicts SEQ ID NO:15 discussed herein.
FIG. 15 depicts SEQ ID NO:16 discussed herein.
FIG. 16 depicts SEQ ID NO:17 discussed herein.
FIG. 17 depicts SEQ ID NO:18 discussed herein.
FIG. 18 depicts SEQ ID NO:19 discussed herein.
FIG. 19 depicts SEQ ID NO:20 discussed herein.
FIG. 20 depicts SEQ ID NO:21 discussed herein.
FIG. 21 depicts SEQ ID NO:22 discussed herein.
FIG. 22 depicts SEQ ID NO:23 discussed herein.
FIG. 23 depicts SEQ ID NO:24 discussed herein.
FIG. 24 depicts SEQ ID NO:25 discussed herein.
FIG. 25 depicts SEQ ID NO:26 discussed herein.
FIG. 26 depicts SEQ ID NO:27 discussed herein.
FIG. 27 depicts SEQ ID NO:28 discussed herein.
FIG. 28 depicts SEQ ID NO:29 discussed herein.
FIG. 29 depicts SEQ ID NO:30 discussed herein.
FIG. 30 depicts SEQ ID NO:31 discussed herein.
FIG. 31 depicts SEQ ID NO:32 discussed herein.
FIG. 32 depicts SEQ ID NO:33 discussed herein.
FIG. 33 depicts SEQ ID NO:34 discussed herein.
FIG. 34 depicts SEQ ID NO:35 to SEQ ID NO:57 discussed herein.
FIG. 35 depicts SEQ ID NO:58 to SEQ ID NO:87 discussed herein.

DETAILED DESCRIPTION OF THE INVENTION

The invention provides a method of diagnosing a disease or a predisposition to contract a disease by assaying for mutations of UMOD within a test subject. Any individual can be tested in accordance with the inventive method. Typically, however, the test subject (or patient) belongs to a family with a history of disorders such as, for example, MCKD2, FJGN, nephropathy, renal failure, hyperuricemia, gouty arthritis, and enuresis. Asymptomatic individuals from such families can be tested to assess whether they have a predisposition to contract such diseases or whether they might be a carrier of an allele that can cause the disease in their progeny. In fact, the method can be used prenatally to assess the propensity of a fetus to develop MCKD2, FJGN, nephropathy, renal failure, hyperuricemia, gouty arthritis, and enuresis after birth. Alternatively, the inventive method can be used to diagnose symptomatic patients, typically those exhibiting hyperuricemia, renal insufficiency, and/or enuresis. For such patients, the inventive method can provide earlier and/or more definitive diagnosis, which can facilitate earlier intervention and treatment. Furthermore, inasmuch as people in need of transplants often receive donated kidneys and other renal tissue from close relatives of family members, the inventive method can be used to screen donors or donated tissue to ensure that the recipient does not receive renal tissue that produces abnormal UMOD protein.

In one embodiment, the inventive method involves assaying genetic material obtained from a test subject. The genetic material can be, for example, DNA or RNA obtained directly from the test subject, or the genetic material can be copied or amplified from genetic material within the test subject's cells (e.g., via PCR, RT-PCR, or other suitable technique). For example, cells can be harvested from a urine sample to obtain genetic material. To ensure that sufficient quantity of genetic material is available for testing, typically genetic material amplified from cells obtained from the test subject is assayed in accordance with the inventive method. Desirably, a PCR or RT-PCR strategy is employed using primers flanking all or a portion of the UMOD gene, so as to amplify this sequence from the patient for the assay. Because MCKD2 and/or FJGN are autosomal dominant disorders, it is most preferred to amplify/copy both copies of the UMOD gene from the test subject, so that both can be assayed in accordance with the inventive method.

Figure 5:
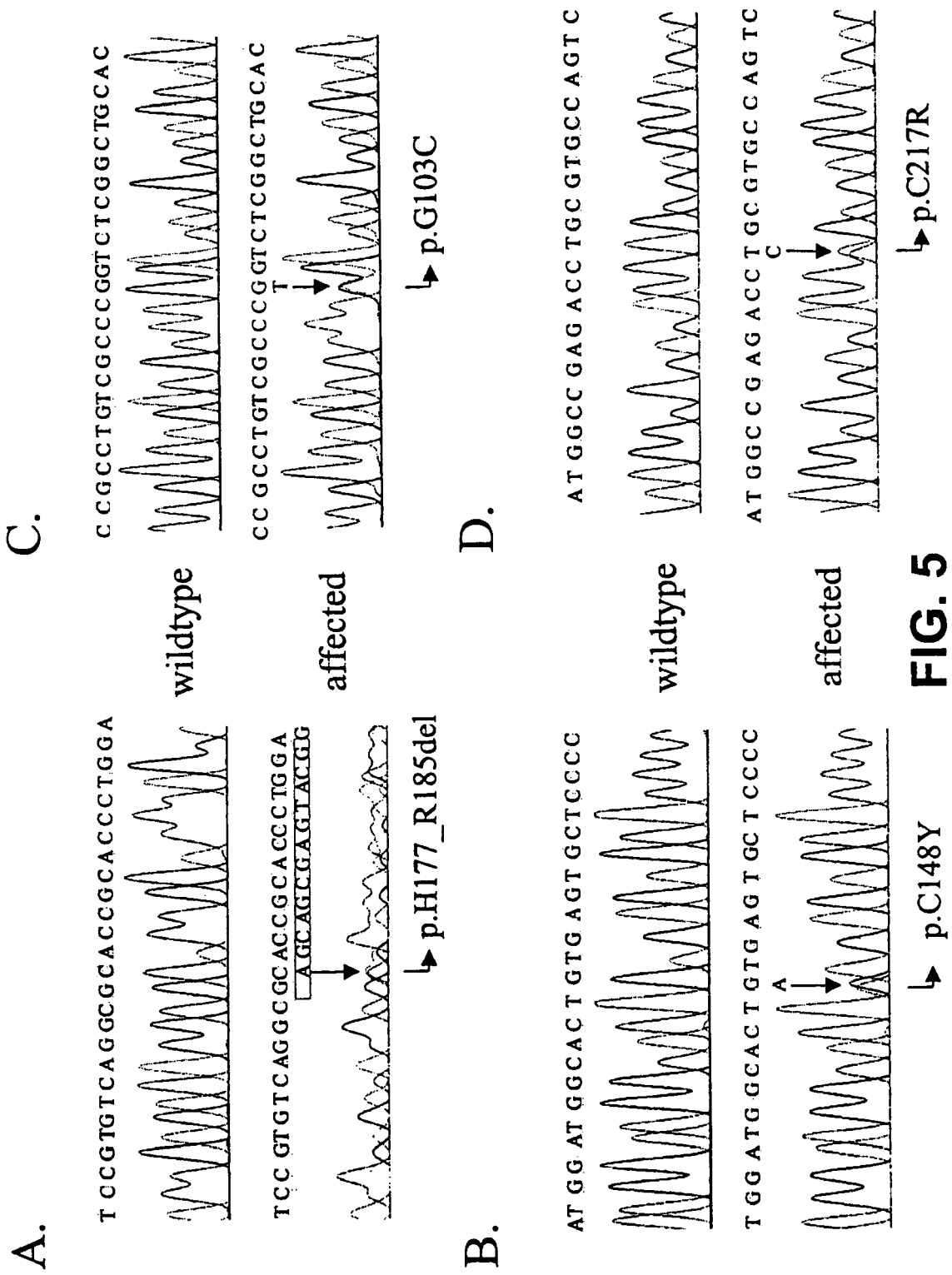
FIG. 5 diagrams mutations in the UMOD sequence. The top sequence in each panel shows wild-type sequence (SEQ ID NO:1 to SEQ ID NO:4). The bottom sequence is from an affected individual (SEQ ID NO:5 to SEQ ID NO:8). Descriptions of each mutation are given for [genomic; cDNA; protein] in accordance with nomenclature guidelines. A. Affected individuals in Family 1 were heterozygous for a 27 by deletion that results in the in-frame deletion of amino acids 177–185. [g.1966_1992del; c529_555del; p.H177_R185del]. B. Affected individuals in Family 2 were heterozygous for a missense mutation that changes a conserved cys to tyr. [g.1880G>A; c.443G>A; p.C148Y]. C. Affected individuals in Family 3 were heterozygous for a missense mutation that changes a gly to a cys. [g.1744G>T; c.307G>T; p.G103C]. D. Affected individuals in Family 4 were heterozygous for a missense mutation that changes a conserved cys to arg. [g.2086T>C; c.649T>C; p.C217R].

However obtained, the genetic material is assayed to detect a mutation in the UMOD gene (e.g., a mutation at least one of the two UMOD alleles). Any test able to detect mutations appropriate to the type of genetic material (e.g., gDNA, cDNA, RNA, etc.) can be used to this end. For example, a portion or substantially all of the genetic material can be sequenced, and the sequence compared to the wild-type UMOD sequence (see, e.g., GenBank Accession Nos. AY 162963 (SEQ ID NO:13), AY162964 (SEQ ID NO:14), AY162965 (SEQ ID NO:15), AY162967 (SEQ ID NO:16), AY162968 (SEQ ID NO:17), AY162969 (SEQ ID NO:18), and AY162970 (SEQ ID NO:19)) to detect any mutations (see, e.g., FIG. 5). Alternatively, the genetic material can be probed with a hybridization probe that is substantially specific for a predetermined UMOD mutation (e.g., via Northern or Southern hybridization, PCR, or other appropriate method, such as are well-known to those of ordinary skill in the field). For example, one known UMOD mutation associated with MCKD2 and/or FJGN is a deletion of 27 base pairs from exon 4 of the UMOD gene (see FIG. 6), and a probe designed to straddle this deletion can be employed to quickly assay for this mutation (e.g., via ELISA).

In another embodiment, the inventive method involves assaying UMOD protein obtained from the test subject. The UMOD protein can be obtained by any suitable method, such as in a urine sample or cells isolated therefrom. Thereafter, the UMOD protein obtained from the test subject is assayed to detect a mutation. For example, the UMOD protein can be purified (either partially or substantially (see, e.g., Tamm and Horsfall, *J. Exp. Med.*, 95, 71-97 (1952)) and assayed via immunohistological techniques (e.g., Western blotting, ELISA, immunoprecipitation, etc.) using one or more antibodies recognizing known mutant UMOD proteins but not wild type UMOD protein. Alternatively, or in conjunction, the UMOD protein sample from the test subject can be assayed using one or more antibodies recognizing wild type UMOD proteins but not known mutant UMOD protein. Thus, in some applications, it can be possible to develop an immunological UMOD profile of a given test subject or even quantitatively determine the amount and/or type of mutant and wild type UMOD protein present.

As an alternative to immunological characterization, protein from a test subject can be assayed morphologically. In this respect, UMOD is known to be polymeric in its native form, composed of monomeric subunits of approximately 85 kD, with 30% of the molecular weight due to carbohydrates and the remaining 70% due to the polypeptide chain (Fletcher et al., *Biochem. J.*, 120, 425-32 (1970)). Electron microscopy reveals that the high molecular weight aggregate is composed of thin, intertwining fibers with a zigzag or helical structure. Recent analysis indicates that the filaments consist of two protofilaments wound around each other, forming a right-handed helix (Jovine et al., *Nat. Cell. Biol.*, 4, 457-61 (2002)). UMOD contains a zona pelucida (ZP) domain, which has been shown to be responsible for polymerization of ZP-containing proteins into filaments (Jovine et al.). UMOD also contains a high number of cysteine residues (48 per monomer), allowing for the potential formation of 24 intramolecular disulfide bonds. These cysteine residues are highly conserved across species (FIG. 6). Mutations of the UMOD protein can alter its primary and secondary structure and ability to associate and form its typical tertiary structure. Thus, in some applications, it is possible to compare the structure of UMOD from a test subject with that of wild type protein as a morphological assay for mutant UMOD protein.

Of course, it also is possible to employ both genetic and protein assays in conjunction with each other to detect mutant UMOD within a test subject. Regardless of the method of assay, however, a test result that supports the presence of mutant or abnormal UMOD genetic material and/or protein from the test subject supports a diagnosis of MCKD2, FJGN, nephropathy, renal failure, hyperuricemia, gouty arthritis, or enuresis within the test subject, if accompanied by other symptoms consistent with such a disease. A UMOD-positive result for a non-symptomatic test subject supports a diagnosis of a predisposition to develop such a disease.

The following example further illustrates the invention but, of course, should not be construed as in any way limiting its scope.

Example 1

This example demonstrates the existence of four UMOD gene mutations that segregate with the disease phenotype in three families with FJGN and in one family with MCKD2. These findings provide direct evidence that MCKD2 and FJGN arise from mutation of the UMOD gene and are allelic disorders. Accordingly, it is possible to assay for UMOD mutations to identify a propensity to develop FJHN and/or MCKD2.

Figure 1A:
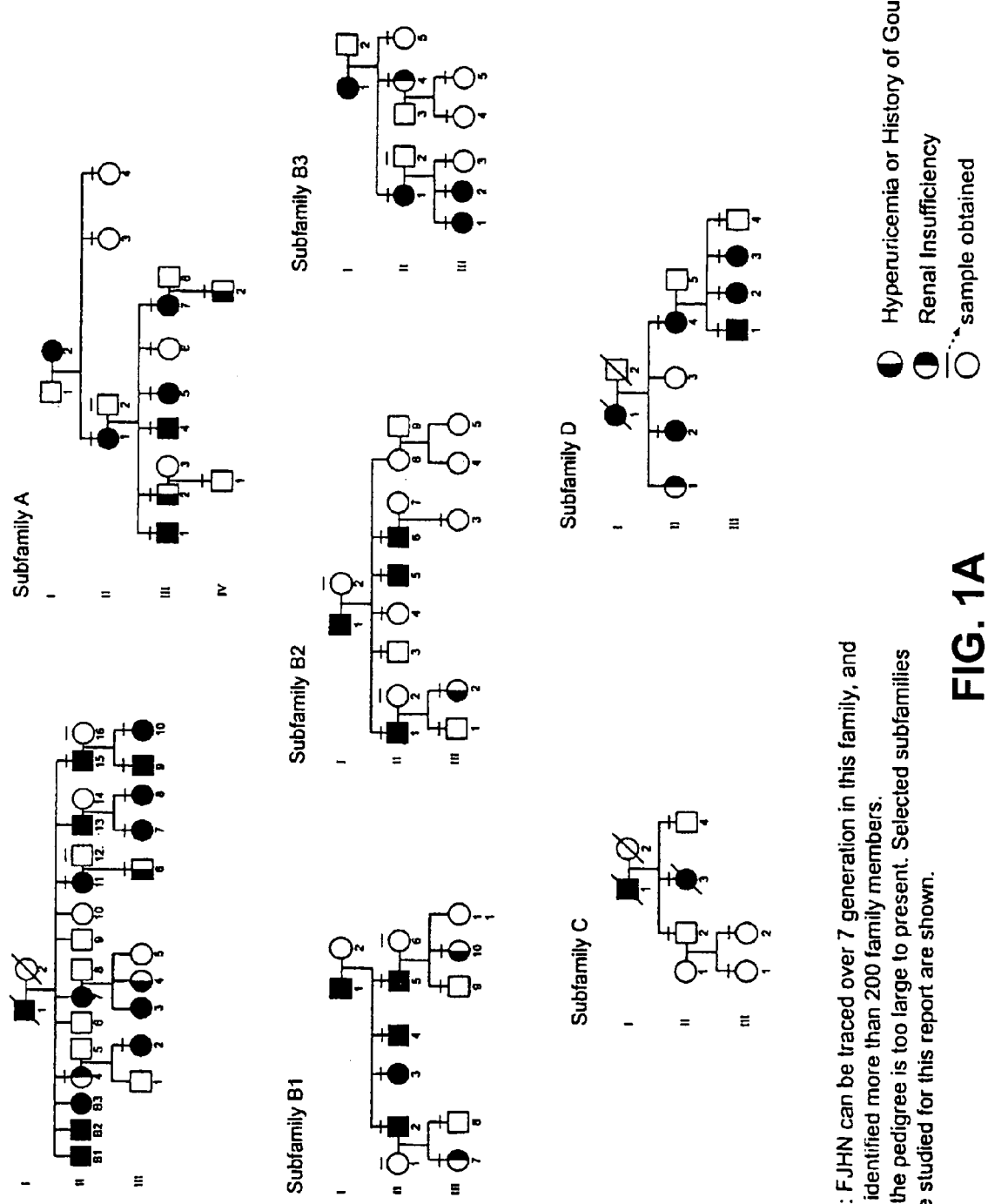
FIGS. 1A and 1B depict the pedigrees of families studied. Family 1: more than 300 individuals have been genealogically identified over 7 generations. The kindred is too large to include in total; thus, the nuclear families studied have been indicated for this report. These families are from different parts of this extended kindred, and are indicated as subfamilies A, B, C, and D. In addition eight singletons were studied. Clinical findings in affected family members are consistent with a clinical diagnosis of FJHN in Family 1. Family 2: Clinical findings in this family are consistent with a clinical diagnosis of FJHN. Family 3: Clinical findings and renal biopsy/autopsy reports are consistent with a clinical diagnosis of MCKD2 (Thompson et al., *Arch. Intern. Med,* 138, 1614-17 (1978)).
Figure 1B:
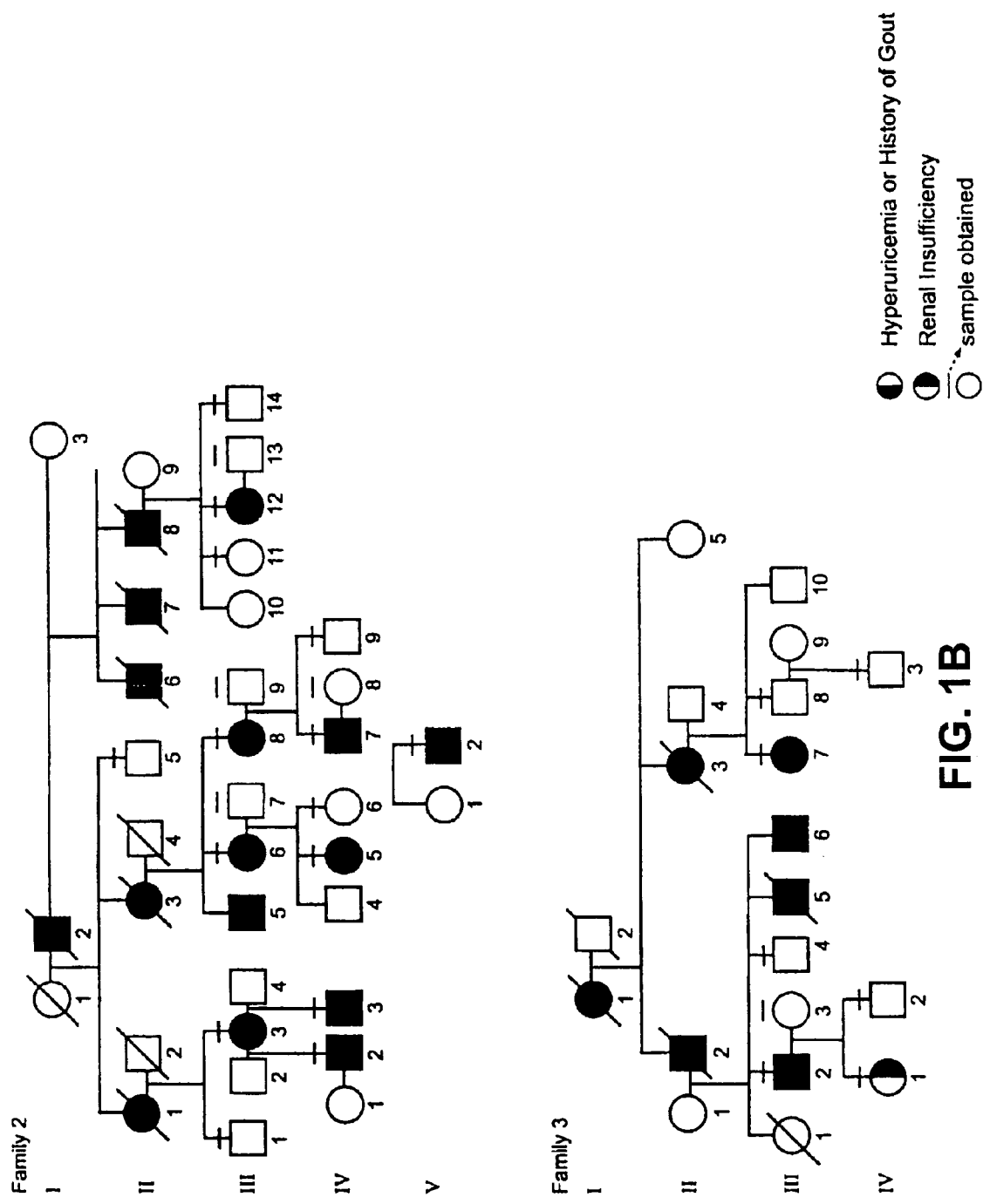

Patients and Methods
  Pedigrees and Diagnostics
    Study participants were obtained from four families. Family 1 was a large multi-generational family in which the disorder was traced back 7 generations. The family tree contains more than 300 members and was too large for the entire pedigree to be depicted. FIG. 1 shows the pedigree for selected portions of the family in whom the majority of samples were obtained. This family had a long history of hyperuricemia, reduced fractional excretion of uric acid, and renal failure, inherited in an autosomal dominant fashion, with clinical findings consistent with FJHN. Family 2 was a large multi-generational family that also segregated FJHN as a highly penetrant autosomal dominant trait. Family 3 has previously been reported to suffer from medullary cystic disease, hyperuricemia, and gout (Thompson et al., *Arch. Intern. Med.*, 138, 1614-17 (1978)), inherited in an autosomal dominant fashion (see FIG. 1). A sample was obtained from one affected family member from Family 4. Family 4 was previously extensively described in the literature as suffering from familial hyperuricemia and renal disease but no medullary cysts, findings consistent with a diagnosis of FJHN (Massari et al., *Arch. Intern. Med.*, 140, 680-84 (1980)). Family 5 was screened because family members had exhibited symptoms consistent with a diagnosis of FJGN.

Serum uric acid and serum creatinine measurements were performed, and 24-hour urine collections for uric acid and creatinine were obtained. The creatinine measurements were performed by the Jaffe alkaline picrate kinetic method (Tietz N W. *Clinical Guide to Laboratory Tests, 3d edition*. WB Saunders Company, Philadelphia, Pa.; 186-87 (1995)). The uric acid measurements were performed on the ADVIA 1650 Chemistry System. The uric acid determination method is based on the Fossati enzymatic reaction using uricase with a Trinder-like endpoint (Fossati, *Clin. Chem.*, 26, 227-231 (1980)). Estimates of creatinine clearance, as determined by the Cockroft-Gault formula (Cockroft et al., *Nephron*, 16, 31-41 (1976)), were made using the patient's weight or ideal body weight, whichever was less. Renal insufficiency was defined as an estimated creatinine clearance less than 80 ml/min. Enuresis was defined as persistent bed-wetting after the age of 4 years.

Patients were considered to be definitely affected if they met the following criteria: (1) Hyperuricemia, defined as serum uric acid levels greater than 2 standard deviations (s.d.) above the age- and gender-adjusted norms for the population (Wilcox, J. *Pediatr.*, 128:731-41 (1996); Mikkelsen et al., *Am. J. Med.*, 39, 242-51 (1965)) or a history of gout and current treatment with allopurinol, and (2) Reduced fractional excretion of uric acid (<5% for men and <6% for women) or a reduced creatinine clearance of less than 80 ml/min. (In general, individuals with a creatinine clearance less than 80 ml/min will start developing an elevated fractional excretion of uric acid (Rieselbach et al., *Nephron*, 14, 81-87 (1975)), and as such family members with renal insufficiency could not have their fractional excretion of uric acid used as a determinant of FJHN). Family members were defined as clinically unaffected if the serum uric acid level was within 1 s.d. of the age and gender-adjusted norms for the population (Wilcox; Mikkelsen et al.).

Figure 2:
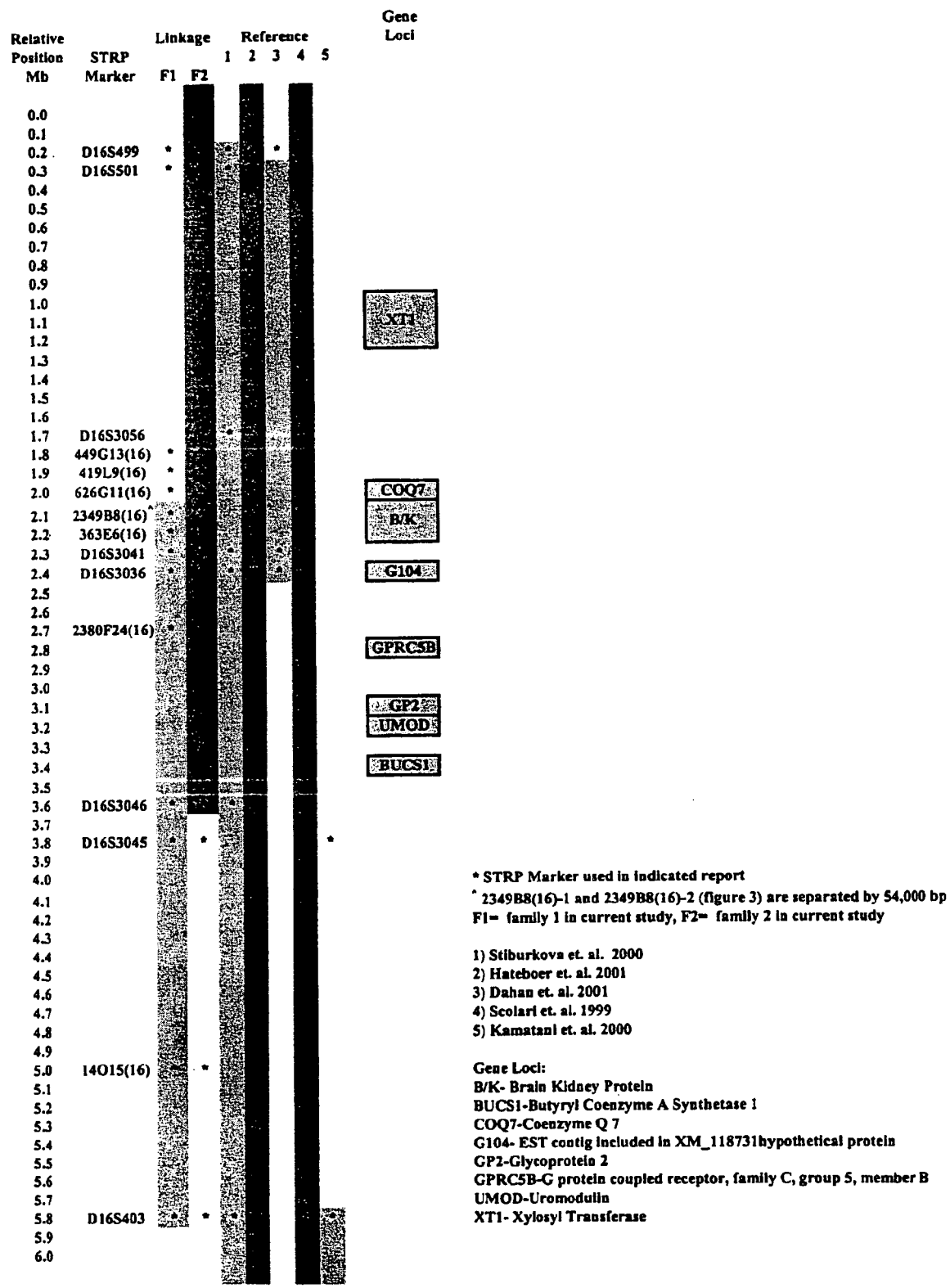
FIG. 2 depicts the integrated physical and genetic map of the FJHN/MCKD2 candidate region on chromosome 16p. Genetic STRP markers and their relative locations are indicated on the left. Locations of significant linkage results (LOD scores >3.0) are indicated for 2 families in the current report (Family 1 and Family 2) and for five other studies (referenced 1-5). Nine known STRPs and nine novel STRPs were identified, localized and genotyped. Two novel STRP loci were identified in BAC2349B8; the position of these loci (2349B8(16)-2 and 2349B8(16)-1) are separated by 54,000 bp as indicated in FIG. 2, and the order of these are given in FIG. 3. Genetic loci identified in the region are indicated to the right of the figure.
Figure 3:
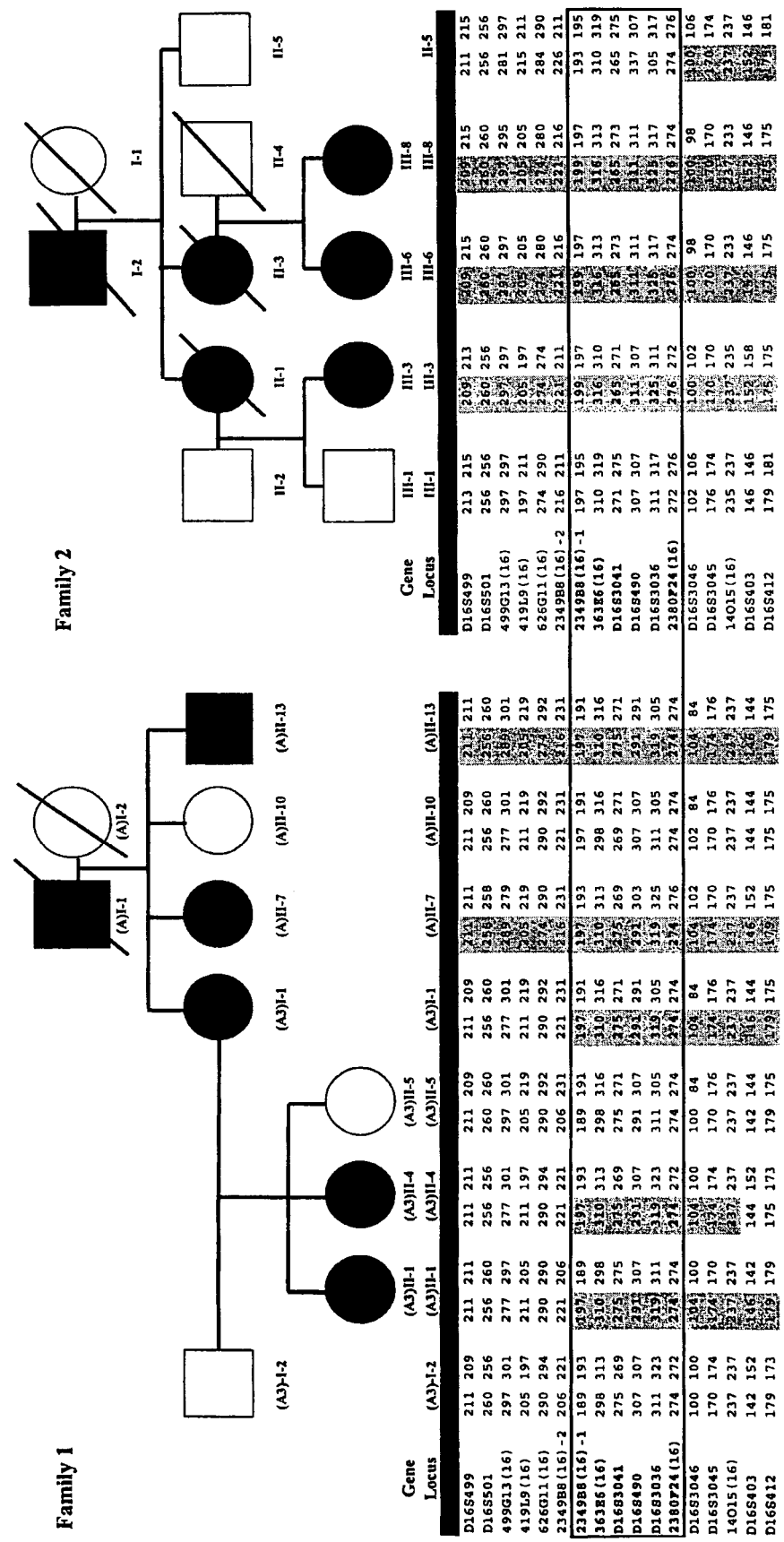
FIG. 3 depicts the haplotype results indicating the minimal genetic interval on chromosome 16 segregating with the FJHN phenotype in Family 1 and Family 2. FJHN affected individuals are indicated by shaded symbols, white circle and squares indicate unaffected family members, slash indicates deceased. Genetic STRP loci genotyped are listed in positional order in the left column for each family. Haplotypes segregating with the disease locus are shaded. Individual II-5 from Family 2 is unaffected, but has inherited the disease associated haplotype for the interval D16S412-D16S3046, indicating this region does not contain the FJHN disease locus. The boxed region indicates the minimal haplotype region segregating with the FJHN in both families, indicating the FJHN gene is within the interval flanked by 2349B8(16)-2 and D16S3046.

DNA-Marker Analysis
  Genomic DNA was extracted from peripheral blood by standard methods using the QIAamp blood kit (Qiagen). Genetic linkage studies were performed for 90 individuals from two extended multigenerational families diagnosed with FJHN (Family 1 and Family 2, FIG. 1). Available family members were genotyped for STRP-type (Short Tandem Repeat Polymorphism) genetic markers spanning the candidate interval. In addition to 9 previously reported STRP loci, 9 novel STRP loci were developed from a 5.6-Mb physical map of the interval (FIG. 2, FIG. 3). These marker loci were PCR amplified by use of fluorescence-labeled primers, permitting genotyping by conventional methods (Hart et al., *Am. J. Hum. Genet.*, 70, 943-54 (2002)). PCR products were detected by an ABI 377 fluorescent sequencer and were analyzed by GENESCAN 2.1 (Applied Biosystems).

Parametric Linkage Calculations: LOD Scores and Haplotype Analysis

Sub-localization of the candidate interval was achieved by means of genetic linkage studies and determination of the minimal region of overlap of haplotypes segregating with the FJHN trait in Family 1 and Family 2. Standard two-point and multipoint linkage analyses were performed using the VITESSE program (O'Connell et al., *Nat. Genet.*, 11, 402-08 (1995)). Assumptions of the linkage analyses included autosomal dominant transmission, penetrance values of 95-100%, a disease allele frequency of 0.0001, and a phenocopy rate of 1%. To permit identification of haplotypes, a physical map of the FJHN candidate gene region was developed. This map permitted precise localization of known STRP markers within the region and allowed identification of novel STRP markers at desired locations spanning the interval.

Development of a Physical Map of the Candidate FJGN Candidate Interval; STRP and Gene Identification To identify novel STRP-type markers spanning the candidate interval and to permit identification of all known and hypothetical genes within the interval, the development of a detailed physical/genetic map was initiated (Zhang et al., *Cyto. Genet. Cell. Genet.*, 95, 146-52 (2001)). The final alignment contained 67 BACS that span a 5.6 million base region. This region contains two gaps across which a BAC sequence did not align. This contig was screened for all known genes, and STRP loci were identified through the NCBI Human Genome Sequencing website and GENEMAP 99 gene website. Gene and STRP loci confirmed on the BAC contig were positioned on the new map. New STRP markers were identified using the Tandem Repeats Finder (Benson, *Nucl. Acids. Res.*, 27, 573-80 (1999); and on the internet. Candidate STRP sites were then selected and primers designed using Oligo 4.0 software.

Several sources of information were used to identify genes in the candidate region: The Human Genome Project Working Draft at UCSC, the Sanger Center's ENSEMBLE database and Locus Link (Benson). NCBI BLAST and ePCR were also used on the BAC contig sequence with the BLAST non-redundant and dbEST databases screened. A cDNA contig was made for each candidate gene using all information that was available at the time. The inclusion of all EST data provided for a more accurate representation of the gene. Intron/exon boundaries were determined manually using the consensus splice sequences indicated at GENIO/splice. Primers for amplifying candidate genes from genomic DNA were designed using data obtained from the primary contig as well as from available NCBI data (accession numbers in electronic references; NCB Locus Link, NCBI Entrez) [NCBI Locus Link for genes shown in FIG. 2—Locus ID Numbers are: XT1—64131 (SEQ ID NO:20), COQ7-10229 (SEQ ID NO:21), B/K-51760 (SEQ ID NO:22), G104-162074, GPRC5B-51704 (SEQ ID NO:23), GP2-2813 (SEQ ID NO:24), UMOD-7369 (SEQ ID NO:25), BUCS1-116285 (SEQ ID NO:26); NCBI Entrez Gene Accession Numbers: XT1-XM_485032 (SEQ ID NO:27), COQ7-NM_016138 (SEQ ID NO:28), B/K-NM_016524 (SEQ ID NO:29), G104-XM_091332 (SEQ ID NO:30), GPRC5B-NM 016235 (SEQ ID NO:31), GP2-NM_001502 (SEQ ID NO:32), UMOD-NM_003361 (SEQ ID NO:33), BUCS1-NM_052956 (SEQ ID NO:34)]. By means of linkage and haplotype analyses, the FJHN candidate region was refined to about an 1.7-Mb interval. Five known genes were localized to this interval. Additionally, using an integrated bioinformatic and bench lab approach, one previously uncharacterized genetic locus was localized within the interval. All exons and intron-exon boundaries of four of these genes were analyzed by sequence analysis of genomic DNA from affected and unaffected family members from Family 1 and Family 2.

UMOD Exon Sequencing

The genomic structure of the UMOD gene was determined bioinformatically and was confirmed by sequence analysis. Oligonucleotide primers to amplify 11 of the 12 exons, including intron-exon boundaries (Table 1), were designed with Oligo 4.02 (National Biosciences). PCR amplification of the UMOD gene was performed as indicated in Table 1.

TABLE 1

Primer Sets for Exonic Amplification of Human UMOD Gene

Primer (5'→3')

| Exon | SEQ ID NO | Forward | SEQ ID NO | Reverse | Size (bp) | PCR Condition[a] | GenBank Accession Number |
|---|---|---|---|---|---|---|---|
| 02-03 | 35 | TCCTGCTCCAAATGACTGAGTTCT | 36 | TCAACCCAATGGAATGACCTCTTA | 888 | B | AY162963 |
| 04-05 | 37 | GGTGGAGGCTTGACATCATCAGAG | 38 | GGAATAGGGCTCAGATGGTCTTTG | 1493 | A | AY162963 |
| 04-05[S] | 39 | GCCCTGGCCTCATGTGTCAATGTG | 40 | GGGTCACAGGGACAGACAGACAAT | | | AY162963 |
| 04-05[S] | 41 | CGGCGGCTACTACGTCTACAACCT | 42 | GTAGCTGCCCACCACATTGACACA | | | AY162963 |
| 06 | 43 | ACCTCTGGACCTCAAGTAATCTGT | 44 | TGATGCCTACTGGCTGAGACAATC | 940 | A | AY162964 |
| 07 | 45 | ACCAGCAGATTTAGCTTTGAAGTC | 46 | GCTTGAACCAGGCAGTGCTTTGAC | 475 | A | AY162965 |
| 08 | 47 | AGCAGCATCCAGGCACTTGTCAGA | 48 | TGAGGCAGAAGAATCACTTGAACC | 711 | B | AY162967 |
| 08[S] | | | 49 | TCCAAAGACCCCCTCTGAATTCTA | | | AY162967 |
| 09 | 50 | ATTTGAATCCAGGAAGTCTGACTC | 51 | GGCAAGCCACTGAAGTTCTCTGAG | 612 | B | AY162968 |
| 10 | 52 | GAGCGGCTCAGAGAACTTCAGTGG | 53 | CCCGTGTCCTGTGTTACATTCATC | 529 | B | AY162968 |

TABLE 1-continued

Primer Sets for Exonic Amplification of Human UMOD Gene

| Exon | SEQ ID NO | Forward Primer (5'→3') | SEQ ID NO | Reverse Primer (5'→3') | Size (bp) | PCR Condition[a] | GenBank Accession Number |
|---|---|---|---|---|---|---|---|
| 11 | 54 | GAGCCCCTGATGGGTCTGAAGTAG | 55 | TCTGAGCCACTCTCCTTATTTAGA | 345 | B | AY162969 |
| 12 | 56 | TAGATTGGGCACTTCACAAGAATG | 57 | ACAGCAGAACCCAGTCTCACTGAG | 733 | B | AY162970 |

[S]denotes primers also used in sequencing reactions. Sequencing was performed with BigDye Terminator System form ABI.
[a]The standard PCR amplification for each exon contains: taq (0.025 U/µl), 1X PCRx Enhancer Buffer, 25 nM each dNTP, and 1.5 mM MgSO4 A = 5% PCRx Enhancer B = 1X PCRx Enhancer Buffer, no PCR x Enhancer.
Cycling Conditions = 95-5' + 94-30"/56-30"/72-90" 35X + 71-10'

Amplified DNA was purified with the QIAquick PCR Purification Kit (Qiagen) and was sequenced using the BigDye Terminator Cycle Sequencing Kit on an ABI 3700 DNA Analyzer (Applied Biosystems) by the Genomics and Proteomics Core Laboratories of the University of Pittsburgh. Sequence analysis was performed with Sequencher 4.1 software (GeneCodes).

Results

Clinical Findings

Over a five-year period, clinical testing was performed on 72 members of Family 1. Thirty-one met strict criteria to be considered affected (hyperuricemia with reduced fractional excretion of uric acid or renal insufficiency), 22 were diagnosed as normal, and there were 10 unaffected spouses. For nine family members, a certain diagnosis could not be made. Thirty-four individuals suffered from hyperuricemia and 28 suffered from renal insufficiency. The pedigrees for families 2 and 3 identify all individuals who suffered from hyperuricemia or renal insufficiency.

Renal Biopsies

Pathologic samples were obtained by kidney biopsy in three members of Family 1. All three biopsies revealed histological changes of tubular atrophy and interstitial fibrosis. Global glomerulosclerosis was present, and there was no evidence of glomerulonephritis. In Family 2, a biopsy specimen of an affected female at age 39 years revealed widespread tubular atrophy. In Family 3, several autopsy specimens were obtained. The first was that of a 34-year-old man, revealing by report, tubules ensheathed by a dense acellular hyaline material (Thompson et al., Arch Intern Med., 138, 1614-17 (1978)). Medullary cysts were present. In another family member, autopsy studies again revealed sheathing of the tubules by fibrous tissue. In case three, tubules were ensheathed by dense acellular hyaline material (Thompson et al.). In Family 4, biopsy samples revealed focal tubular atrophy with interstitial fibrosis and lymphocytic infiltration. In summary, all biopsy specimens revealed focal tubular atrophy with interstitial fibrosis. Autopsy reports revealed tubules ensheathed by dense acellular hyaline material. Interstitial deposits of PAS-positive material also have been identified in medullary cystic kidney disease (Zager et al., Lab. Invest., 38, 52-57 (1978); Resnick et al., Lab. Invest., 38, 550-55 (1978)). Immunostaining of these deposits was found to be markedly positive with antibody to Tamm-Horsfall protein.

Physical Map of the Candidate Interval

Existing genetic and physical maps of the FJHN/MCKD2 candidate interval were generally poorly integrated and identified relatively few polymorphic genetic markers (STRPs) spanning the interval. This was problematic as a key marker (D16S3056) was uninformative in the families studied. The development of an integrated physical and genetic map of the FJHN/MCKD2 candidate interval (summarized in FIG. 2) permitted precise orientation of the results of previous linkage studies, to precisely localize known genes to the candidate interval, and to develop novel STRP loci. The availability of novel STRP markers permitted refinement of the candidate interval by haplotype analysis. The location of eight known and eight novel STRPs are shown in FIG. 2. Oligonucleotide primers and conditions used to amplify these STRPs are shown in Table 2.

TABLE 2

Primer Sets used in the amplification of STRP loci.

| Locus | SEQ ID NO | Forward Primer (5'→3') | SEQ ID NO | Reverse Primer (5'→3') | STRP[a] Size (bp) | STRP Type | Relative Position[b] |
|---|---|---|---|---|---|---|---|
| D16S499 | 58 | TCTCACAGTTCTGGAGGCTGGAAG | 59 | GGTGGACCCTAATTGCATAGGATTG | 210 | CA Repeat | 238,700 |
| D16S501 | 60 | TGTCCTCTAGGGGAAGAGATGTCT | 61 | AGGTCAGGGACCTAGTAACTACTC | 260 | CA Repeat | 305,100 |
| 481E9(16) | 62 | CCAGAGCCCTACAGGAGTGTACTG | 63 | CAAGACCAGGGGATCACAGTAACT | 320 | Di | 362,700 |
| 449G13(16) | 64 | CAGCCTGGGCAACAGAGACTC | 65 | AGGCGCTAAATTCAGAGCAAATAG | 300 | CA Repeat | 1,784,000 |
| 419L9(16) | 66 | GCTGTAATGGTGCTGTGTAAATCT | 67 | AAGAATCCTCCAGACTTCATACAC | 218 | CA Repeat | 1,983,000 |

TABLE 2-continued

Primer Sets used in the amplification of STRP loci.

| Locus | SEQ ID NO | Primer (5'→3') Forward | SEQ ID NO | Reverse | STRP[a] Size (bp) | STRP Type | Relative Position[b] |
|---|---|---|---|---|---|---|---|
| 626G11(16) | 68 | ATCAGCTTAGCAGACATCTCTTCC | 69 | CTTGTAGTCCCAGCTACTCAGTGG | 292 | CA Repeat | 2,019,000 |
| 234B8(16)-2 | 70 | CACGAGAATCCCTTGAACCTG | 71 | TGGCTCTCCACTCAGAGATTC | 214 | Penta | 2,050,000 |
| 2349B8(16)-1 | 72 | CTGTGGCTGGCTTGTTTCACTCAG | 73 | TTGGGTGGAGGCAATCCAAGTGTC | 201 | CA Repeat | 2,133,000 |
| 363E6(16) | 74 | TGTGTTATTGGTGAAATGCACATA | 75 | GGTGGCTCATGCCTGTAATTTGAG | 355 | Di | 2,250,000 |
| D16S3041 | | APPLIED BIOSYSTEM LINKAGE MAPPING SET, PANEL 73 | | | 270 | CA Repeat | 2,310,000 |
| D16S490 | 76 | TGACAGGCACATAGATTATTATGC | 77 | CGTACCCGGCTGATTATTTTAGAT | 357 | Tetra | 2,390,000 |
| D16S3036 | 78 | AGATAGGGGTCTAGTTTCATTATC | 79 | ACAAAGCTGGACATATCACACTAC | 310 | CA Repeat | 2,450,000 |
| 2380F24(16) | 80 | AGGCTGGTCTCGAACTCCTGACCT | 81 | GGGACTACAGGTGTGTGAATTTGA | 272 | Di | 2,730,000 |
| D16S3046 | | APPLIED BIOSYSTEM LINKAGE MAPPING SET, PANEL 22 | | | 110 | CA Repeat | 3,650,000 |
| D16s3045 | 82 | AGGACGGCTGAATGTCTGTCATCA | 83 | TTGGGGAGTCCCTAAATGACTTTA | 180 | CA Repeat | 3,790,000 |
| 14015(16) | 84 | GGCAGAAATGGCACATCTTAACTA | 85 | CAGCCTGGGTGACAGAGTGAGACT | 234 | CA Repeat | 5,040,000 |
| D16S403 | | APPLIED BIOSYSTEM LINKAGE MAPPING SET, PANEL 73 | | | 150 | CA Repeat | 5,820,000 |
| D16S412 | 86 | ACCCAGTAGAGACCCATCTTACTC | 87 | ACCCAGTAGAGACCCATCTTACTC | 180 | CA Repeat | 5,952,000[c] |

[a]STRP size indicates the region that the PCR amplified band will be in.
[b]Relative position refers to the locus location on the BAC contig alignment sequence
[c]This position determined using the Human Genome Project data from June 2002
Amplifications performed using standard Amplitaq Gold Conditions The consensus candidate interval for most reports, including the present linkage data, support a candidate interval located in 16p13.11 (D16S499) to 16p12.2 (D16S403). It is apparent from FIG. 2 that, while all linkage intervals reported for FJHN and MCKD2 map to chromosome 16p, not all overlap.

Linkage Analyses

Results of genetic linkage analyses localized the gene for FJHN in two of the families (Family 1 and Family 2) to an overlapping interval of about 1.7-Mb (FIG. 2). For Family 1 the gene was localized to an interval of about 3.8-Mb delineated by 2349B8(16) to D16S403 ($Z_{MAX}$=12.5@D16S3041, θ=0.01) and for Family 2 the linkage interval was ~17-Mb between D16S404 and D16S3046 ($Z_{MAX}$=3.2@D16S3041, θ=0.00); D16S404 extends about 14-Mb telomeric to D16S499. These findings were consistent with four (Dahan et al., *J. Am. Soc Nephrol.*, 12, 2348-57 (2001); Hateboer et al., *Kidney Int.*, 60, 1233-39 (2001); Scolari et al., *Am. J. Hum. Genet.*, 64, 1655-60 (1999); Stiburkova et al., *Am. J. Hum. Gen.*, 66, 1989-94 (2000)) of the previous 5 reports of linkage for FJHN to chromosome 16p. The present candidate interval did not overlap that of the fifth study (Kamatani et al., *Arthritis Rheum.*, 43, 925-29 (2000)) possibly reflecting genetic heterogeneity (they are the only group to study Japanese FJHN families).

Candidate Gene Evaluation; Mutation Analyses

Integration of all known linkage reports for FJHN with the present linkage data identified an interval of minimal overlap (<0.3-Mb) from 2349B8(16) to D16S3036 for the present linkage results with those of Dahan and co-workers (see FIG. 2) [Dahan et al., supra]. This gene identification approach identified 1 known gene (B/K protein; NM_016524) and one hypothetical gene (G104; XM_091332) in this common interval. Direct sequence analysis of genomic DNA from affected and unaffected family members from Family 1 and Family 2 for coding regions (including intron-exon junctions) of the B/K gene and the hypothetical gene G104 did not identify any alterations of DNA that would account for the FJHN trait in either family.

Because the definitive diagnosis of FJHN can be problematic (particularly in milder cases and in younger individuals), and incorrect diagnosis of family members can directly affect the boundaries of the candidate gene region, the present analysis proceeded using only linkage and genotype data from Family 1 and Family 2. Thus individuals who could not be diagnosed as affected based on the diagnostic criteria stated above were excluded from the present analysis. Similarly, individuals who did not have both normal renal function (calculated creatinine clearance greater than 100 ml/min) and a serum uric acid level within 1 s.d. of the mean adjusted for age and gender (Wilcox; Mikkelsen et al.) were excluded from the analysis to refine the candidate interval.

Figure 4:
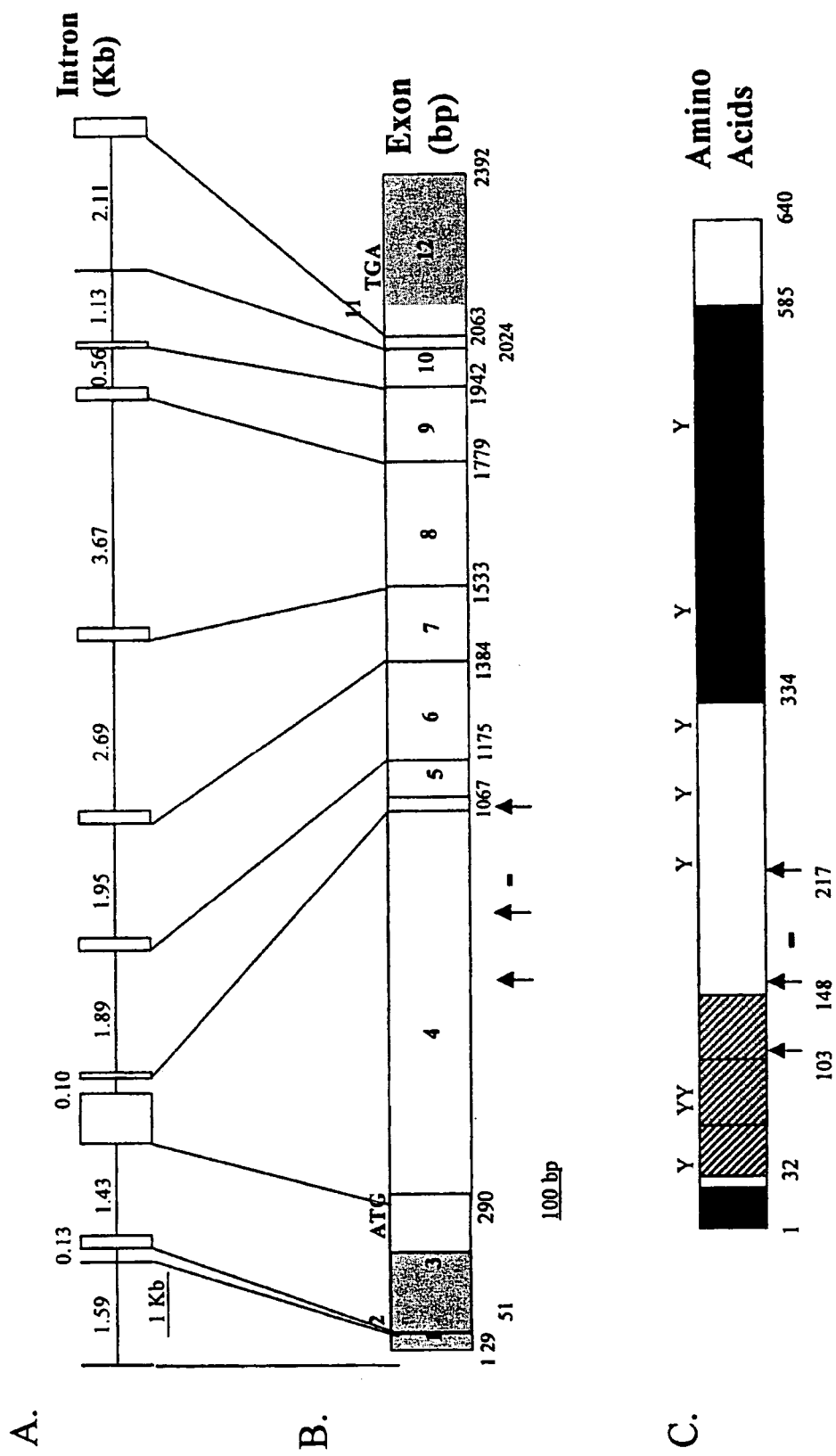
FIG. 4 depicts the structure of the human UMOD gene. A. Genomic organization of the UMOD gene. The exons and introns are represented as vertical boxes and horizontal lines respectively. The sizes of each intron are given in bp. B. cDNA structure of the UMOD gene. The translation start and stop codon are labeled as ATG and TGA, respectively. The 5' and 3' untranslated regions are shaded gray. The arrows indicate the missense mutations identified in this study. The horizontal bar indicates the deletion identified in this study. C. Structure of the wild-type UMOD protein. The inititation met is amino acid 1. The signal peptide is shown as a black box. The EGF-like domains are shown as dotted lines. The ZP domain is shown as a gray box. The eight potential glycosylation sites are shown as Y. The missense mutations identified in this study are shown as arrows with the corresponding amino acid listed below. The 9 amino acid deletion is shown as a horizontal bar. Additional recent preliminary data suggest that additional exons, other than those depicted in FIG. 4, may exist.

Haplotype analysis permitted the identification of the smallest common haplotype segregating with the FJHN trait in Family 1 and in Family 2 (FIG. 3). The present sequence analysis had excluded the known (B/K protein) and hypothetical gene (G104) from the interval 2349B8(16)-D16S3036, to permit refinement of the candidate interval to about 1.2-Mb, from D16S3036-D16S3046. This revised candidate interval contains 4 genes: butyryl coenzyme A synthetase 1 (BUCS1); glycoprotein 2 (GP2); G protein coupled receptor, family C group 5, member B (GPRC5B); and UMOD. Sequence analyses of GPRC5B and UMOD were performed for genomic DNA from affected and unaffected family members. No coding region polymorphisms were detected in the GPRC5B sequence data. To determine the genomic organization of the entire UMOD gene, all available UMOD mRNA and EST data were aligned to identify any possible splice variants. Using bioinformatic approaches, the genomic structure of the UMOD gene was determined (see FIG. 4). This approach led to the identification of 12 UMOD exons, which is one exon more than previously reported (Pennica et al., *Science*, 236, 83-88 (1987)). The novel exon identified by the present approach and supported by EST data is exon 2. Exons 1 and 2 are non-coding with the ATG start site in exon 3. Based upon EST data, there appear to be alternate 5' transcription start sites so that transcription either begins with exon 1 and proceeds to exon 3 or transcription begins in exon 2 and proceeds to exon 3. In either case, the resultant protein is identical.

UMOD sequence analysis was undertaken on Families 1 and 2. Results of sequence analysis revealed 2 different mutations in exon 4 of UMOD in Families 1 and 2 (FIG. 5A, 5B). Mutations are described according to nomenclature guidelines (Antonarakis, *Hum. Mutat.*, 11, 1-3 (1998); Den Dunnen et al., *Hum. Mutat.*, 15, 7-12 (2000)). In each family, (g. 1966__1992del in Family 1 and g.1880G>A in Family 2), the UMOD exon 4 gene mutation segregated completely with the disease phenotype. To evaluate the possible involvement of UMOD mutations in MCKD2, sequence analysis on 3 affected and 5 unaffected family members from a smaller family segregating MCKD2 (Family 3, FIG. 1) was conducted. Analysis of this family identified a third novel mutation (g.1744G>T) in UMOD, also in exon 4 (FIG. 5C). To evaluate the generality of UMOD mutations in FJHN, we performed mutational analyses on an affected member from an extended kindred previously reported (Massari et al., *Arch. Intern. Med.*, 140, 680-84 (1980)). This analysis revealed a fourth novel mutation (g.2086T>C) in exon 4 of UMOD (FIG. 5D). Affected individuals in family 5 contained another mutation (g.2105G>A, c.668G>A, p.C223Y).

The specific UMOD gene mutations in Family 1, Family 2 and Family 3 each segregated in affected family members (FJHN in Family 1 and Family 2; and MCDK2 in Family 3). None of these mutations were identified in any of the 100 control chromosomes tested. Sequence analysis of the UMOD gene in 50 Caucasian controls (100 chromosomes) did reveal the presence of two silent polymorphisms within UMOD Exon 4. A previously reported synonymous SNP (Pirulli et al., *J. Nephrol.*, 14, 392-96 (2001)) located at C174, has a T allele frequency of 82% and a C allele frequency of 18% for our samples. A novel synonymous SNP located at V287, has a G allele frequency of 87% and an A allele frequency of 13%. No polymorphisms affecting the translation of UMOD were detected in any of the 100 control chromosomes examined.

Genotype-Phenotype Correlation

For Family 1, 36 family members carried the mutation and 26 family members did not. Thirty-two of 36 (89%) genetically affected individuals suffered from hyperuricemia (as defined in Methods, supra). Twenty-eight of 32 (88%) genetically affected family members had an estimated creatinine clearance less than 90 ml/min when measured after the age of 18 years. Ten of 36 (28%) individuals carrying the UMOD mutation suffered from enuresis. The fractional excretion of uric acid was less than 6% in all genetically affected men and less than 5% in all genetically affected women with an estimated creatinine clearance greater than 70 ml/min. (The fractional excretion of uric acid increases in patients as renal function declines (Rieselbach et al., *Nephron*, 14, 81-87 (1975))). Thirty-two of 36 individuals carrying the UMOD mutation met the strict clinical criteria required to be diagnosed as affected. The remaining four individuals were women who had normal serum uric acid levels despite low fractional excretions of uric acid. Two of these women had mild renal insufficiency. The serum uric acid levels remained normal or borderline on testing over several years in three of these women. Five family members who did not carry the UMOD mutation had serum uric acid levels which were elevated but which were not greater than 2 standard deviations above the mean.

In family 2, nine of nine patients with the mutation suffered from hyperuricemia, and 9 of 9 patients suffered from renal insufficiency. In Family 3, 2 of 3 family members carrying the mutation suffered from hyperuricemia, and all three affected family members suffered from renal insufficiency.

These data are surprising given that recently one study has excluded UMOD as a candidate gene for a large Italian family segregating MCKD2 (Pirulli et al., supra). Although this study reports that the entire UMOD coding region was sequenced, this was performed with different primer sets than those used in the current study. Methodological differences in sequencing of exon 4 might account for the different results, however, other possibilities must be considered. Deletion of an entire exon could result in PCR amplification of only the wild type allele, masking the presence of a mutation. Pirulli et al. did not analyze the non-coding exons 1 and 2, nor the 5' regulatory region of UMOD. It is possible that mutations in exon 1, exon 2 or the regulatory region could result in loss of UMOD production (Salowsky et al., *Gene*, 293, 9-19 (2002); Flagiello, Mutations in brief no. 195. Online. *Hum. Mutat.*, 12, 361 (1998)). Alternately, genetic heterogeneity may exist with another kidney specific gene located in the candidate interval.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of diagnosing familial juvenile gouty nephropathy (FJGN) or a predisposition to contract FJGN, the method comprising
    (a) obtaining genetic material from a human test subject;
    (b) assaying the genetic material to detect the g.1966_1992del; c.529_555del mutation, the g.1880G>A; c.443G>A mutation, or a combination thereof, in at least one copy of the uromodulin (UMOD) genetic sequence, and
    (c) diagnosing FJGN or a predisposition to contract FJGN in said test subject based on the presence of said mutation or mutations.

2. The method of claim 1, wherein the genetic material is genomic DNA.

3. The method of claim 1, wherein the genetic material is RNA.

4. The method of claim 1, wherein the genetic material is a synthetic copy of the DNA or RNA of the test subject.

5. The method of claim 1, wherein assaying comprises obtaining the sequence of at least a portion of the genetic material.

6. The method of claim 1, wherein assaying comprises obtaining the sequence of substantially all of the genetic material.

7. The method of claim 5, wherein assaying comprises obtaining the sequence of substantially all of the genetic material.

8. The method of claim 1, wherein assaying comprises exposing the genetic material to a hybridization probe substantially specific for the g.1966_1992del; c.529_555del mutation and detecting the presence or absence of hybridization of the probe to the genetic material.

9. The method of claim 1, wherein assaying comprises exposing the genetic material to a hybridization probe substantially specific for the g.1880G>A; c.443G>A mutation and detecting the presence or absence of hybridization of the probe to the genetic material.

10. The method of claim 1, wherein the mutation is the combination of g.1966_1992del; c.529_555del and g.1880G>A; c.443G>A.

11. A method of diagnosing familial juvenile gouty nephropathy (FJGN) or a predisposition to contract FJGN, the method comprising
    (a) obtaining genetic material from a human test subject;
    (b) assaying the genetic material to detect the g.1966_1992del; c.529_555del mutation in at least one copy of the uromodulin (UMOD) genetic sequence, and
    (c) diagnosing FJGN or a predisposition to contract FJGN in said test subject based on the presence of said mutation.

12. A method of diagnosing familial juvenile gouty nephropathy (FJGN) or a predisposition to contract FJGN, the method comprising
    (a) obtaining genetic material from a human test subject;
    (b) assaying the genetic material to detect the g.1880G>A; c.443G>A mutation in at least one copy of the uromodulin (UMOD) genetic sequence, and
    (c) diagnosing FJGN or a predisposition to contract FJGN in said test subject based on the presence of said mutation.

* * * * *